(12) United States Patent
Tunesi

(10) Patent No.: US 10,966,904 B2
(45) Date of Patent: Apr. 6, 2021

(54) CONTAINER SYSTEM AND METHOD

(71) Applicant: Boehringer Ingelheim Vetmedica GmbH, Ingelheim am Rhein (DE)

(72) Inventor: Cristiano Tunesi, Sant Cugat del Valles (ES)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 572 days.

(21) Appl. No.: 15/841,508

(22) Filed: Dec. 14, 2017

(65) Prior Publication Data
US 2018/0168930 A1 Jun. 21, 2018

(30) Foreign Application Priority Data

Dec. 16, 2016 (EP) .................................. 16 020 500

(51) Int. Cl.
| | |
|---|---|
| *A61J 1/18* | (2006.01) |
| *A61J 1/20* | (2006.01) |
| *B65D 21/02* | (2006.01) |
| *B65D 81/32* | (2006.01) |
| *A61J 1/14* | (2006.01) |

(Continued)

(52) U.S. Cl.
CPC ............... *A61J 1/18* (2013.01); *A61J 1/1406* (2013.01); *A61J 1/1412* (2013.01); *A61J 1/2089* (2013.01); *B65D 21/0231* (2013.01); *B65D 71/50* (2013.01); *B65D 81/3211* (2013.01); *G08B 5/36* (2013.01); *A61D 1/025* (2013.01); *A61J 1/201* (2015.05); *A61J 1/2027* (2015.05); *A61J 1/2051* (2015.05); *A61J 2200/70* (2013.01); *A61J 2205/20* (2013.01)

(58) Field of Classification Search
CPC .......... A61J 1/18; A61J 1/2089; A61J 1/1406; A61J 1/1412; A61J 2200/70; A61J 1/2027; A61J 1/2051; A61J 1/201; A61J 2205/20; A61J 1/2093; A61J 1/10; B65D 21/0231; B65D 71/50; B65D 81/3211; G08B 5/36; A61D 1/025; A61P 31/00; B65B 55/02
See application file for complete search history.

(56) References Cited

U.S. PATENT DOCUMENTS

| | | |
|---|---|---|
| 4,223,801 A | 9/1980 | Carlson |
| 4,895,257 A | 1/1990 | Winslow |

(Continued)

FOREIGN PATENT DOCUMENTS

| | | |
|---|---|---|
| DE | 43 16 688 A1 | 11/1994 |
| DE | 10 2016 001 923 A1 | 8/2017 |

(Continued)

*Primary Examiner* — Nicholas J. Weiss
*Assistant Examiner* — Alessandro R Del Priore
(74) *Attorney, Agent, or Firm* — David S. Safran; Roberts Calderon Safran & Cole, P.C.

(57) ABSTRACT

A container system having at least two containers, wherein the container system comprises a light member which is configured to provide information through the emission of light, wherein the container system is configured to provide or trigger the light member to provide the information through the emission of light when a step related to preparing a mixture of contents of the containers is performed. In particular, triggering occurs when the containers are separated from one another and/or when a fluidic connection is created between the containers.

17 Claims, 32 Drawing Sheets

(51) Int. Cl.
 *B65D 71/50* (2006.01)
 *G08B 5/36* (2006.01)
 *A61D 1/02* (2006.01)

(56) References Cited

U.S. PATENT DOCUMENTS

| | | |
|---|---|---|
| 5,313,439 A | 5/1994 | Albeck |
| 5,838,224 A | 11/1998 | Andrews |
| 6,474,467 B1 | 11/2002 | Kurdian |
| 6,826,119 B2 | 11/2004 | Fortune |
| 7,392,953 B2 | 7/2008 | Chu |
| 7,643,378 B2 | 1/2010 | Genosar |
| 8,162,914 B2 | 4/2012 | Kraushaar et al. |
| 9,078,809 B2 | 7/2015 | Bochenko et al. |
| 9,308,151 B2 | 4/2016 | Chaturvedi et al. |
| 9,311,452 B2 | 4/2016 | Dickie et al. |
| 9,474,692 B2 | 10/2016 | Rauleder et al. |
| 9,891,202 B2 | 2/2018 | Rolff et al. |
| 2002/0139708 A1 | 10/2002 | Lien |
| 2005/0190548 A1* | 9/2005 | Cohen .................. B65D 23/00 362/34 |
| 2006/0139928 A1 | 6/2006 | Griffiths et al. |
| 2008/0255515 A1* | 10/2008 | Grinberg ............. A61M 5/3135 604/111 |
| 2011/0089065 A1* | 4/2011 | Bottger .................... A61J 1/00 206/438 |
| 2012/0323208 A1 | 12/2012 | Bochenko et al. |
| 2014/0251851 A1 | 9/2014 | Huntley |
| 2015/0261192 A1 | 9/2015 | Spivack et al. |
| 2015/0332575 A1 | 11/2015 | Huntley |
| 2016/0166471 A1* | 6/2016 | Tobescu ................... A61J 1/18 340/691.6 |
| 2016/0228328 A1 | 8/2016 | Wengreen et al. |
| 2016/0361231 A1 | 12/2016 | Chou et al. |

FOREIGN PATENT DOCUMENTS

| | | |
|---|---|---|
| WO | 2005047129 A1 | 5/2005 |
| WO | 2014/020326 A2 | 2/2014 |
| WO | 2015/075221 A1 | 5/2015 |
| WO | WO-2015075221 A1 * | 5/2015 ............ A61J 1/2089 |

\* cited by examiner

CONTAINER SYSTEM AND METHOD

BACKGROUND OF THE INVENTION

Field of the Invention

The present invention relates to container systems comprising at least two containers that are fluidically connectable.

In medicine, it is known to transfer substances from one container into another. For example, mixtures of medicaments or substances are produced in a mixing bottle, by transferring first the contents of one container and then of a second container into the mixing bottle, then sealing the mixing bottle, and producing a mixture by agitation.

Description of Related Art

International Patent Application Publication WO 2013/104550 A and corresponding U.S. Pat. No. 9,474,692 relate to a kit for the production of a combined vaccine, wherein two bottles each have a septum and the kit comprises a double needle for piercing both septa and thereby providing a continuous fluidic connection between the bottles.

A mixture of substances can have a limited viability, for example due to physical, chemical or biological processes affecting active substances within the mixture. Accordingly, there is a period of time, starting from the point in time where the mixture is produced and ending where the viability cannot be guaranteed any more, referred to as viability or viability time span or just period time. The viability in particular can be based on or influenced by potential contamination, oxidation, coagulation or interaction of the substances.

SUMMARY OF THE INVENTION

A primary object of the present invention is to provide a container system and a method for improving reliability or application safety, in particular of mixtures having a limited viability.

This object is achieved by a container system and a method as described herein.

The present disclosure generally relates to packages preferably including one or more medicaments therein, such as a vaccine. In particular, the present disclosure relates to packages, such as containers like medication bottles, that comprise or include one or more light members thereon that may be activated at a desired time to provide an end user of the package with information about the package or the contents therein. The packages including the light members thereon may reduce improper use of the medicament contained therein and improve overall compliance with instructions for proper use.

Farm animals receive numerous vaccines and medicaments over their lifetime to ensure their health and well-being. Some vaccinations are given once during the life of the animal while others are given annually. To save on costs, many farmers administer the vaccinations themselves rather than enlisting the services of a professional veterinarian. In some countries, health and safety regulations permit the farmer to administer the vaccinations to their herd, while in other countries a professional veterinarian is required.

For example, bovine viral diarrhea ("BVD") is the number one economically significant disease in cattle worldwide with infections occurring in all countries where cattle are raised. Although it is normally an infection of cattle, it has the ability to cause infections in other animals such as pigs, sheep, goats, alpacas, deer, reindeer, and bison. An infection by this virus may be difficult to recognize and only a small percentage of infected animals show clinical signs of infection. This virus is well known for reducing milk production and increasing the risk of death. It can stress adult cattle and produce abortions and birth defects in calves that are born to mothers that are infected by the virus. The economic impact worldwide is substantial.

In spite of the availability of several commercial vaccines like that for BVD, infections are still quite common worldwide. Although conventional parenteral and intranasal vaccines and methods of vaccination are available, they may not always be completely effective or safe. Also, cattle do not always respond uniformly immunologically to any vaccination. The range of immune responses can vary from no response at all to a very high level of response when such cattle are treated with the same batch of vaccines.

Vaccine failure is caused by many different factors, including the immune status of the animal, the environment in which the animal lives or the vaccine is administered, the specific pathogen, and improper administration. Eliminating or reducing the factors that contribute to vaccine failure is a significant issue for all farmers who manage herds because their economic livelihood depends on having healthy and productive animals. Because the farmer or professional veterinarian is often working in low light conditions, and are often interrupted when attempting to vaccinate their animals, one form of improper administration that occurs is administration of the vaccine after it is no longer viable. This can greatly reduce or entirely eliminate the effectiveness of the vaccine. Additionally, some vaccines combination vaccines or other mixtures have a short time period in which they remain viable once mixed, reconstituted or removed from refrigerated storage.

Furthermore, farmers often work with their animals in the early morning or under the poor lighting conditions of a barn. Farm animal vaccinations are often done in the winter when the animals are indoors which acerbates the low light conditions. In either case, the visibility of a vaccine bottle and/or the septa in the serum cap by which a syringe needle accesses the vaccine bottle contents is important. Poor visibility can lead to a need-stick or other adverse consequences for the farmer, veterinarian, or the animal.

Because it is impossible to determine if a vaccine or immunogenic composition is still viable after reconstitution, mixing or removal from refrigerated storage based on visual examination, a need exists to enable a farmer, veterinarian, or other end-user to make this determination in a simple, easy, and effective manner Additionally, a need exists to assist the end-user in seeing and administering a vaccine to an animal under poor or low light conditions.

The present invention is generally directed to packages that preferably include at least one medicament therein. Particularly preferably, the term "package" covers a container system or one or more containers of such container system or a packaging thereof or related thereto. Thus, the terms "package" and "container" can be replaced where not explicitly indicated to the contrary.

The packages preferably include at least one light member affixed thereto that is capable of emitting light upon activation. In many embodiments as described herein, the light member is activated upon the opening of the package or any step up to the way of preparing a mixture of the contents of the containers of the container system such that upon opening or said step, the light member fluoresces or otherwise emits light to provide information to the ambient or to an end user.

In some embodiments, the light generated by the light member allows the end user to locate and utilize the package in dark conditions.

In other embodiments, the light generated by the light member may be configured such that it is emitted only for a time period equal to the viability time period of the medicament or mixture contained within the package to alert an end user when the medicament or mixture is no longer useable.

In still other embodiments, the light generated by the light member may be configured such that it changes color at a time period equal to the viability time period of the medicament or mixture contained within the package to alert an end user that the medicament or mixture is no longer useable.

The present disclosure preferably is directed to a package comprising: (i) preferably a medicament, and (ii) a light member. The light member preferably is located on the exterior of the package, and/or is configured to provide information to the ambient or to an end user through the emission of light.

The present disclosure is further directed to a method for determining the viability of a medicament in a package. The method comprises (i) activating a light member on the package, preferably comprising said medicament, when the package is opened or when any step up to the way of preparing a mixture of the contents of the containers of the container system forming or comprising the package is conducted; and (ii) preferably observing the fluorescence in the light member.

The present disclosure is further directed to a method for determining the viability of a medicament or mixture in a package. The method comprises: (i) opening the package and/or conducting a step directly related to mixing contents, (ii) activating a light member located on the package containing the medicament or mixture such that the light member emits fluorescent light; and (iii) preferably observing a change in color in the light member over a period of time.

A first aspect the present invention relates to a container system having at least two containers. The container system comprises a light member which is configured to provide information, preferably to an end user to the ambient and/or visible from the outside, through the emission of light. The container system is configured to provide information through the emission of light—preferably automatically—when a step which is directly related to preparation of a mixture of contents of or substances stored inside the containers is conducted.

Alternatively or additionally, the container system generally is configured to provide information through the emission of light.

Using the emission of light for providing a user with information enables secure usage of the system or mixtures prepared using the system particularly in dark areas like barns. Further, by means of the lighting member the information is emphasized. Accordingly, the information is less likely overseen or ignored.

Preferably, the container system is configured to provide information through the emission of light—preferably automatically—when a fluidic connection is prepared between the containers. In particular, the container system is configured to activate the light member to emit light or to change properties of light emitted by the light member when the fluidic connection is prepared between the containers.

The containers preferably each comprise a connecting arrangement. The connecting arrangements are configured for the preparation of the fluidic connection between the containers, preferably wherein the connecting arrangements are configured to prepare the fluidic connection by insertion of one connecting arrangements into the other and/or by twisting the connecting arrangements relative to one another.

Alternatively, or additionally, the container system is configured to provide information through the emission of light—preferably automatically—when the containers are separated from one another. The containers can be stored, provided or be initially in a transporting position releasably connected to one another. The container system preferably is configured to—preferably automatically—activate the light member to emit light or to change properties of light emitted by the light member when the containers are separated from one another while the containers keep closed.

Both separating the containers and connecting them by means of the fluidic connection can form steps of the process for mixing contents or substances stored inside of the containers. Generally, any step which is directly related to preparing of the mixture of contents or substances stored inside the containers is can be used to control or trigger the lighting member.

As the container system is configured to enable mixing up the contents of the containers and the mixture prepared from the contents can be used, it is advantageous to provide the information at the time of or immediately prior to preparation of the mixture. This can be achieved by triggering the light member to emit light or to change properties of light emitted by the light member.

The information provided to the end user preferably is related to the viability of a medicament or mixture which can be prepared by mixing up contents of the containers.

In one aspect of the present invention, the light member is configured to emit light for a predetermined period of time or to change properties of light emitted by the light member after a predetermined period of time. Particularly preferably, said period of time corresponds to or complies with the period of time for which the medicament or mixture remains viable.

As already indicated, a mixture of substances can have a limited viability, for example due to physical, chemical or biological processes affecting active substances within the mixture and there can be a period of time, starting from the point in time where the mixture is produced and ending where the viability cannot be guaranteed any more, referred to as viability or viability time span. The viability in particular can be based on or influenced by potential contamination, oxidation, coagulation or interaction of the substances.

By means of the light member triggered by a step performed at the time or for enabling mixing the contents of the containers, the present invention provides an indicator for the viability or that the mixture is not viable anymore which is easy to be identified, even under dark conditions. Further, the emitted light can be registered by an end user directly or by means of reflected or scattered light even in cases where one container of the container system is inserted into an administration device like an injector or a syringe.

The light emission preferably is produced by fluorescence, chemiluminescence, or a light emitting diode. Alternatively, or additionally, the light member uses passive illumination, active illumination or a combination thereof.

Preferably, the light member is activated by the combination of two or more chemicals. Said chemicals preferably are separated from one another and the container system is adapted to cause the chemicals to come into contact when the step related to mixing the contents is conducted, when the fluidic connection is prepared and/or when the container are separated.

The light member preferably is part of the exterior adornment of the container system or one or more of the containers of the container system. This facilitates to attract attention directly and without loss of light intensity when the light member is covered, which, however, is possible as well.

A further aspect of the present invention, which can be realized independently as well, relates to a method for determining the viability of a medicament or mixture which is prepared by mixing contents of at least two containers using a fluidic connection between said containers, wherein information is provided through the emission of light when a step which is directly related to preparation of a mixture of contents of or substances stored inside the containers is conducted.

Preferably, information is provided through the emission of light when the containers are separated from one another or when a fluidic connection is prepared between the containers or when a different step directly related to preparing a mixture of contents of the containers is conducted.

Alternatively, or additionally, the containers each comprise a connecting arrangement configured for the preparation of the fluidic connection between the containers, wherein the light member is—preferably automatically—activated when the fluidic connection between the containers is prepared.

Preferably, activating the light member comprises causing two or more precursor chemicals to mix and/or exposing the light member to light for at least a set time period. Such precursor chemicals in the following are also referred to as chemical components.

In one aspect of the present invention, the light member emits light for a period of time or changes a lighting property after said period of time. Said period of time preferably is equal to the length of time for which the medicament or mixture remains viable or is pre-known or predetermined to be viable.

A color change of the light emitted by the light member can occur or the light member can stops emitting light at the time when the medicament or mixture become non-viable or is considered non-viable due to expiry of a minimum predetermined shelf life.

This period of time preferably complies with a minimum shelf life or durability of the mixture that can be obtained by mixing up the contents of the containers and/or the mixture preferably is considered to be non-viable when the minimum shelf life or durability of the mixture has expired. Thus, the period of time can be the time span the mixture is deemed to be viable.

As already indicated, the container system comprises at least two containers, preferably bottles. The containers preferably comprise connecting arrangements configured to provide for a (continuous) fluidic connection between containers.

The containers can be fluidically connected to one another by means of the connecting arrangements, so that the substances are mixed together, particularly to form the combined vaccine. During or by preparing this fluidic connection, the lighting member can (automatically) be triggered. In particular, the lighting member is automatically triggered when the connecting arrangements are docked to one another, inserted into one another, and/or rotated relative to one another. It is not necessary that the fluidic connection is completed for triggering the lighting member. It might be sufficient to perform one step on the way to establish the fluidic connection to trigger the lighting member.

Triggering the lighting member according to the present invention preferably means activating the lighting member to emit light. Alternatively, or additionally, starting a time span after which the a stop or start of limit emission, or after which properties of the emitted light are (automatically) changed visibly to an end user can be understood as triggering the lighting member. Said time span preferably is or complies with the period of time the mixture is or is deemed viable.

One or both of the containers can comprise a removal opening in addition to the connecting arrangements, the removal opening(s) being re-closeable and configured to remove the substance or mixture from the container(s). The removal opening can be or comprise a septum.

The first container can comprise a first substance, particularly a first vaccine against a first disease, while a second container comprises a second substance, particularly a second vaccine against a second disease different from the first, for the preparation of a mixture of substances, particularly for the preparation of a combined vaccine for simultaneous immunization against different diseases. However, the containers can comprise different substances as well.

In the sense of the present invention the terms "substance" and "content" (as stored in said containers in an initial state) are used exchangeably and can be replaced unless indicated to the contrary. Said substances or contents can comprise a medicament, an active substance of a medicament, a liquid, a dry substance like a lyophilisate, said substances or contents can be or be a medicament, an active substance of a medicament, a liquid, a dry substance like a lyophilisate or can be configured to form a medicament when mixed.

The containers preferably comprise substances that, when mixed, have a limited viability, preferably in the sense as previously explained.

The containers and/or the connecting arrangements preferably are fluidically sealed in an initial state or prior to connecting them fluidically. After the fluidic connection has been prepared, the containers have a joint inner room covering the substances which can be mixed, thus forming the mixture.

The connecting arrangements preferably each comprise an opening region, in particular being unstable, frangible and/or having a predetermined breaking point/line.

In one aspect, the first connecting arrangement preferably is deformable outside the opening region and is configured so that the deformation opens the first connecting arrangement in the opening region. This deformation can be effected by the second connecting arrangement. Alternatively, the first connecting arrangement can be pierced by the second connecting arrangement to provide the fluid connection. Said deformation or the first or second connecting arrangement during or by means of the deformation process can trigger the lighting member.

The first connecting arrangement has a preferably rigid closure device, particularly a closure plate, which is sealingly held on a holding portion of the connecting arrangement in an initial state by means of a frangible point/line, particularly a fragile thin point/line, the holding portion being movable relative to the closure device by deformation, as a result of which the first connecting arrangement can be opened by breaking, particularly tearing/cracking, the frangible point/line.

The first connecting arrangement preferably comprises a severing element, particularly a piercing element and/or cutting edge, by means of which the second connecting arrangement can be opened. The deforming device preferably corresponds to the holding portion, formed in particular by a mouth-shaped portion The connecting arrangements can be sealingly inserted in one another and, when the connecting arrangements are rotated relative to one another, the first connecting arrangement can be opened, as a result of deformation of the holding portion by means of the deforming device, in order to produce the fluidic connection.

The second connecting arrangement preferably comprises a deforming device for opening the first container by means of the first connecting arrangement by deforming the holding portion.

Preferably the first connecting arrangement is configured for opening the other, second connecting arrangement. It is also preferable that the second connecting arrangement should be configured for opening the first connecting arrangement. Any step of the opening processes can be used for triggering, can come along with triggering or can automatically trigger the lighting element.

The connecting arrangements preferably are configured to produce the fluidic connection by mutual opening, the first connecting arrangement opening the second connecting arrangement and the second connecting arrangement opening the first connecting arrangement, thus producing the fluidic connection.

The connecting arrangements are preferably formed to be complementary and/or to correspond to one another, preferably such that the fluidic connection can—preferably only—be produced with connecting arrangements that fit one another.

The connecting arrangements are preferably fluidically sealed in each case in an initial state. This makes it possible to produce a mixture as required or on the spot, and to use containers which each comprise the respective connecting arrangements, but also to use them separately or independently of one another.

The connecting arrangement or arrangements is or are preferably designed for one-time and/or irreversible opening, particularly with or by means of the opening region or regions. An opening formed with or by means of or in the connecting system is thus preferably not reclosable.

An opening is unreclosable or is irreversibly openable in the sense of the present invention particularly when it can only be reclosed using special tools and/or by replacing defective parts or adding new parts. A destroyed sealing film as a preferred form of an opened opening region is preferably deemed to be unreclosable or irreversibly openable in the sense of the present invention even when the destroyed sealing film could theoretically be replaced and re-instated using corresponding equipment.

The proposed connecting system is hereinafter explained in more detail by reference to two connecting arrangements, the first connecting arrangement and the second connecting arrangement. This does not necessarily imply an opening sequence but serves primarily to differentiate the connecting arrangements. It is thus particularly possible to produce the second connecting arrangement separately and independently from the first connecting arrangement.

The connecting arrangements are preferably different and/or are configured differently for opening the other respective connecting arrangement. Thus, preferably, different mechanisms are used for opening the different connecting arrangements, or the connecting arrangements are designed for this purpose.

The embodiments may also be combined with one another, for example, by first opening the opening region of the first connecting arrangement with the second connecting arrangement by means of a severing element, then opening the second opening region of the second connecting arrangement by piercing the second opening region with the first connecting arrangement and subsequently further opening the opening region of the first connecting arrangement with the second connecting arrangement by deforming the first connecting arrangement with the second connecting arrangement. Each of these processes/steps might trigger the lighting element.

The connecting arrangements may also mutually pierce one another and/or one of the connecting arrangements may pierce the other connecting arrangement and the other connecting arrangement may open the one connecting arrangement by a deformation process. Each of these processes/steps might trigger the lighting element.

The proposed container system is particularly preferably used for the combined administration of medicaments. In particular, it is possible to store vaccines as contents which are not stable in the long term with one another in separate containers and to connect these containers fluidically by means of the proposed connecting system before use, thus enabling a rapid and efficient formation of a mixture, without affecting removal openings such as septa. Alternatively, the respective vaccines may also be used separately from one another through the removal openings, if no fluidic connection has been formed by means of the connecting system.

Containers or bottles and/or connecting arrangements in the sense of the present invention are preferably at least substantially dimensionally stable, rigid or semi-rigid and/or at least substantially formed from plastics material, or plastics material comprising, in particular, polyethylene, HD-PE, LD-PE or polypropylene.

A "bottle" in the sense of the present invention is preferably a closable container for transporting and storing fluids, particularly liquids, gases and pourable solids such as powders. A bottle in the sense of the present invention preferably has a diameter which is smaller than its height. A bottle in the sense of the present invention preferably has an at least substantially conically tapering end, also referred to as the neck of the bottle. The neck of the bottle preferably ends in an opening which is, in particular, round, closable and openable for the removal of its contents, also referred to as the removal opening. Bottles in the sense of the present invention are preferably narrow-necked bottles and/or vials. In narrow-necked bottles the diameter or the internal width of the removal opening is less than the average internal diameter of the storage space formed by the bottle, preferably less than 70%, particularly less than 50%. However, other solutions are also possible here.

A "connecting arrangement" in the sense of the present invention is preferably a device which is configured to provide the fluidic connection and, preferably, to provide a mechanical connection while forming the fluidic connection. In particular, it is a fluid coupling, a flange, a coupling member, an attachment member, a plug connection, a male and/or female connector, particularly a plug connector, or a part thereof.

A "connecting arrangement" in the sense of the present invention may be a portion/region of a container, particularly a bottle, or the connecting arrangement is (in each case)

connected to a container, particularly by material, frictional and/or interlocking connection. Particularly preferably the connecting arrangement is at least partially formed by or in one piece with the container or the bottle. Alternatively or additionally the connecting arrangement adjoins a container or a bottle or is otherwise suitable for fluidically attaching or connecting the interior of the container or the bottle.

A connecting arrangement is preferably "fluidically sealed", in the sense of the present invention, when the escape or passage of fluid, particularly liquid, is prevented or when a fluid or liquid barrier prevents the escape or passage of fluid, particularly liquid.

Connecting arrangements are "insertable in one another" in the sense of the present invention particularly when a part or portion of one of the connecting arrangements can be arranged inside the other connecting arrangement or a part or portion thereof. In particular, at least a portion of one of the connecting arrangements can be pushed, laid, inserted or otherwise introduced into the other or corresponding connecting arrangement. Connecting arrangements are inserted in one another particularly when they overlap radially at least partially, substantially or completely in relation to a (common) axis of symmetry and/or central axis, or an inner portion of the one connecting arrangement is (completely) surrounded or embraced (radially) by an outer portion of the other connecting arrangement.

An "axial movement" along a common axis in the sense of the present invention is preferably a movement which is non-helical, non-rotational, at least substantially or solely linear and/or solely axial and/or a movement which does not require a complete rotation or revolution. The connecting arrangements are preferably adapted to be fitted into one another, inserted in one another and/or fitted together in an at least substantially linear manner to produce the non-releasable and/or fluidic connection.

"Opening" in the sense of the present invention particularly denotes providing access to the interior of a container or a bottle or the volume contained by a container or bottle, by forming an opening, an orifice, a passage, a hole or the like, particularly so that a fluid, particularly a liquid, can enter and/or leave.

An "opening region" in the sense of the present invention is in particular a region which is configured for opening, i.e., is constructed so as to form an opening, an orifice, a passage, a hole or the like or fluidic access for the interior or for the volume contained by a container. The opening region is preferably fluidic ally closed and fluidically openable. It may be a closed off hole, a closed and openable wall orifice, a closed and openable passage, a closed and openable closure or the like.

A "film-like opening region" is preferably a portion which is particularly of thin-walled or flat construction to form an opening. A film-like opening region is preferably an opening/region which is sealed or closed off by a film, membrane, or other flat, thin, breakable and/or fragile structure.

"Pierceable" in the sense of the present invention is, in particular, a structure which can be broken through or perforated by means of an object, particularly a point, so that a connection can be made from one (flat) side to the opposite side. The piercing preferably produces an opening. In particular, a pierceable opening region is destroyed on piercing and permanently opened thereby.

"Sealing" in the sense of the present invention indicates in particular that the escape and/or ingress of substances is prevented by a barrier.

"Self-sealing" in the sense of the present invention denotes in particular that a sealing action is produced without separate aids, with intrinsic means and/or automatically, fully automatically, coincidentally or without the need for any separate steps.

"Sterile self-sealing" in the sense of the present invention denotes, in particular, self-sealing, thereby forming a barrier against the ingress of germs such as bacteria or viruses, so as to at least substantially prevent the ingress and/or escape of bacteria. In particular, the seal, the sealing clearance and/or contact pressure are designed so that any leaks that may potentially remain have a maximum cross section which blocks the passage of germs such as bacteria or viruses.

"Fluid-tight" in the sense of the present invention is in particular a seal which at least substantially prevents the entrance or exit of fluids, particularly liquids.

"Gas-tight" in the sense of the present invention is, in particular, a seal which at least substantially prevents the entrance or exit of gases.

A "material construction" in the sense of the present invention denotes in particular a composition and/or a structure and/or a morphology and/or an arrangement of different structures, different materials or the like.

A "laminar construction", also a sandwich construction, multi-layered construction, particularly a composite construction, a composite material and/or a laminated compound material in the sense of the present invention denotes in particular a structure comprising different layers which are preferably joined together and/or adjoining one another, can be logically sub-divided or delimited from one another, are arranged with their flat sides facing one another or arranged against one another, comprising flat elements or portions which can be differentiated by their physical or chemical properties.

"At the edges" in the sense of the present invention or an "edge portion" in the sense of the present invention is in particular a region spaced from a center, middle or center of gravity, or a region which has an edge, a margin, an end or a boundary, adjoins the latter or faces the latter. In particular, it is a portion of a preferably flat structure at its circumferential edge, in particular of an encircling or annular shape or the like.

A "central portion" in the sense of the present invention is, in particular, a portion at a spacing from an end, edge and/or margin, and/or comprises, encompasses or extends around a center, a middle point or center of gravity.

"Destroying the opening region" in the sense of the present invention denotes in particular the irreversible changing of the opening region, thereby impacting its previous function as a seal, wall, sealing member and/or closure or so that the previous function is no longer performed, particularly as a result of machining, shaping, deformation, tearing, separation or by some other method. The opening region may be opened and/or the fluidic connection may be produced thereby.

"Cutting through the opening region" in the sense of the present invention denotes in particular severing the material of the opening region from one side to another, particularly an opposite side, and/or dividing them and/or severing them by cutting, shearing, piercing or some other method.

"Remaining intact" in the sense of the present invention denotes in particular the maintenance of a previously existing function. An intact opening region has and retains, in particular, the function or functions of closing off, sealing and/or forming a barrier against the ingress and/or escape of germs, fluids, liquids, gases or the like.

A "fluid" for the purposes of the present invention is preferably a flowable substance. A fluid is particularly flowable such that it is able to pass through a fluidic connection. In particular, a fluid for the purposes of the present invention is a liquid, a suspension, a flowable solid, such as a powdered or granulated material, and/or a gas in liquid or gaseous form. Particularly preferably, at least one of the substances is liquid, particularly both or at least two substances.

A "fluidic connection" in the sense of the present invention is preferably an arrangement configured for the passage of a fluid, particularly a liquid, a gas or a flowable solid. In particular, it is a transit region, a passage or channel.

A "fluidic passage" in the sense of the present invention is in particular a means which is configured for the passage of a fluid, particularly a liquid, a gas or a flowable solid. In particular, it is a transit region, a connection or a channel which is preferably (tightly) sealed off from the environment or a side remote from the passage on a wall that forms the passage.

Preferably, an opening region in the sense of the present invention is "brittle" if, particularly on account of its composition and/or construction, it is suitable for and designed to tear close to its elastic limit without or with very little plastic deformation (brittle facture). In particular, the opening region has an elastic limit of less than 200 N/mm$^2$ and/or a tensile strength of less than 100 N/mm$^2$, preferably less than 60 N/mm$^2$ and/or a quotient of elastic limit and tensile strength of less than 1, preferably less than 0.7 or 0.5. This can be achieved in particular by structuring and/or combining, joining or laminating different materials. The opening region may be formed by a laminate of several films, of which preferably one film contains aluminum or consists of aluminum or is metallic. Particularly preferably, the opening region is at least partly metallic. Preferably, the opening region is formed with or from a composite material which preferably has a preferably flat or film-like layer of aluminum.

An "unstable opening region" in the sense of the present invention is preferably a region which is mechanically less stable than the parts surrounding it and/or which can be destroyed manually or by the application of force, particularly in the manner of a frangible point.

"Outside the opening region" in the sense of the present invention means that this is a region or portion which is separate from the opening region but is preferably directly or indirectly adjacent to the opening region, particularly such that deformation in this region causes stretching of the opening region.

"Deformable" in the sense of the present invention is preferably elastic or plastic deformability. The connecting arrangement(s) or mouth-shaped portions are preferably elastically deformable, thus causing plastic/irreversible deformation of the opening region. The connecting arrangement(s) or mouth-shaped portions may, however, also be plastically deformed/deformable.

Parts or portions are said to "corresponding to one another" in the sense of the present invention particularly when they are of similar and/or complementary construction to one another, when they fit into one another, resemble one another, are arranged similarly, have similarly oriented structures of similar shape and/or are configured to interact with one another in order to produce a function or effect.

"Rotating relative to one another" in the sense of the present invention denotes in particular a rotary movement of a part, preferably a connecting arrangement or a container or a bottle with a connecting arrangement, relative to another part, preferably another connecting arrangement or another container or another bottle.

"Rotating relative to one another" in the sense of the present invention denotes in particular a rotary movement of two parts, preferably a connecting arrangement or a container or a bottle with a connecting arrangement, relative to another part, preferably another connecting arrangement or another container or another bottle, preferably in different or opposite directions of rotation.

A "mouth-shaped portion" in the sense of the present invention is in particular a portion or part which comprises or forms an opening, an opening edge, a mouth or a neck, preferably with an opening at its end, or some other tubular portion or a passage with a radially surrounding wall which terminates in an opening, which is preferably open at its end and/or forms an opening at at least one end.

In the sense of the present invention the term "thin walled" denotes in particular a structure which is flat or planar in cross section with a wall thickness on average less than 2 mm, 1.5 mm, 1 mm and/or less than 0.5 mm or 0.3 mm, particularly preferably less than 200 µm, particularly less than 150 µm.

A "closure device" in the sense of the present invention is preferably a part of, or at least substantially forms, an opening region. The closure device here is, in particular, a flat or planar arrangement or closure plate. Thus, a closure device has, in particular, a material thickness that exceeds its longitudinal extent, preferably by a factor of at least 2, 3, 4 or 5.

The closure device is preferably formed in one piece, particularly in one piece with the frangible point, particularly the thin point. The closure device together with the frangible point may form an opening region or a part thereof. Preferably, the frangible point forms the film-like, brittle and/or unstable part of the opening region or renders the opening region film-like, brittle and/or unstable. For this reason, the frangible point is preferably sufficiently fragile to form an opening by tearing under mechanical load.

The connecting arrangement is preferably formed from plastics, particularly a thermoplastic material, particularly by injection molding. The opening region is preferably predominantly formed by the closure device, particularly over more than 70%, 80%, 90% or 95% of its area. Thus, compared with the surface area of the closure device, the frangible point takes up an area of less than 10%, particularly less than 5%.

The closure device may be S-shaped in cross-section longitudinally of the main dimension. The closure device may have ribs or other reinforcing elements to stiffen it. The closure device is preferably sufficiently stable or rigid that it cannot be deformed, or can only be deformed to an insignificant degree, by the frangible point. The result of this is that a force acting on the frangible point does not deform the closure device or deforms it only insignificantly, particularly by compression, thus ensuring that the frangible point breaks or tears more easily.

A "frangible point", particularly a thin point, in the sense of the present invention is preferably a film-like, brittle and/or instable or fragile area or opening region or a film-like, brittle and/or unstable or fragile part of the opening region. The frangible point can be a predetermined breaking point. It is not limit to a point but can also be a frangible line, frangible area, predetermined breaking line and/or predetermined breaking area.

The frangible point is preferably embodied and designed to be broken or torn by mechanical stress in order to form an opening. In particular, the frangible point interacts with the closure device, while the frangible point can be tensioned relative to the closure device in such a way that the resulting tensions, shear forces and the like lead to breakage of the frangible point. The frangible point thus is or forms, in particular, a weakened point or a portion with a mechanically weakened structure compared with surrounding or adjacent areas.

The frangible point is preferably provided completely or partly circumferentially at or within the mouth-shaped portion or holding portion. The frangible point may be in the shape of a bead or web. In particular, the frangible point forms a connecting strip to the closure device, particularly from the holding portion or mouth-shaped portion.

A "chamber" in the sense of the present invention is preferably a structure or volume which is tightly sealed or sealable in all directions. The chamber may, however, be openable in principle, for example by a connecting arrangement or by opening a sealing arrangement or the like.

A "volume" or "volume formed" in the sense of the present invention preferably denotes a region or a (partial) chamber which is at least substantially or entirely surrounded. The term "volume" may thus be replaced by the term chamber or partial chamber, if required. Moreover, a distinction is made between an inner volume and an outer volume; preferably, this is functionally intended to convey that the inner volume can be reached by passing through the outer volume. Preferably, the outer volume surrounds the inner volume. However, this is not absolutely essential, as in other embodiments the outer volume may form an antechamber to the inner volume. Preferably, the outer volume forms an outwardly sealed antechamber, while the inner volume is adjacent to the outer volume and is sealed off from it, so that the outer volume shields the inner volume from the environment.

A "container blank" in the sense of the present invention is preferably a tubular structure with at least two openings, one opening being or forming a removal opening for later opening and/or closing or filling and/or removal. Another opening is of a temporary nature and is sealed off during the manufacturing process of the container, particularly preferably by the leaktight use or incorporation of a connecting arrangement. The connecting arrangement as such can then form part of the container and enable later opening of the container in the region.

A "container blank" in the sense of the present invention comprises the opening for the insertion or fitting of a connecting arrangement, preferably on a side which is opposite or remote from the removal opening. However, other solutions are also possible. In addition, a container blank may also comprise only one opening for insertion or fitting of the connecting arrangement. In this case, the container obtained after assembly has only one opening in the form of the opening region of the connecting arrangement. The container blank preferably comprises a bottle-like site which has an at least substantially conically tapering portion or shoulder region which transitions into a bottle neck. The bottle neck then preferably forms, or comprises, the removal opening.

A "sealing portion" in the sense of the present invention is preferably a region which is configured and/or arranged for sealing abutment. In particular, it is a sealing lip, a sealing strip or the like. A sealing portion may comprise a sealing surface which is formed by a surface region of the sealing portion and provides the direct sealing effect. In particular, a sealing effect is achieved by means of sealing surfaces bearing directly on one another. For this purpose, the sealing surfaces preferably bear on one another under tension or pressure, for example in the form of a press fit or the like. The sealing surfaces are preferably formed by the material of the sealing portion or the surface of the sealing portion. However, there are also other possibilities, for example using seals in the region of the sealing portion.

A "support portion" in the sense of the present invention preferably interacts with an opening region or a frangible point such that opening of the opening region or breaking or tearing of the frangible point, by mixed-mechanical support, support from below, particularly acting as a bearing or counter-bearing, is avoided. In particular, this is thus a device which diverts or keeps mechanical stress away from fragile, unstable areas, so as to impede or prevent accidental opening. The support portion is particularly configured to relieve stress from the frangible point.

A "securing device" in the sense of the present invention is preferably a means for preventing movements, particularly relative movements of connecting arrangements and/or containers, or other actuations which would or could lead to the opening of an opening region. In particular, it is a securing ring or the like, for blocking a, preferably axial, movement of connecting arrangements to one another and to enable such movement during actuation or removal. The securing device preferably comprises a blocking part which, as a working part or working portion of the securing device, is directly responsible for a blockade, particularly of a movement, being implemented or removed.

A "guide device" in the sense of the present invention is preferably a mechanism or a part thereof which guides a relative movement of connecting arrangements to one another, particularly bayonet-like. This preferably enables a bayonet connection to be obtained. A bayonet connection, also known as a bayonet closure, preferably is a mechanical connection of two at least substantially cylindrical and/or rotationally symmetrical parts, particularly rotationally symmetrical with respect to a central axis or axis of symmetry.

The connection is produced by means of the guide devices by a pushing in and turning movement. Parts are inserted axially in one another and after being pushed in axially until they reach a stop they are rotated relative to one another, thus producing an interlockingly engaging blockade in the axial direction. This preferably produces the fluidic connection.

A "first guide device" for this purpose is preferably a slot, a groove or other guide device with an at least substantially right-angled configuration, beginning with a part that extends axially or parallel to the central axis or axis of symmetry, and an adjoining part which extends at least substantially at right-angles to the previous direction. The portion that follows the axially extending portion thus extends preferably at least substantially in a plane perpendicular to the central axis or axis of symmetry. Another or second guide device, and/or guide device corresponding to the first, is preferably a button, peg, strip or other part corresponding to the other guide device, thus corresponding particularly to the groove, slot or the like. Overall, the guide devices thus preferably form a sliding guide.

The containers are preferably produced separately from one another for the provision of the fluidic connection. This enables them to be universally applicable.

In the following specification and claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event, structure, or circumstance may or may not occur, and that the description includes instances where the event, structure or circumstance occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Various embodiments of the disclosure are discussed throughout this application. Any embodiment discussed with respect to one aspect of the disclosure applies to other aspects of the disclosure as well, and vice versa. Each embodiment described herein is understood to be embodiments of the disclosure that are applicable to all aspects of the disclosure. It is contemplated that any embodiment discussed herein can be implemented with respect to any method or composition of the disclosure, and vice versa.

Unless defined herein and below in the remainder of the specification, all technical and scientific terms used herein have the same meaning as commonly understood by one of ordinary skill in the art to which the disclosure pertains.

The term "animal" as used herein refers to any animal which is the subject of a medical treatment for a medical condition unless stated otherwise. In some instances the medical treatment may be prophylactic instead of reactive (e.g., a vaccine to prevent a medical condition rather than a medication to treat an already existing medical condition). It is understood that at least domestic animals, farm animals, zoo animals, sport animals and pet animals are within the scope of the meaning of the term. Desirably, the animal is a farm animal. Examples of farm animals include, but are not limited to, horses, cows, pigs, buffalo, bison, oxen, chickens, goats, sheep, donkeys, alpacas, llamas, rabbits, dogs, cats, ducks, and turkeys.

The terms "medicament", "medication", and "medicine" are used interchangeably herein and describe a pharmaceutical composition or product intended for the treatment or prevention of a medical condition having at least one symptom. The pharmaceutical composition or product will have a physiological effect on the animal when it is introduced into the body of an animal. The pharmaceutical composition or product can be in any suitable formulation unless a specific formulation type is required or disclosed.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity "Immunogenic" means evoking an immune or antigenic response. Thus an immunogenic composition would be any composition that induces an immune response.

"Therapeutically effective amount" refers to an amount of an antigen or vaccine that would induce an immune response in a subject receiving the antigen or vaccine which is adequate in preventing or reducing the clinical signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

An "immunogenic or immunological composition" and/or "vaccine" preferably refers to a composition of matter that comprises at least one veterinary antigen and/or immunogenic portions thereof that elicit an immunological response in the host of a cellular or antibody-mediated immune response to the composition. In some desirable embodiments, an immunogenic composition induces an immune response and, more desirably, confers protective immunity against one or more of the clinical signs of at least one veterinary antigen.

The terms "vaccination" or "vaccinating" or variants thereof, as used herein means, but is not limited to, a process which includes the administration of a vaccine and/or an immunogenic composition that, when administered to an animal, elicits, or is able to elicit—directly or indirectly—, an immune response in the animal against at least one veterinary infectious disease.

As used herein, the term "viable" or any variants thereof, when used in reference to a medicament preferably means that the medicament when administered to a patient in need thereof produce an immune response in said patient. It does not require that the immune response be the maximum possible or therapeutically effective. Both humoral and cell-mediated immune response are covered, and a viable medicament may produce either a humoral immune response, a cell-mediated immune response or both. If the medicament is a vaccine or immunogenic composition, the immune response may be partial or complete protection from the medical condition, and the protection may be permanent or temporary.

The light member as discussed further herein may use both fluorescence and/or chemiluminescence. Both result from the decay of a molecule in a higher energy or excited state back down to the ground state. This decay results in the release of energy and the emission of a photon; however, they are caused by different phenomenon. Fluorescence results from electronic excitation—a consequence of the molecule absorbing a photon initially. That is, a photon of light is absorbed and re-emitted. The same color may or may not be re-emitted as the molecule can lose energy, while in the excited state, through vibrational deactivation.

Chemiluminescence is caused by a molecular reaction of two (or more) ground state molecules producing a final molecule in an excited state. The energy in the reactants is translated into the products and, while forming the products, it also excites them. This excitation may lead to chemiluminescence. Some reactions also result in the formation of molecules in an excited state that result in the emission of a photon of light.

As a non-limiting example of chemiluminescence, Glow Sticks® emit light in any of various different colors based on the combination of three different chemicals: diphenyl oxalate, hydrogen peroxide and a fluorescent dye according to the following reaction:

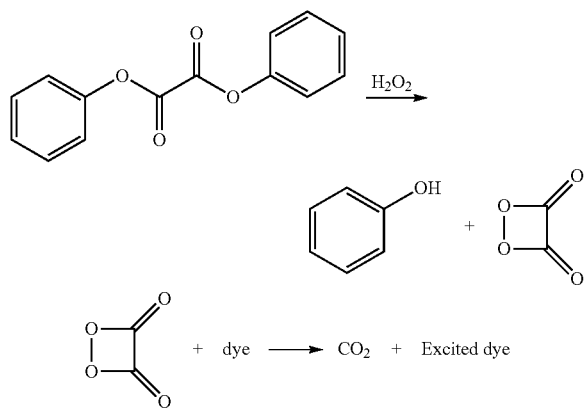

The selection of the fluorescent dye determines the color of the excited dye which is the source of the light emission observed by the end-user. Non-limiting examples of fluorescent dyes are rhodamine B (red), 5,12-bis(phenylethynyl) naphthacene (orange), rubrene (yellow), 9,10-bis(phenylethynyl)anthracene (green), and 9,10-diphenylanthracene (blue). In the initial structural arrangement, the hydrogen peroxide is physically separated from the diphenyl oxalate and dye. Upon the application of force to the Glow Stick (i.e., bending it which ruptures the separator), the diphenyl oxalate and dye mix with the hydrogen peroxide thereby initiating a cascade which ultimately leads to the excitation of the dye, thereby causing the emission of light. Other chemiluminescent reactions are known in the art and that emit light as required in the embodiments disclosed herein are acceptable.

Alternatively, the light source of the light member may be generated by a light emitting diode (LED). An LED is a semiconductor device that emits visible light, usually monochromatic, when an electric current passes through it. In such a configuration, the light member comprising the LED would have an actuation switch that includes at least two different actuation settings such that the LED could be turned on and off. In some embodiments, the light member using an LED would be removable from the package and transferable to another package. In some other embodiments, the light member using an LED would be single use and disposed after use.

In another embodiment, the emission of light is actuated by removal of a separator that prevents two or more chemical from mixing. Upon removal, the chemicals mix thereby causing a chemical reaction that emits light.

The color of the light emitted from the light member is not limited and may be selected from any color visible to the human eye. Examples include, but are not limited to, white, red, orange, yellow, green, blue, indigo and violet. Different shades and intensities are also not limited. In some embodiments, the color is desirably yellow or white. They are selected based on the desired characteristics of the light member. Additionally, more than one color may be emitted from a light member over time.

In another embodiment, the light emitted by a chemical reaction may be one color, but the packaging structure or exterior containment comprising the chemicals may be a different color thereby exhibiting a different color to the end-user. As a non-limiting example, a chemiluminescent reaction that emits white light can be encased in a plastic structure where the exterior of that plastic structure is green. The end user would see a green light rather than a white one. The color of the structure that encases the chemicals is not limited and may be selected as desired by the manufacturer of the package. As one non-limiting example, some manufactures have trademarks that comprise a specific color or combination of colors. The color of the encasement of the chemicals could be matched to that color or combination of colors thereby enhancing brand recognition.

Regardless of the source of the light, fluorescence, chemiluminescence or an LED, they are observationally identical—visible light is emitted that is observed by an end-user. Additionally, because fluorescence and chemiluminescence are so similar in their source and often confused for one another, these two terms are used interchangeably. The embodiments disclosed herein are related to the outwardly observed visual effect rather than the cause of that effect.

The aspects of the present invention mentioned above and described in the following specific description may also be implemented and advantageous individually and in various combinations.

Further details, advantages and properties of the present invention will become apparent from the following description of preferred embodiments with reference to the accompanying drawings.

DETAILED DESCRIPTION OF THE INVENTION

Figure 1:
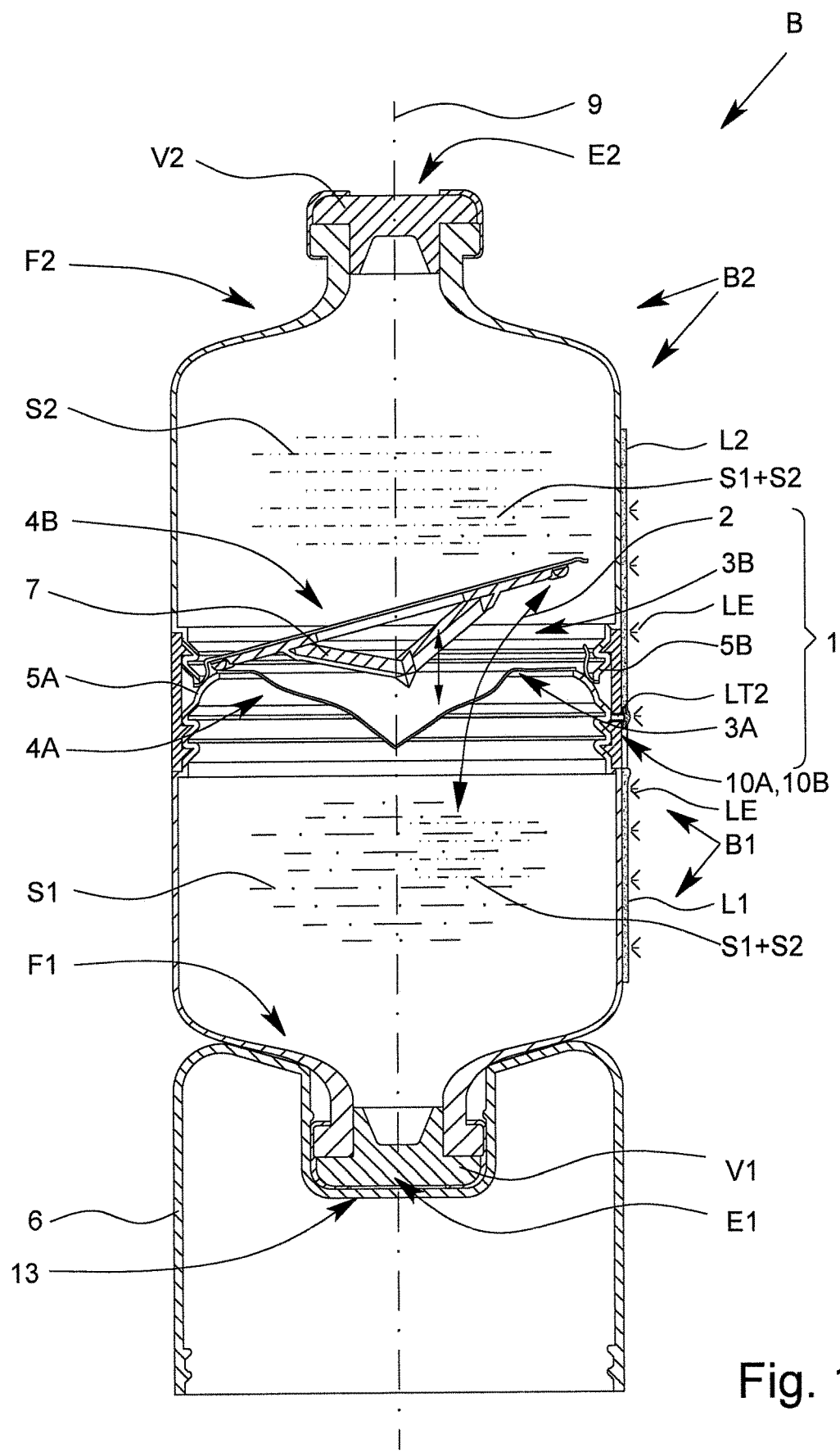
FIG. 1 shows a longitudinal section through a container system with the proposed connecting system and with the fluidic connection made.

In the following description of preferred embodiments by reference to the drawings, the same or corresponding reference numerals (with or without an apostrophe) have been used for the same or similar components or parts, where similar or identical advantages and properties may be achieved even if the associated description has not been repeated.

FIG. 1 shows in schematic section a proposed container system B with a first container B1 and a second container B2.

The container system B preferably comprises a proposed connecting system 1. The connecting system 1 is preferably configured to produce a fluidic connection 2, preferably between the first container B1 and the second container B2 of the container system B.

The connecting system 1 preferably comprises a number of connecting arrangements 3A, 3B, particularly a first connecting arrangement 3A which is associated with a first container B1 of the container system B and/or a second connecting arrangement 3B which is associated with the second container B2 of the container system B. Preferably, the first container B1 comprises the first connecting arrangement 3A and the second container B2 comprises the second connecting arrangement 3B or vice-versa.

The containers B1, B2 are preferably used for storing substances S1, S2, particularly for storing a first fluid and a second fluid and/or different vaccines. In particular, the containers B1, B2 are wholly or partly filled with one or more different substances S1, S2 or vaccines. Alternatively, or additionally the container or containers B1, B2 may also hold and/or store other substances S1, S2, preferably a solid. It is possible for only one substance S1, S2 to be a fluid, particularly a liquid. The fluid substance S1, S2 may be configured to form a solution or a suspension with the other substance S1, S2.

The proposed container system B is preferably used to prepare a medicament, particularly a combined medicament, combined vaccine or the like. However, there are other possible and advantageous applications for the proposed container system B.

Preferably, the first container B1 comprises a removal opening E1 and/or the second container B2 comprises a removal opening E2. Particularly preferably, both or at least two containers B1, B2 of the proposed container system B each comprise a removal opening E1, E2.

A removal opening E1, E2 in the sense of the present invention is preferably configured to dispense or to make it possible to remove the contents of the respective container B1, B2.

At least one and preferably several or all of the removal openings E1, E2 are preferably repeatedly useable, utilizable several times, re-sealable, re-usable and/or comprise a closure element V1, V2 which preferably allows opening and closing for the purpose of stepwise removal. This may be achieved by means of a septum.

Preferably, the removal openings E1, E2 are closed or closable and/or are primary means for removing substance S1, S2 from the containers B1, B2.

In the embodiment shown, preferably at least one of the removal openings E1, E2 and particularly both removal openings E1, E2 are closed off by so-called septa. A septum is a device with a rubber-like closure element V1, V2, particularly a rubber stopper or injection stopper, which is suitable for piercing by means of an injection needle for removal of its contents, the septum automatically closing the (respective) removal opening E1, E2 by elastic resilience after the injection needle has been removed. A septum, also referred to as a piercing membrane, preferably has a thin area, particularly in the center, this thin area being suitable for piercing in order to take up injection liquid using an injection needle. The injection stopper or the septum is preferably secured to the neck of the bottle or the removal opening E1, E2 by means of a flanged cap, preferably made of aluminum.

Preferably, one, both or all the containers B1, B2 are (each) injection ampoules or vials, for example, so-called multi-dose containers, particularly for vaccinating a number of animals with one dose each.

In the containers B1, B2, substances S1, S2 in the form of powdered medicaments, solutions or suspensions or vaccines may be transferred in this form.

The containers B1, B2 may (each) have a capacity of more than 10 ml, preferably more than 50 ml, 100 ml or 200 ml and/or less than 2 liters, preferably less than 1.5 liters or 1 liter, particularly less than 750 ml (each or after connection).

As shown in FIG. 1, the closure element V1, V2 is preferably sealingly connected to the respective removal opening E1, E2, preferably pressed on, particularly by means of a pressing ring or compression ring or a flanged cap. However, other solutions are also possible here, for example an adhesive bond, welded joint, a connection produced by injection molding or the like.

It is certainly preferable that the containers B1, B2 of the proposed container system B should each have a removal opening E1, E2, but not all the containers B1, B2 of the container system B must have a removal opening E1, E2.

Advantageously, the use of removal openings E1, E2 on a number of containers B1, B2 makes it possible to use the respective substance S1, S2 from the respective container B1, B2 independently of the use of the connecting system 1. Advantageously, the container system B therefore allows both separate use of the containers B1, B2 and also their use in conjunction with the fluidic connection 2 provided by the connecting system 1.

The containers B1, B2 are preferably fluidically connectable to one another so that the fluidic connection 2 between the volumes formed or held by the containers B1, B2 results in a joint interior being formed by the containers B1, B2 connected by the connecting system 1. The joint interior is particularly characterized in that the continuous fluidic connection 2 has a hydraulic cross section of more than 2 square millimeters, preferably more than 5 or 10 square millimeters, particularly more than 1, 2 or 3 square centimeters, or there is no constriction between the containers B1, B2, once the fluidic connection 2 has been made, which falls below such a hydraulic cross section or wherein the fluidic connection 2 has at least such a hydraulic cross section.

The container or containers B1, B2 is or are preferably configured as bottles. Particularly preferably, the containers B1, B2 (each) comprise a bottle neck F1, F2 which forms the removal openings E1, E2 or is adjacent thereto. A bottle neck F1, F2 may, starting from a terminal edge or mouth of the removal opening E1, E2, encompass an enlargement of the (hydraulic) cross section by more than a factor 1.5, particularly by more than a factor 2 or 2.5. However, the removal openings E1, E2 may also be differently constructed.

The containers B1, B2 preferably comprise the removal opening E1, E2 and the connecting arrangement 3A, 3B at different, opposite, diametrically opposed sides, ends, axial ends and/or in the neck region on the one hand and in the base region on the other hand. In particular, the removal opening E1, E2 is formed by the bottle neck F1, F2 and the connecting arrangement 3A, 3B is provided in the base region or at the opposite end from the bottle neck F1, F2. This has proved advantageous as it ensures that, when the connecting arrangements 3A, 3B are used, the removal opening(s) E1, E2 remain(s) accessible and unaffected in its (their) function.

The connecting arrangements 3A, 3B are preferably not intended for removal but for a one-time or irreversible provision of a durable fluidic connection 2, or are not reclosable.

The present invention is explained by means of the particularly preferred use for connecting to containers B1, B2, particularly bottles. However, it is possible and advantageous to use the proposed connecting system 1 in other areas as well, for example for fluidically connecting a container B1, B2 to other systems, for example for the rapid removal of the substance S1, S2.

Figure 2:
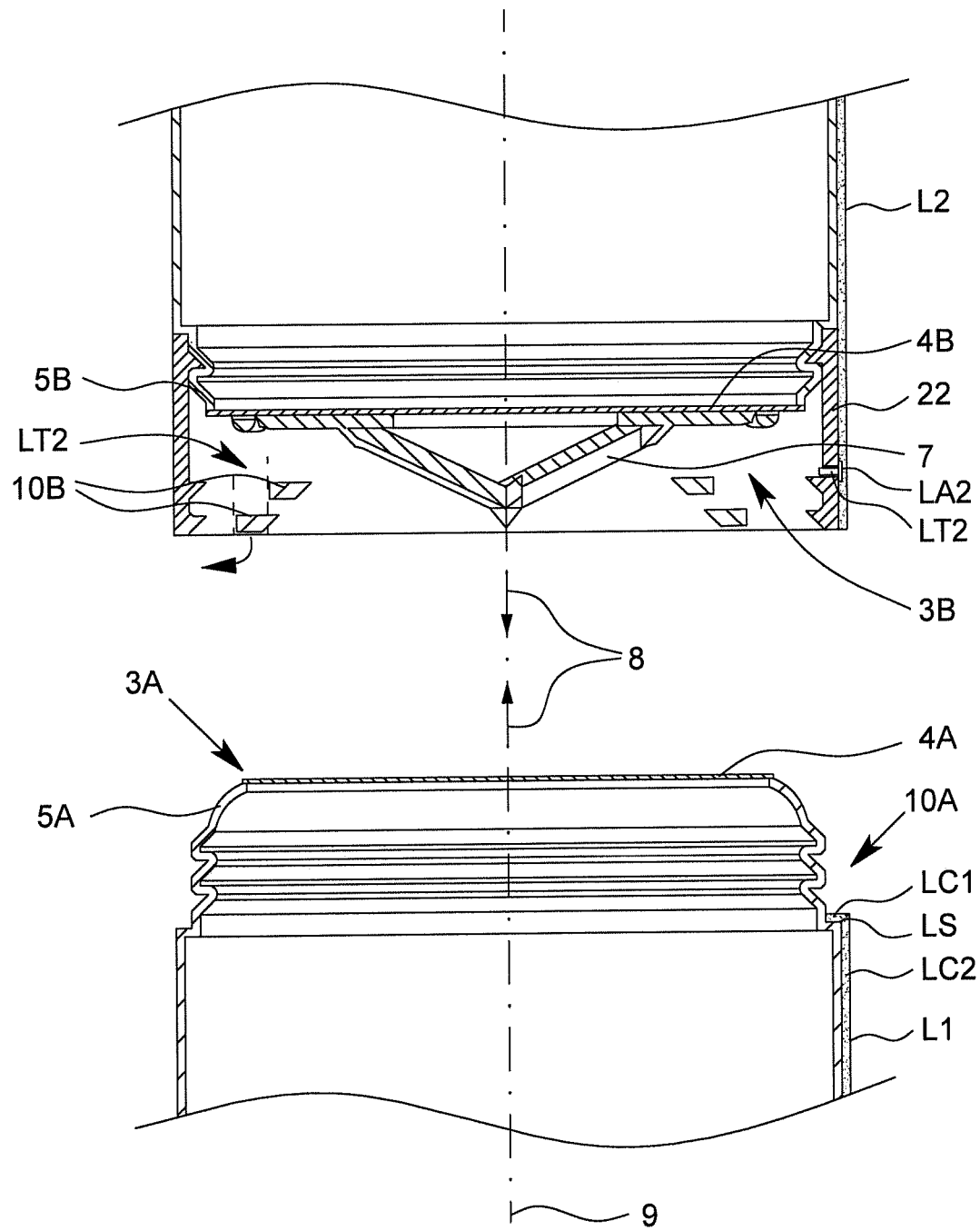
FIG. 2 shows a longitudinal section through the proposed connecting system in a first embodiment in a starting position.

FIG. 2 shows in longitudinal section a proposed connecting system 1 according to the first embodiment in a starting position or in the unconnected state.

Figure 3:
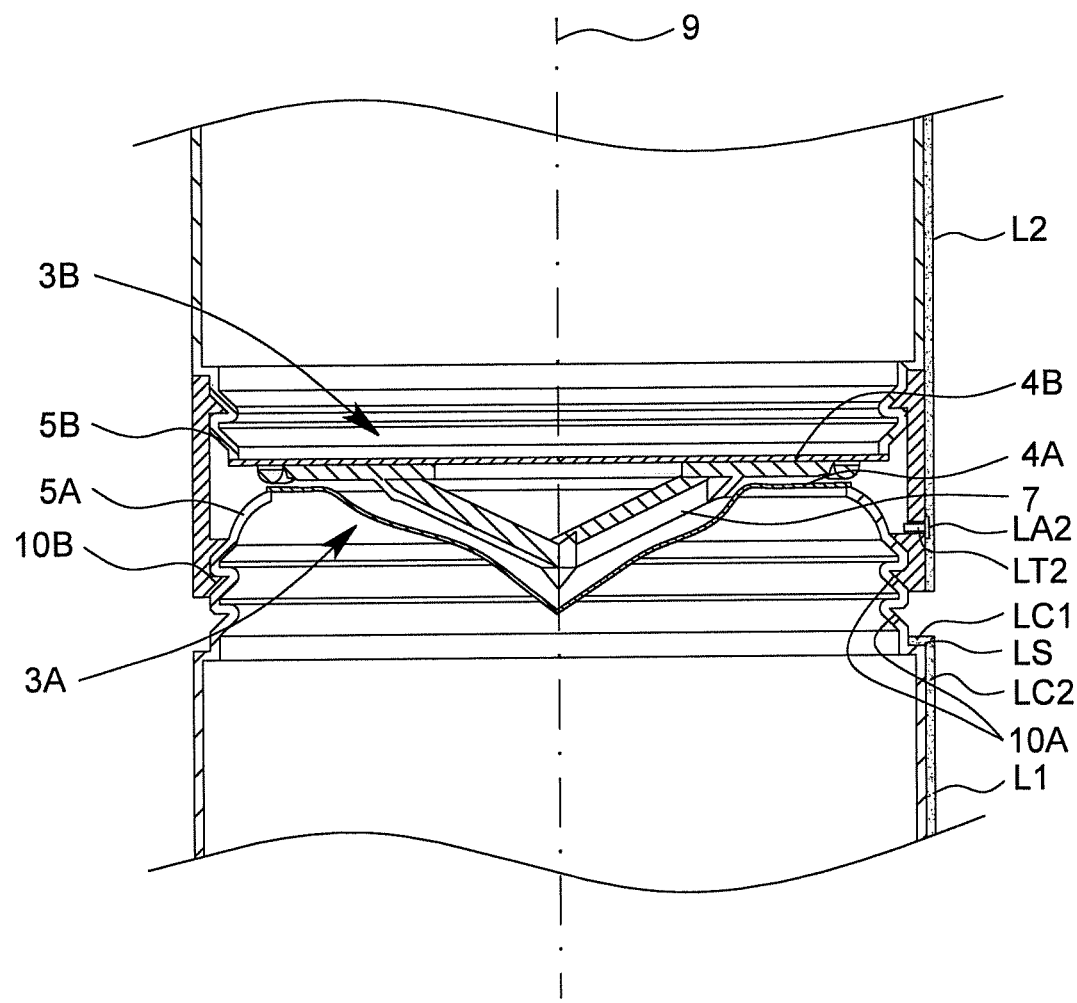
FIG. 3 shows a longitudinal section through the proposed connecting system of the first embodiment in a first connecting position.

FIG. 3 shows in longitudinal section the proposed connecting system 1 according to the first embodiment in a first connecting position in which preferably the fluidic connection has not yet been made but one of the opening regions 4A, 4B has already been opened.

Figure 4:
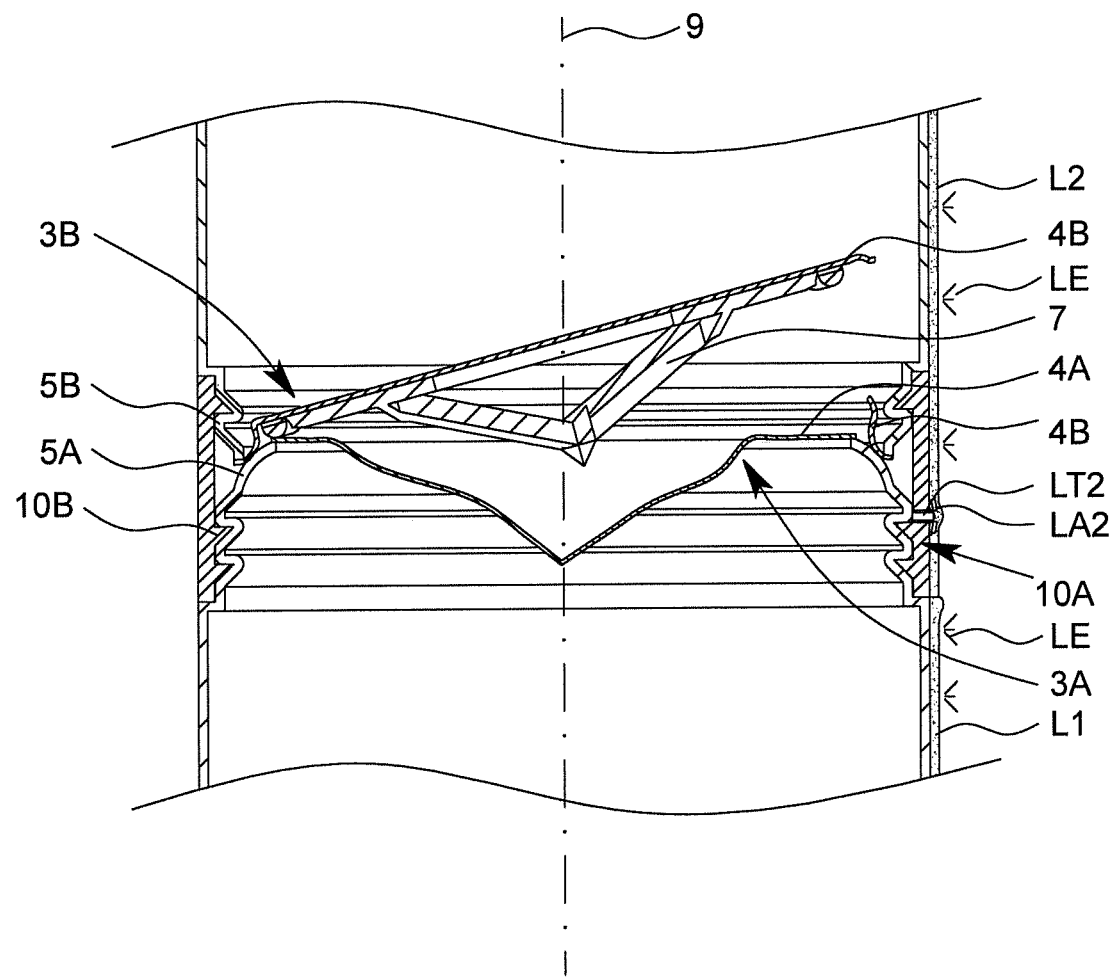
FIG. 4 shows a longitudinal section through a proposed connecting system of the first embodiment in a second connecting position.

FIG. 4 shows in longitudinal section a proposed connecting system 1 according to the first embodiment in a second connection position in which a fluidic connection 2 is produced. This is the position which is also shown in FIG. 1.

The proposed connecting system 1 preferably comprises a plurality of connecting arrangements 3A, 3B, particularly preferably at least the first connecting arrangement 3A and the second connecting arrangement 3B, which are preferably configured to be at least partially complementary to one another or corresponding to one another.

The first connecting arrangement 3A preferably comprises an opening region 4A. The second connecting arrangement 3B preferably comprises an opening region 4B.

Preferably, the containers B1, B2 comprise the opening regions 4A, 4B or the opening regions 4A, 4B form a part of the respective connecting arrangement 3A, 3B which is associated with the respective container B1, B2 or forms a part thereof.

Preferably, one or both opening regions, 4A, 4B are regions or portions of the respective connecting arrangement 3A, 3B which are configured to produce the fluidic connection 2 (durably and/or irreversibly), particularly by (irreversible) destruction thereof. For this purpose the opening region or regions 4A, 4B may have a (mechanical) weakened area or frangible point or may be configured as a weakened area or frangible point. The opening regions 4A, 4B, may be identical, similar or different in construction, particularly with respect to the reduced material and/or the shape of the opening regions 4A, 4B.

In particular, the opening regions 4A, 4B are configured to be (mechanically) destroyed or pierced in order to provide the fluidic connection 2. For this purpose an opening region 4A, 4B according to the present invention may be configured to be destroyed, perforated and/or torn open under mechanical load in order to enable or produce the fluidic connection 2.

In the embodiment shown, the opening regions 4A, 4B are formed by film-like or membrane-like wall portions of the respective connecting arrangement 3A, 3B. In particular, one or more of the opening regions 4A, 4B is or are sealing films. In principle, the opening regions 4A, 4B may, however, be formed by weakening the material that forms the respective connecting arrangement 3A, 3B and/or may be formed in one piece with the respective connecting arrangement 3A, 3B.

The opening region or regions 4A, 4B are preferably configured to tear when mechanically stressed and thereby produce the fluidic connection 2. Preferably, the opening regions 4A, 4B have a material with a modulus of elasticity of more than 2000 N/mm$^2$, preferably more than 4000 N/mm$^2$, particularly more than 6000 N/mm$^2$. Alternatively or additionally, the opening regions 4A, 4B may have a tensile strength of less than 100 N/mm$^2$, preferably less than 80 N/mm$^2$, more particularly less than 60 N/mm$^2$. The modulus of elasticity and the tensile strength may be determined according to EN ISO 6892-1, ISO 6892, ASTM E 8, ASTM E 21, DIN 50154, DIN 50125 and/or ISO 527, ASTM D 638.

It is also preferable that the opening region or regions should have a material thickness of less than 100 µm, preferably less than 70 µm, particularly less than 50 µm and/or more than 5 µm, particularly more than 10 µm.

The first connecting arrangement 3A, 3A' preferably comprises the first, particularly film-like, opening regions 4A, 4A' and/or the second connecting arrangement 3B, 3B' preferably comprises a second, particularly film-like opening region 4B, 4B'. Advantageously, this simultaneously ensures secure closure 14 of the respective connecting arrangements 3A, 3A', 3B, 3B' and reliable and simple opening of the respective opening regions 4A, 4A', 4B, 4B'.

The first connecting arrangement 3A, 3A' is preferably configured to open the second connecting arrangement 3B, 3B' by piercing or destroying the second opening region 4B, 4B'. Alternatively, or additionally the second connecting arrangement 3B, 3B' is preferably configured to open the first connecting arrangement 3A, 3N by piercing or destroying the first opening region 4A, 4A'. Advantageously, the fluidic connection 2 may thus be produced manually or without the use of tools. The interiors of the containers B1, B2, B3 are preferably connectable by means of the connecting arrangements 3A, 3N, 3B, 3B' without any further aids or tools.

Preferably, to produce the fluidic connection 2, the opening region 4A, 4A', 4B, 4B' of the second connecting arrangement 4B, 4B' may be pierced with the first connecting arrangement 4A, 4A' and preferably the first opening region 4A, 4A' of the first connecting arrangement 3A, 3A' may be pierced with the second connecting arrangement 3B, 3B', particularly a severing element 7 thereof. The fluidic connection 2 may thus be produced by mutual perforation or piercing.

The connecting arrangements 3A, 3A', 3B, 3B' preferably have mouth-shaped portions 5A, 5A', 5B, 5B', which are formed such that the mouth-shaped portion 5A, 5A', 5B, 5B' of one of the first and second connecting arrangements 3A, 3A', 3B, 3B' may be aligned with the mouth-shaped portion 5A, 5A', 5B, 5B' of the other one of the first and second connecting arrangements 3A, 3N, 3B, 3B', so that preferably the opening region 4A, 4A', 4B, 4B' of the other one of the first and second connecting arrangements 3A, 3N, 3B, 3B' can be pierced and/or the other one of the first and second connecting arrangements 3A, 3A', 3B, 3B' can be opened.

The opening region 4A preferably comprises the mouth-shaped portion 5A and/or the opening region 4B comprises the mouth-shaped portion 5B. The mouth-shaped portions 5A, 5B preferably delimit the opening regions 4A, 4B. The mouth-shaped portions 5A, 5B may be formed in one piece with and/or as a wall portion of the respective connecting arrangement 4A, 4B. Preferably, the mouth-shaped portions 5A, 5B have open edges or are formed in the shape of collars or necks, the respective opening region 4A, 4B preferably being surrounded or delimited by the respective mouth-shaped portions 5A, 5B. The mouth-shaped portions 5A, 5B or the open edges thereof preferably adjoin the opening regions 4A, 4B or delimit them, or vice-versa. Particularly preferably, an open edge of the respective mouth-shaped portion 5A, 5B forms a (circumferential) fixing portion for an opening region 4A, 4B which is more particularly film-like or formed by a film.

The container system B, in another aspect of the present invention which may also be implemented independently, comprises a cover device 6 which is configured to hold one of the containers B1, B2, particularly to act as a foot for it. Advantageously, the cover device 6 may alternatively or additionally serve for, particularly sterile, covering of one of the containers B1, B2 and/or one of the connecting arrangements 3A, 3B. This aspect will be discussed in more detail hereinafter.

The connecting arrangement 3A, 3B and the method for producing the fluidic connection therewith is explained in more detail hereinafter in a first embodiment illustrated in FIGS. 2 to 5.

In the first embodiment, the first connecting arrangement 3A is configured for opening the opening region 4B of the second connecting arrangement 3B. It is particularly preferable that the mouth-shaped portion 5A of the first connecting arrangement 3A should be adapted to be inserted or pushed into the mouth-shaped portion 5B of the connecting arrangement 3B such that during the insertion or introduction the opening region 4B of the second connecting arrangement 3B is opened.

In the embodiment shown, the first connecting arrangement 3A, 3A' or the first mouth-shaped portion 5A, 5A' is a preferably male coupling element and/or the second connecting arrangement 3B, 3B' or the second mouth-shaped portion 5B, 5B' is a, preferably female, coupling element, particularly forming a fluid coupling.

In particular, it is provided that one end or an open edge of the mouth-shaped portion 5A has an outer circumferential edge which can be arranged inside an inner circumferential edge of the mouth-shaped portion 5B.

Preferably, the outer circumferential edge of the mouth-shaped portion 5A of the first connecting arrangement 3A corresponds to the inner circumferential edge of the mouth-shaped portion 5B of the second connecting arrangement 3B or resembles it, or vice versa. In particular, the mouth-shaped portion 5A of the first connecting arrangement 3A comprises, at least laterally or at a transition to the opening region 5A, an external diameter which is less than an internal diameter of the mouth-shaped portion 5B of the second connecting arrangement 3B, preferably at least at a terminal edge or at a transition to the opening region 5B. In the embodiment shown in FIGS. 2 to 5, the mouth-shaped portion 5A, 5B is preferably neck-shaped and/or at least substantially round in cross section.

Unless otherwise stated, the term cross-section in the sense of the present invention always refers to a section or a sectional representation at right angles to the longitudinal axis or axis of symmetry 9 of the respective container B1, B2 and/or the respective connecting arrangement 3A, 3B.

The second connecting arrangement 3B of the first embodiment preferably comprises a severing element 7 which is preferably configured to pierce, sever, cut or generally destroy the opening region 4A of the first connecting arrangement 3A. In particular, the severing element 7 comprises or is formed by a piercing device, a point, a blade, a wedge or generally a cutting and/or severing device.

The severing element 7 is preferably arranged and/or attached on the opening region 4B of the second connecting arrangement, particularly directly. The severing element 7 is preferably arranged on an outer side of the second connecting arrangement 3B or on a side or outer side remote from the interior of the container B2. The severing element 7 is preferably arranged so that by bringing the connecting arrangement 3B of the severing element 7 close to the opening region 4A of the first connecting arrangement the severing element 7 applies a force to the opening region 4A which leads to the destruction and opening of the opening region 4A, preferably without opening or destroying the opening region 4B of the second connecting arrangement 3B.

In particular, the severing element 7 is a device which concentrates a force acting on the opening region 4A or distributes a counter-force acting on the second connecting arrangement 3B or on the opening region 4A such that the opening region 3B of the second connecting arrangement 3B remains intact when the opening region 4A is opened by being destroyed by the severing element 7.

In a variant (not shown) the severing element 7 is arranged on an inner side of the connecting arrangement, within or inside the interior of the container B1 or (viewed from outside) arranged behind the opening region 3B of the second connecting arrangement 3B. Preferably, the opening region 4A, 4A' of the first connecting arrangement 3A is destroyed by the severing element 7 as the mouth-shaped portion 5A is pushed into the mouth-shaped portion 5B of the second connecting arrangement 3B. For this purpose, the severing element 7 is provided, particularly directly (on the inside or on the side remote from the first connecting arrangement 3A) behind the opening region 4B of the second connecting arrangement 3B.

Preferably, the severing element 7 is immovably arranged or fixed on the second connecting arrangement 3B, particularly (directly) on, in front of or behind the opening region 4A.

FIG. 2 shows the proposed connecting system 1 in a starting position in which the opening regions 4A, 4B or the containers B1, B2 are closed or sealed. In particular, they are (in each case) bottles or bottle-like containers B1, B2, the bottom opening regions 4A, 4B of which are closed in the starting position.

As shown by the arrow 8 indicating movement, the first connecting arrangement 3A and the second connecting arrangement 3B may be moved towards one another or pushed into one another. For this purpose, the connecting arrangements 3A, 3B are preferably moved axially towards one another with respect to a central axis or axis of symmetry 9. The central axis or axis of symmetry 9 is preferably a central axis or axis of symmetry 9 of the mouth-shaped portion or portions 5A, 5B and/or of the opening region or regions 4A, 4B and/or of the container or containers B1, B2.

The containers B1, B2, the connecting arrangements 3A, 3B, the opening regions 4A, 4B and/or the mouth-shaped portions 5A, 5B may thus be formed substantially symmetrically with respect to the central axis or axis of symmetry 9. An axially symmetrical and/or rotationally symmetrical construction of the mouth-shaped portions 5A, 5B is preferred, as this enables the connecting arrangements 3A, 3B to be used independently of their rotary position. However, other solutions are also theoretically possible, particularly ones in which the mouth-shaped portions 5A, 5B are rotationally asymmetrical or non-round and preferably a guide is provided which is configured to define a rotary position of the connecting arrangements 3A, 3B relative to the central axis or axis of symmetry 9. This will be discussed in more detail in connection with the second embodiment.

As can be seen in FIG. 3, as the connecting arrangements 3A, 3B come closer to one another the severing element 7 is applied to the opening region 4A, preferably with a point 7A and by further movement of the connecting arrangements 3A, 3B towards one another, pushed through the opening region 4A. In this way the opening region 4A is destroyed or the connecting arrangement 3A and/or the container B1 is opened.

Figure 16:
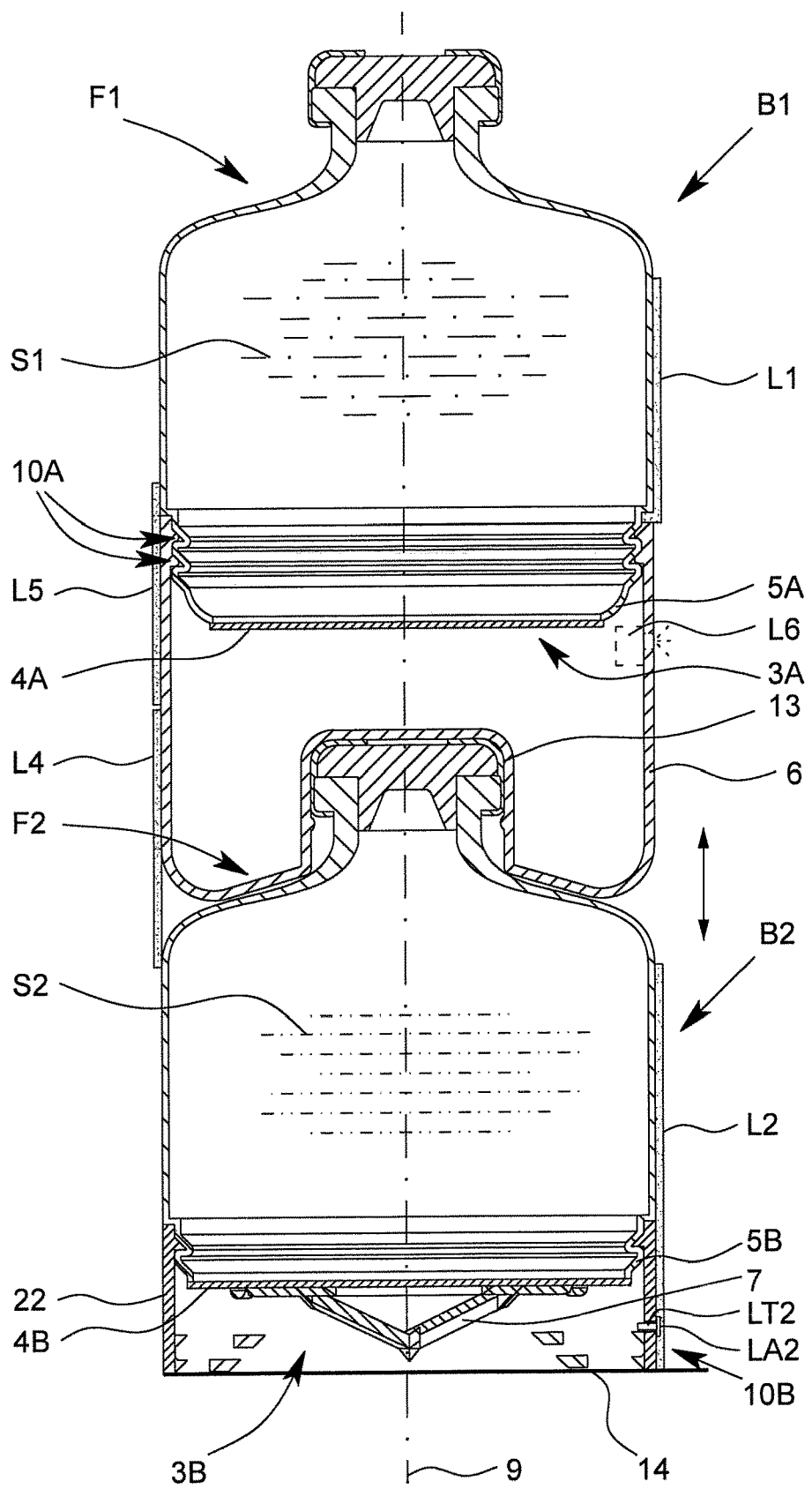
FIG. 16 shows a schematic longitudinal section through the proposed container system with the proposed connecting system according to the first embodiment in a transporting configuration.
Figure 17:
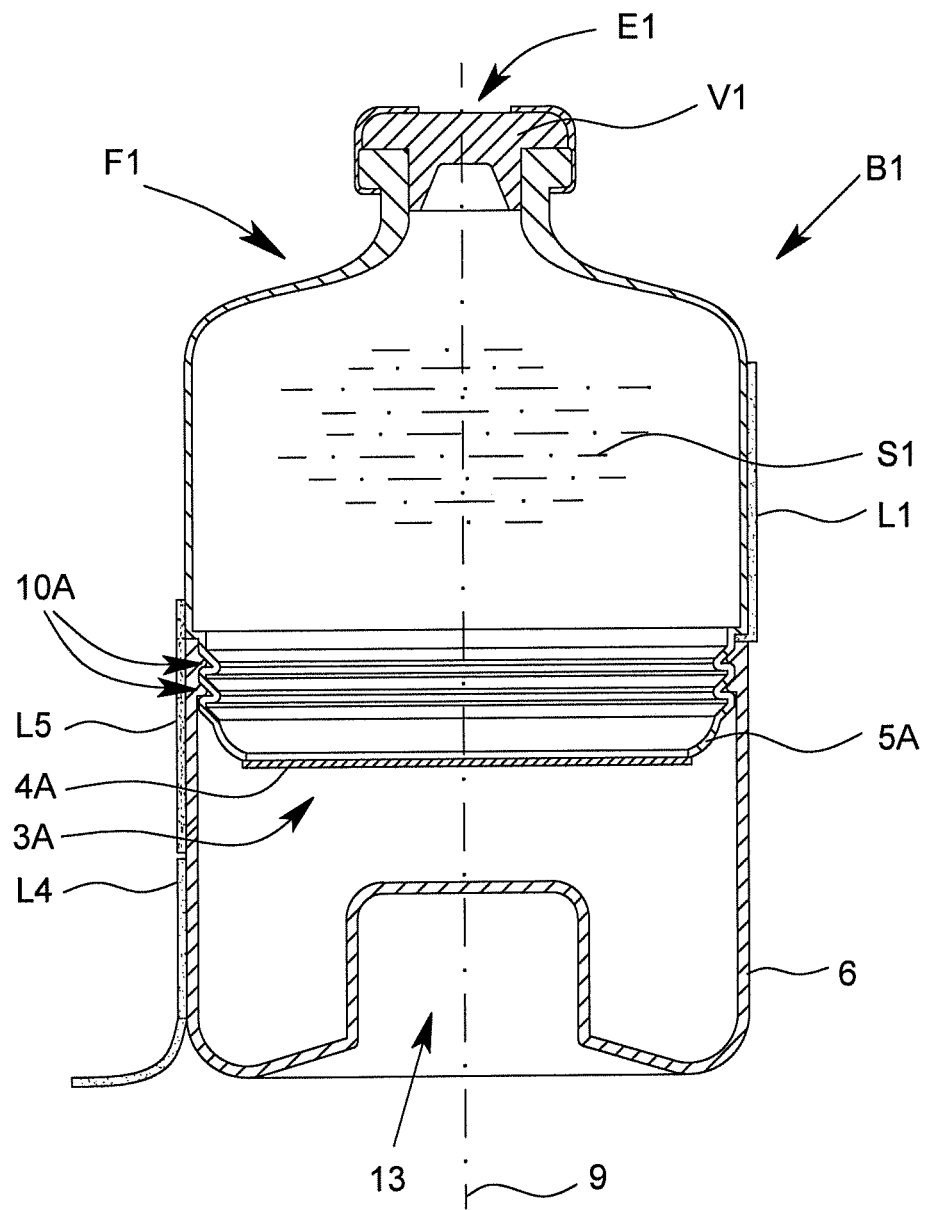
FIG. 17 shows a schematic longitudinal section through a first container with a first connecting arrangement covered in sterile or sterilizable manner.

The connecting arrangements 3A, 3A', 3B, 3B' are preferably designed to be separate and/or independent of one another in a starting position (cf. also FIGS. 16 and 17). This advantageously enables common and also separate use of cavities or containers B1, B2, B3 which are connected to or connectable with the connecting arrangements 3A, 3A', 3B, 3B'.

In the starting position, the connecting arrangements 3A, 3A', 3B, 3B' are preferably unconnected or fluidically separated from one another. As a result of the formation of the fluidic connection 2, the connecting arrangements 3A, 3A', 3B, 3B' move into a connecting position in which the fluidic connection 2 is made.

A fluidic connection 2 between the containers B1, B2, B3 is preferably produced at least when the volumes or substances S1, S2, S3 enclosed by the containers B1, B2, B3 are able to be moved between the containers B1, B2, B3, by gravity and/or mixed with one another.

The fluidic connection 2 is, in particular, a channel or a passage through which fluid substances S1, S2, S3, particularly liquids, can flow.

The connecting arrangements 3A, 3A', 3B, 3B' are preferably usable only once and/or are irreversibly openable; the fluidic connection 2 is preferably permanent and/or irreversible.

The connecting system 1 is preferably configured for the provision of a non-releasable or non-separable connection, particularly with the non-separable connection taking place even before at least one of the connecting arrangements 3A, 3A', 3B, 3B' has been opened. This prevents substances from escaping and advantageously prevents a partial mixing process from taking place.

The connecting arrangements 3A, 3A', 3B, 3B' preferably comprise securing devices 10A, 10B for producing the non-releasable connection, which produce a non-releasable connection between the connecting arrangements 3A, 3A', 3B, 3B' as a result of being fitted into one another and/or passed through one another by axial movement along their shared axis. In particular, the securing devices 10A, 10B comprise snap-fit hooks and/or are non-releasable or self-securing by means of snap-fit hooks or a snap-fit hook connection. In this way, it is possible to ensure that the connection cannot be undone manually and/or without damage or destruction.

The connecting arrangements 3A, 3A', 3B, 3B' can preferably be connected to one another non-releasably or inseparably by interlocking and/or frictional engagement, particularly by latching. In particular, different connecting positions, particularly latching positions, can be achieved by fitting one inside the other and/or inserting one inside the other by axial movement along the common axis.

In particular, one of the connecting arrangements 3A, 3A', 3B, 3B' comprises a latching means, particularly one or more latching lugs, arranged on portions located axially behind one another. Preferably, the latching means of one of the connecting arrangements are arranged such that one or more complementary latching means of the other connecting arrangement 3A, 3A', 3B, 3B', particularly one or more grooves or undercuts, latch into one another to form an engagement by being fitted into one another and/or inserted in one another with axial movement along the common axis. This enables the non-releasable or inseparable connection or the connecting position to be achieved.

The connecting arrangements 3A, 3A', 3B, 3B' are preferably configured so that when a first connecting position is reached the non-releasable or inseparable connection is made and/or none or only one of the first and second connecting arrangements 3A, 3A', 3B, 3B' is or has been opened. The fluidic connection 2 is thus preferably not yet or not entirely formed in the first latching position.

When another, second connecting position is reached which is preferably after the first connecting position in location and/or time, the continuous fluidic connection 2 and/or the opening of the two connecting arrangements 3A, 3A', 3B, 3B' is preferably produced.

By bringing the first connecting arrangement 3A, 3A' and the second connecting arrangement 3B, 3B' towards one another, preferably first of all only one of the first and second opening regions 4A, 4A', 4B, 4B' is broken, particularly pierced, and only as the connecting arrangements 3A, 3A', 3B, 3B' are brought closer together or subsequently rotated relative to one another or pushed into one another, is the continuous fluidic connection 2 produced by the breakage of the other one of the first and second opening regions 4A, 4A', 4B, 4B'.

Preferably, the connecting system 1 has a first connecting position in which the connecting arrangements 3A, 3B are connected to one another non-releasably, preferably by latching. For this purpose the connecting arrangements 3A, 3B may have securing devices 10A, 10B corresponding to another which produce a non-releasable connection between the connecting arrangements 3A, 3B as the connecting arrangements 3A, 3B are brought close together.

In the embodiment shown, the securing devices 10A, 10B are formed by corresponding or complementary undercuts, latching lugs or the like. In particular, individual latching lugs are formed on one of the connecting arrangements 3A, 3B, and in particular, annular beads and/or undercuts are formed on the other of the connecting arrangements 3A, 3B, which by co-operating provide a latching connection between the connecting arrangements 3A, 3B.

Particularly preferably, the securing devices 10A, 10B are configured for connecting the connecting arrangement 3A, 3B non-releasably with one another in a first connecting position but allowing further movement of the connecting arrangement 3A, 3B towards one another.

Moreover, the securing devices 10A, 10B are preferably configured so as to support a further, second connecting position in which the connecting arrangements 3A, 3B are brought more closely together or pushed further into one another than in the first connecting position. Particularly preferably, a plurality of latching positions are provided, in which, in a first latching position, the connecting arrangements 3A, 3B are already non-releasably connected to one another. The proposed connecting system 1 is shown in this first connecting position in FIG. 3.

In the first connecting position, one of the connecting arrangements 3A, 3B may already have been opened. Alternatively, or additionally, the first connecting position may also be characterized in that a non-releasable connection has indeed been made between the connecting arrangements 3A, 3B but none of the opening regions 4A, 4B has yet been opened or is being opened.

In the embodiment shown in FIG. 3, in the first connecting position, the first connecting arrangements 3A are connected to the second connecting arrangement 3B in non-releasable manner by latching and the first opening region 4A has already been opened or destroyed by the severing element 7.

FIG. 4 shows the proposed connecting system 1 in the second connection position, particularly a further latching position, in which the connecting arrangements 3A, 3B have been further brought together and/or pushed further inside one another, particularly at least substantially completely, compared with the first connecting position. In the second connecting position the first opening region 4A of the first connecting arrangement 3A has been opened by the second connecting arrangement 3B and furthermore the opening region 4B of the second connecting arrangement 3B has been opened by the first connecting arrangement 3A.

In order to open the second connecting arrangement 3B with or by means of the first connecting arrangement 3A, preferably the mouth-shaped portion 5A of the first connecting arrangement 3A is pushed through the opening region 4B of the second connecting arrangement 3B, thereby destroying said opening region 4B. This is preferably done as the connecting arrangements 3A, 3B are moved from the first connecting position into the second connecting position.

The securing devices 10A, 10B are preferably configured to prevent (axial) movement of the connecting arrangements 3A, 3B away from one another, both in the first connecting position and in the second connecting position. Thus it is envisaged, in particular, that the connecting arrangements 3A, 3B are movable further into the second connecting position from the first connecting position but not in an opposite direction. It is also preferable that the connecting arrangements 3A, 3B in the second connecting position (cf. FIG. 4) cannot be moved back into the first connecting position.

Preferably, the connecting arrangements 3A, 3B abut on one another, particularly sealingly, in the first connecting position. This prevents substances S1, S2 from escaping.

According to an aspect of the present invention which can also be implemented independently, during or as a result of the opening of the opening region 4B of the second connecting arrangement 3B by the mouth-shaped portion 5A of the first connecting arrangement 3A, a seal is formed relative to the environment. In particular, the opening region 4B of the second connecting arrangement 3B forms a sealing system with the mouth-shaped portion 5B of the second connecting arrangement 3B. Alternatively or additionally, the mouth-shaped portions 5A, 5B may have a sealing action by bearing against one another, while the opening region 4B acts sealingly or provides a seal, particularly at the edges and/or in the transitional area to the mouth-shaped portion 5B. However, there are also other possible solutions, for example using an additional or separate rubber seal, sealing lip or the like.

The connecting arrangements 3A, 3B or the connecting system 1 is or are preferably formed without threads. It has been found that systems known from the prior art which use threads to move a cutting tool in order to open containers are more prone to defects and require greater expense in order to create an opening or fluidic connection. Advantageously, the connecting arrangements 3A, 3B of the present connecting system can be connected to one another by a simple linear or axial movement and/or by moving directly towards one another (without the need for any additional rotation through several revolutions relative to one another). This has proved advantageous for rapid and comfortable production of the fluidic connection 2.

In this connection it is also advantageous that the proposed connecting system 1 comprises one or more connecting positions, particularly preferably in the form of latching positions. This has the particular advantage over interlocking threads that a non-releasable connection can be produced between the connecting arrangements 3A, 3B. On the other hand, with a threaded connection, dismantling and contamination are possible.

Theoretically, however, it is also possible to combine aspects of the present invention with connecting arrangements 3A, 3B which are connected or connectable by interlocking threads or in which the fluidic connection 2 can be produced by interlocking threads and a rotational movement relative to one another.

FIGS. 5 to 13 hereinafter illustrate a proposed connecting system 1 according to a second embodiment. Only the special features and differences from the embodiments described above will be discussed and therefore the foregoing remarks also apply in a supplementary manner to the second embodiment unless specifically stated to the contrary or obvious to the skilled man.

Figure 5:
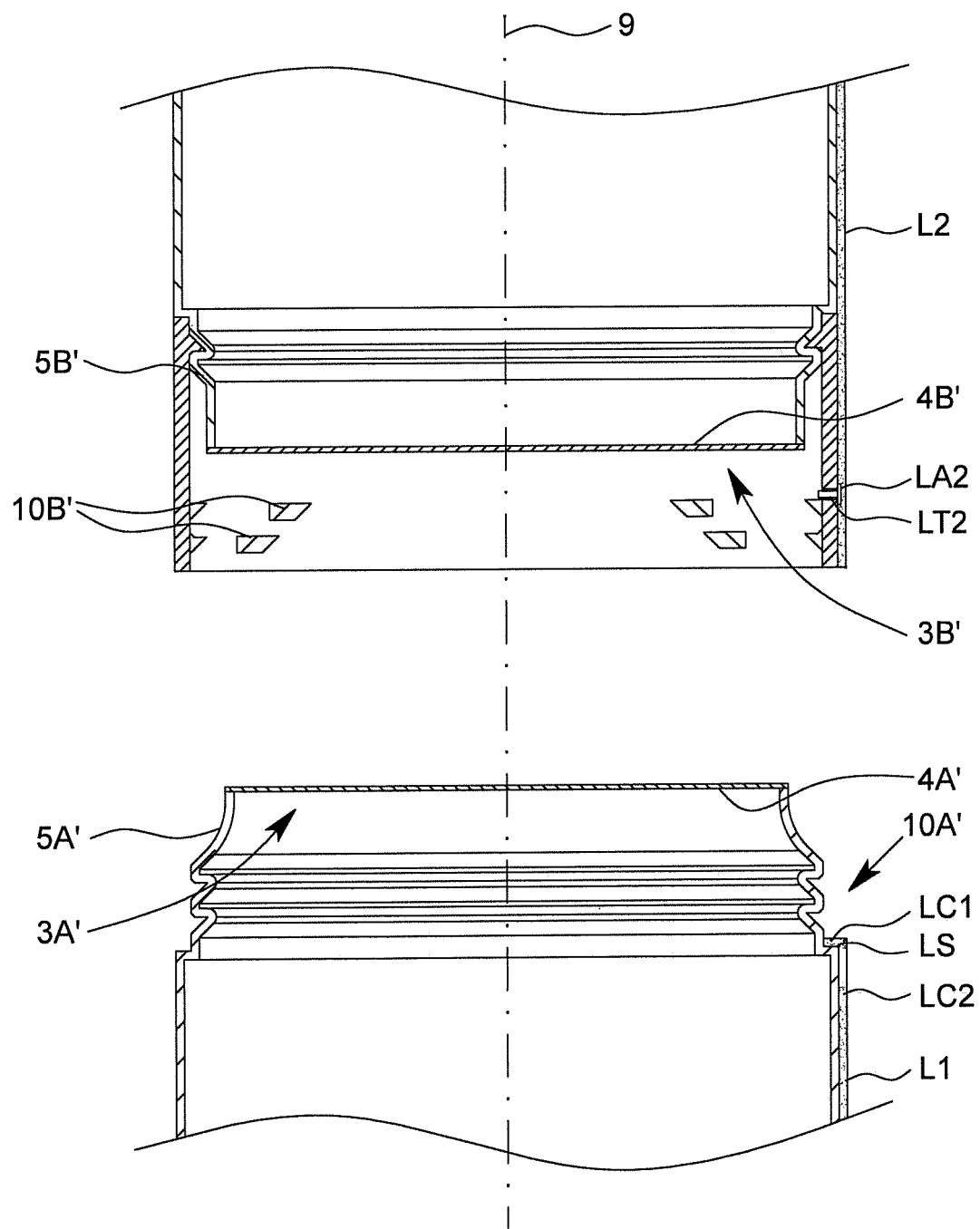
FIG. 5 shows a longitudinal section through a proposed connecting system in a second embodiment in a starting position.

FIG. 5 shows in a starting position a first connecting arrangement 3N and a second connecting arrangement 3B' according to the second embodiment. In the second embodiment, preferably none of the connecting arrangements 3A', 3B' has a severing element. In particular, the connecting system 1 according to the second embodiment is free from cutting tools, severing mechanisms and/or free from sharp edged projections or portions for opening.

In the second embodiment, mouth-shaped portions 5A' and 5B' of the connecting arrangement 3N, 3B' are preferably configured to be rotationally non-symmetrical or non-round, non-circular or oval with respect to the central axis or axis of symmetry 9. Preferably, the mouth-shaped portions 5A, 5B are configured to correspond to one another and/or to be similar in relation to a circumferential line, so that they can be arranged one inside the other and/or one can be pushed into one another. Moreover, for supplementary information, reference may be made to the explanations of the mouth-shaped portions 5A, 5B in the first embodiment.

Figure 6:
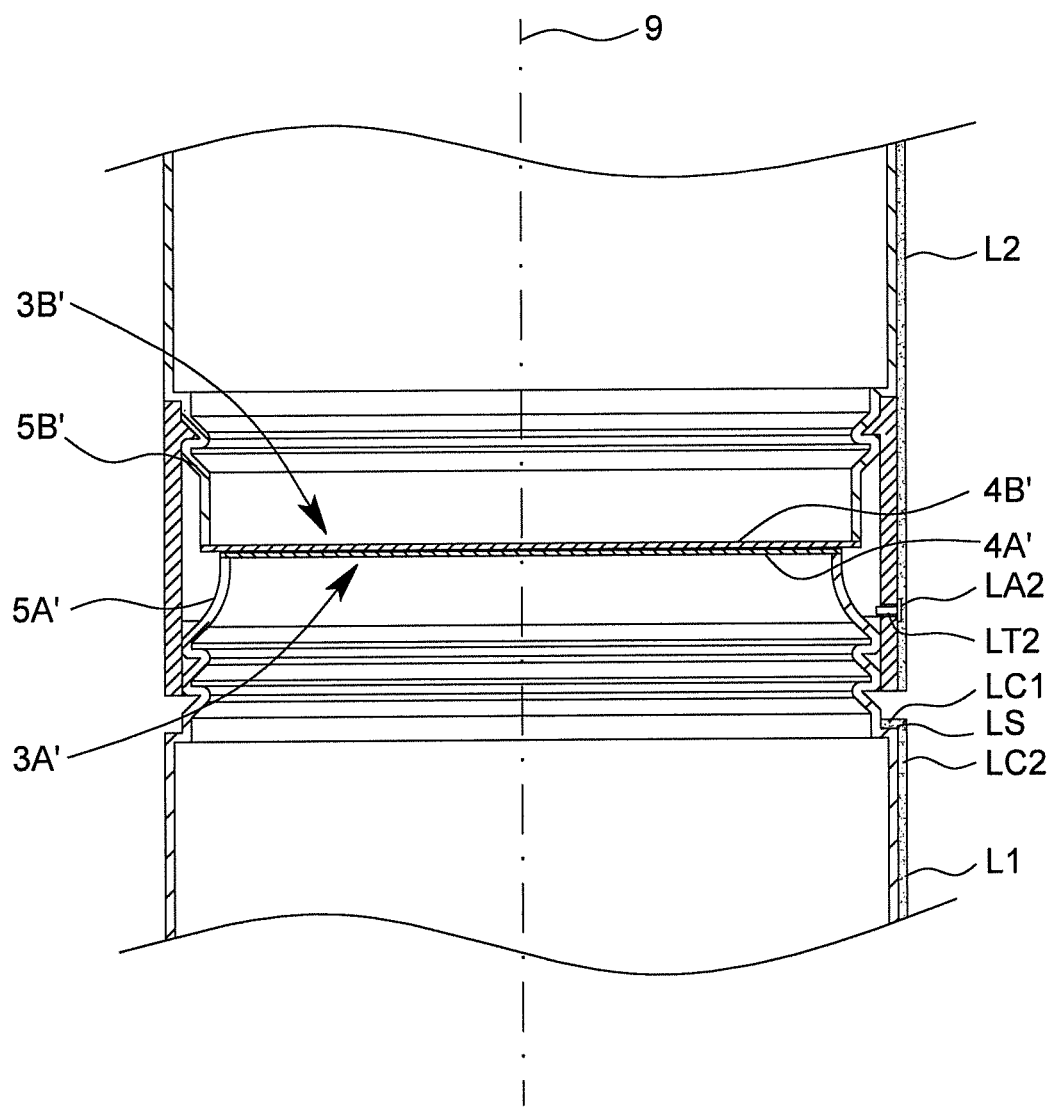
FIG. 6 shows a longitudinal section through the proposed connecting system in the second embodiment in a first connecting position.

FIG. 6 shows the connecting arrangements 3A', 3B' in the first connecting position in which they are connected to one another, preferably non-releasably. For this, the securing devices 10A, 10B may be used as explained hereinbefore.

The connecting mean 3A', 3b' preferably comprise opening regions 4A', 4B' which correspond to or resemble the opening region in 4A, 4B of the first embodiment. In the first connecting position according to FIG. 6, the opening regions 4A', 4B' abut on one another or are directly adjacent to one another. Alternatively, in the first connecting position, the opening region 4B' of the second connecting arrangement 3B' may, however, also already have been opened, as explained hereinafter in connection with FIG. 7.

Figure 7:
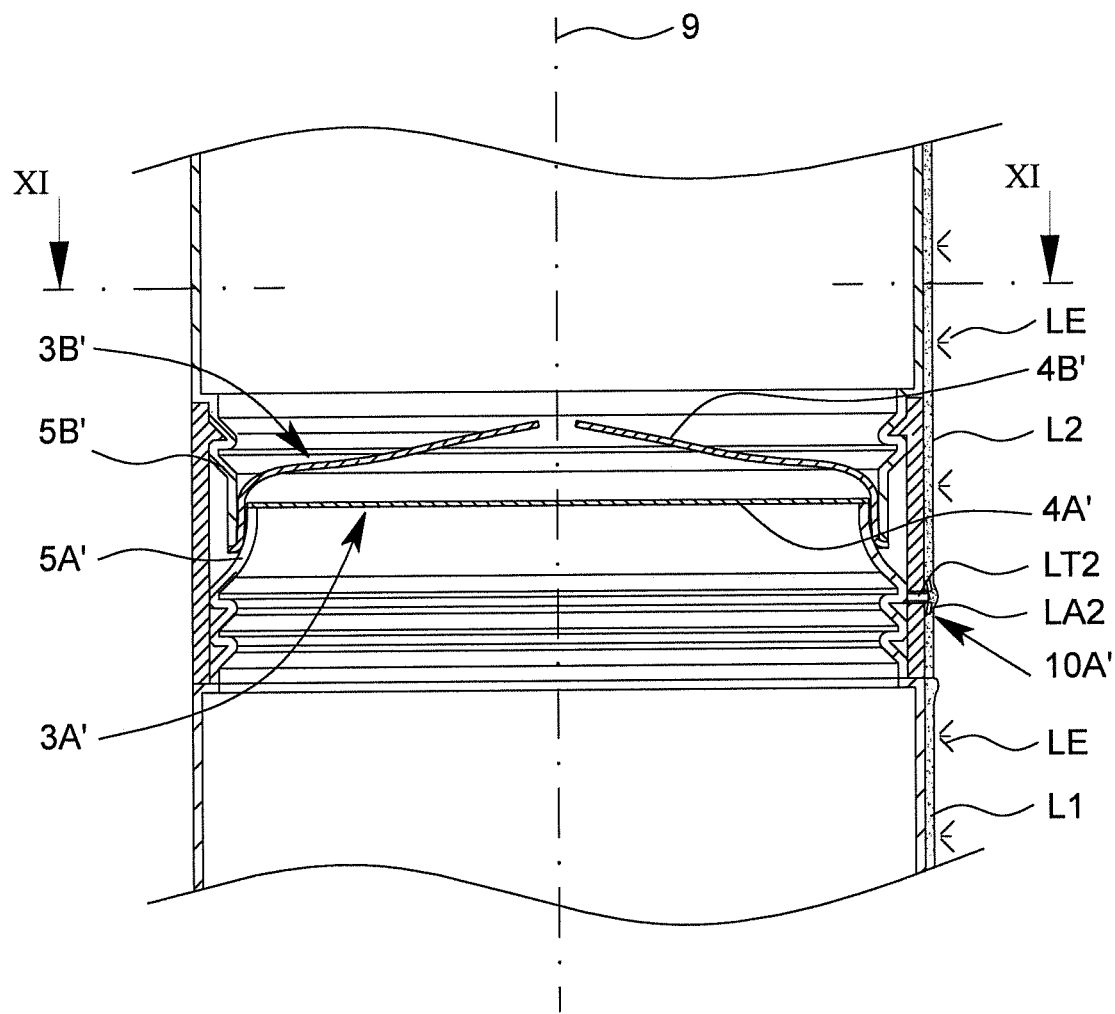
FIG. 7 shows a longitudinal section through the proposed connecting system in the second embodiment in a second connecting position with the connecting arrangements oriented with one another.

For opening or penetrating the second opening region 4B', the mouth-shaped portion 5A' of the first connecting arrangement 3N is pressed through the opening region 4B' of the second connecting arrangement 3B' as already explained in connection with the opening of the opening region 4B of the first embodiment. Preferably, the opening region 4B', particularly a sealing film or a film-like portion of the second connecting arrangement 3B' is destroyed or opened, particularly by pushing part of the first connecting arrangement 3A' through the opening region 4B' so that the opening region 4B' is opened or the film or the film-shaped portion which forms the opening region 4B' is pierced or destroyed. The result is shown in FIG. 7, in which, as a result of reaching the second connecting position, the second connecting arrangement 3B has been opened in the manner described.

By contrast with the first embodiment, the method for providing the fluidic connection 2 in the second embodiment begins with the step of opening the second connecting arrangement 3B' by means of the mouth-shaped portion 5A' or destroying the opening region 4B' of the second connecting arrangement 3B' using the mouth-shaped portion 5A'.

It is also envisaged in the second embodiment that the connecting arrangements 3A', 3B' are rotatable relative to one another or about the (common) central axis or axis of symmetry 9 in their connected state, particularly in the second connecting position. As a result, preferably the other of the connecting arrangements 3N, 3b', i.e., the first connecting arrangement 3A', in particular, is opened, as explained in detail hereinafter with reference to FIGS. 8 to 13.

In one aspect it is preferable that the first opening region 4A, 4A', 4B, 4B' of the first connecting arrangement 4A, 4A' can be opened by deformation by means of the second connecting arrangement 4B, 4B'. The opening regions 4A, 4A', 4B, 4B' can also be mutually opened by mutual deformation. Opening by deformation preferably does not require any shearing edges or severing elements, which is advantageous in terms of a simple manufacturing process with reduced use of materials.

The second connecting arrangement 3B, 3B' is preferably configured to open the first connecting arrangement 3A, 3A', while the second connecting arrangement 3B, 3B' is preferably configured to open the opening region 4A, 4A', 4B, 4B' of the first connecting arrangement 4A, 4A' by deformation of the first connecting arrangement 3A, 3A'.

Particularly preferably, in this aspect, the deformation is initiated by rotating the connecting arrangements 3A, 3A' relative to one another, particularly about the common axis 9, and/or opening the opening regions 4A, 4A' 4B, 4B' of the first connecting arrangement 3A, 3A'.

The connecting arrangements 3A, 3N, 3B, 3B' preferably have non-round, particularly oval or at least substantially elliptical portions corresponding to one another which can be inserted in one another and/or cause deformation and/or opening when rotated relative to one another.

The deformation preferably brings about a tensioning of the opening region 4A, 4A', at least substantially radially or transversely with respect to a central axis or axis of symmetry 9 or along the opening region of the opening region 4A, 4A', as a result of which the opening region 4A, 4A' is torn, broken or detached and/or the opening region 4A, 4A' is opened.

At the same time, the second connecting arrangement 3B, 3B' may have an, in particular film-like, brittle and/or unstable opening region 4B, 4B', preferably with the first connecting arrangement 3A, 3A' being configured for opening the second connecting arrangement 3B, 3B'. In particular, the first connecting arrangement 3A, 3A' is configured to open the second connecting arrangement 3B, 3B' by breaking through the opening region 4B, 4B' of the second connecting arrangement 3B, 3B'.

The first connecting arrangement 3A, 3A' preferably comprises a mouth-shaped portion 5A, 5A' which adjoins the opening region 4A, 4A' or surrounds the opening region 4A, 4A', the mouth-shaped portion 5A, 5A' being deformable so that the opening region 4A, 4B can be opened by the deformation.

The mouth-shaped portion 5A, 5A' is preferably in the form of a web, a neck, a wall, a thin wall, or it is elastic and/or flexible, and/or the mouth-shaped portion 5A, 5A' is more elastic, more flexible and/or more stable than the opening region 4A, 4A', which is preferably opened on deformation of the mouth-shaped portion 5A, 5A' the opening region 4A, 4A', particularly by tearing, breaking or detaching.

The second connecting arrangement 3B, 3B' is preferably configured for deforming the mouth-shaped portion of the first connecting arrangement 3A, 3A', so that the deformation causes the opening region 4A, 4A' of the first connecting arrangement 3A, 3A' to open.

The mouth-shaped portion 5A, 5A', 5B, 5B' is preferably non-round, particularly oval, at least essentially elliptically and/or polygonal in cross section, while the second connecting arrangement 3B, 3B' has a corresponding cross section, so that rotating the connecting arrangements 3A, 3A', 3B, 3B' relative to one another causes deformation and/or opening of the first connecting arrangement 3A, 3A' in their opening region 4A, 4A'.

Both connecting arrangements 3A, 3A' 3B, 3B' preferably have mouth-shaped portions 5A, 5A', 5B, 5B' which can be arranged in oriented manner inside one another or can be pushed into one another, while rotation of the connecting arrangements 3A, 3A', 3B, 3B' or of the mouth-shaped portions 5A, 5A', 5B, 5B' relative to one another brings about deformation of the first and, preferably, the second mouth-shaped portion 5A, 5A', 5B, 5B'.

The connecting arrangements 3A, 3A', 3B, 3B' can be connected to one another by a bayonet-type connection or they may comprise connectors or guides 18A, 18B, which are configured to form a bayonet-type connection. For this purpose, the mouth-shaped portions 5A, 5N, 5B, 5B' may initially be pushed or capable of being pushed (only) in the axial direction into one another and only afterwards may they be rotated or rotatable relative to one another, while preferably the fluidic connection 2 is not formed until they are rotated relative to one another. The guides 18A, 18B may thus be designed for a bayonet-type connection. For this purpose, a (purely) axially extending guide may be adjacent to a (purely) radial guide.

Preferably, by rotating the connecting arrangements 3A', 3B' relative to one another while the mouth-shaped portion 5A' of the first connecting arrangement 3A' is arranged in the mouth-shaped portion 5B' of the second connecting arrangement 3B', the opening region 4A' of the first connecting arrangement 3N is mechanically stressed, particularly tensioned by the deformation of the mouth-shaped portion 5A' of the first connecting arrangement 3A' to such an extent that it tears.

Figure 9:
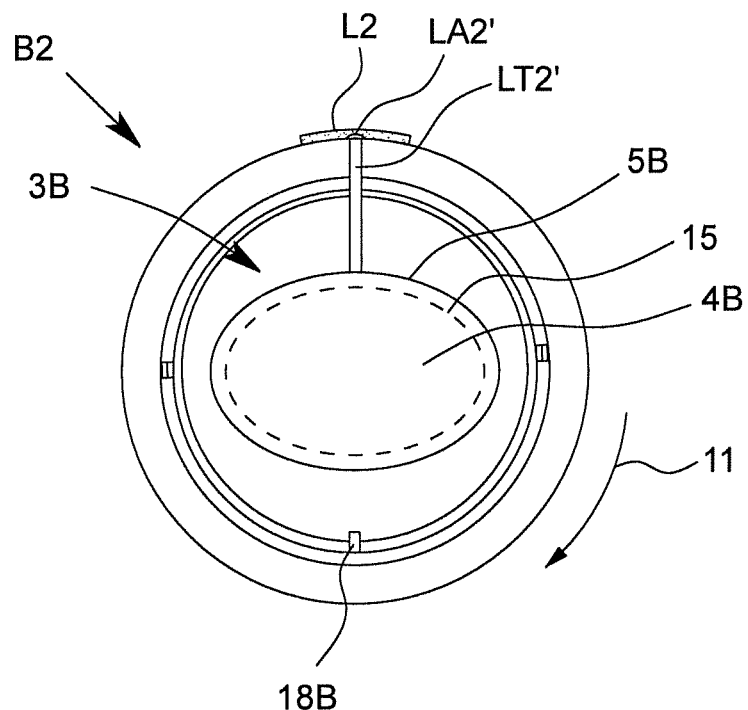
FIG. 9 shows a schematic plan view of a first container with a first connecting arrangement for the proposed connecting system of the second embodiment.
Figure 10:
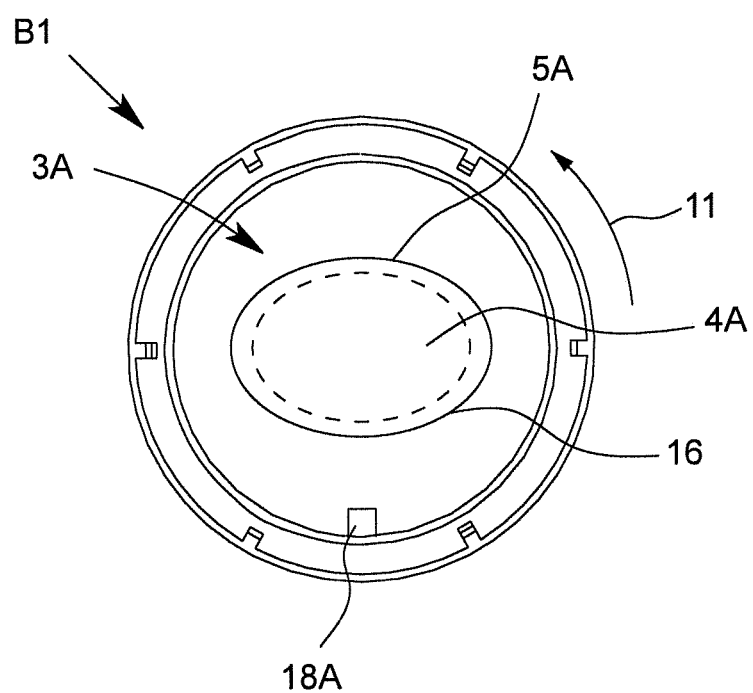
FIG. 10 shows a schematic plan view of a second container with a second connecting arrangement for the proposed connecting system of the second embodiment.

To improve the understanding of the opening mechanism for opening the first opening region 4A' of the first connecting arrangement 3N from the second embodiment, FIGS. 9 and 10 each show a plan view of a connecting arrangement 3A' 3B'. The second connecting arrangement 3B' shown in FIG. 9 preferably has a mouth-shaped portion 5B' which resembles the mouth-shaped portion 5A' of the first connecting arrangement 3A' shown in FIG. 10 in shape and/or outline, but is larger in its dimensions, diameters, longitudinal extent and/or transverse extent (at right angles to the central axis or axis of symmetry 9).

In particular, the second connecting arrangement 3B' comprises an inner circumferential edge 15—indicated by dashed lines in the plan view in FIG. 9—which resembles an outer circumferential edge 16 of the mouth-shaped portion 5A', corresponds thereto and/or is configured so that the outer circumferential edge 16 can be accommodated by the inner circumferential edge 15. Preferably, a maximum diameter of the inner circumferential edge 15 is greater than a maximum diameter of the outer circumferential edge 16 and/or a minimum diameter of the inner circumferential edge 15 is greater than a minimum diameter of the outer circumferential edge 16, preferably by more than 2% or 3% and/or less than 40%, preferably less than 30%, more particularly less than 20%, 15% or 10%. This enables the mouth-shaped portions 5A', 5B' to be simply pushed one inside the other while at the same time reliably opening the opening region 4A' of the first connecting arrangement 3A'.

The mouth-shaped portions 5A', 5B' can preferably be arranged inside one another or pushed into one another with play. As a result of the arrangement of the mouth-shaped portions 5A', 5B' a gap 17 or a spacing is formed (at least partially) between the inner circumferential edge 15 and the outer circumferential edge 16.

In the embodiment shown, which relates to a particularly preferred variant, the mouth-shaped portions 5N, 5B' are each oval in cross section, particularly at least substantially elliptical. Theoretically, however, other shapes are possible, for example at least substantially square or other polygonal shapes. In theory it is preferable that the extent of the cross section in the main axial direction or the maximum extent in the secondary axial direction (centrally and transversally or perpendicularly to the main axial direction) exceeds or the minimum extent of the cross section by a factor of more than 1.2, preferably 1.3, particularly 1.5, and/or at least or at least substantially by a factor root of 2. This allows sufficiently strong deformation during rotation of the connecting arrangements relative to one another so that the opening of the opening region 4A' of the first connecting arrangement 3N can take place reliably.

Figure 11:
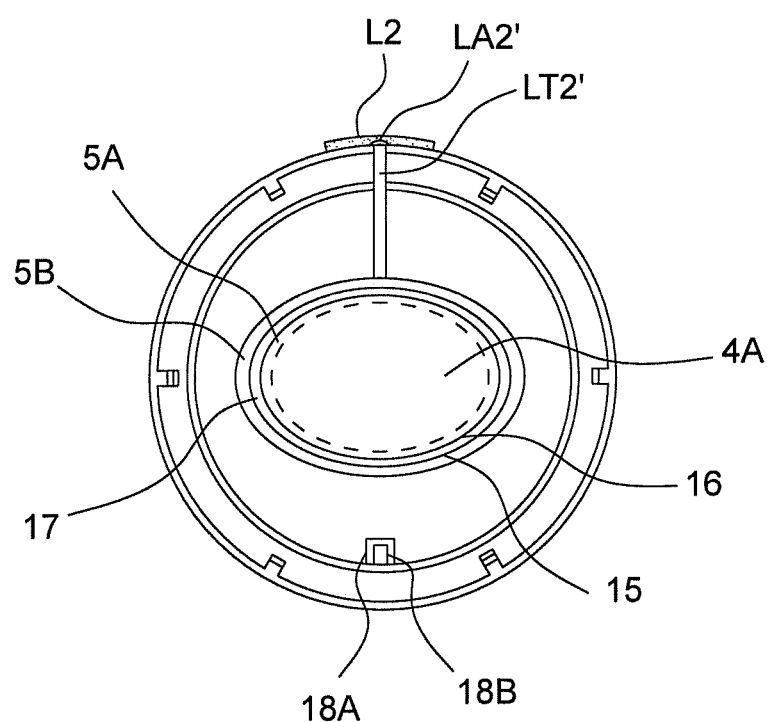
FIG. 11 shows a schematic cross-section through the proposed connecting system in the second embodiment along the section line XI-XI in FIG. 7.
Figure 12:
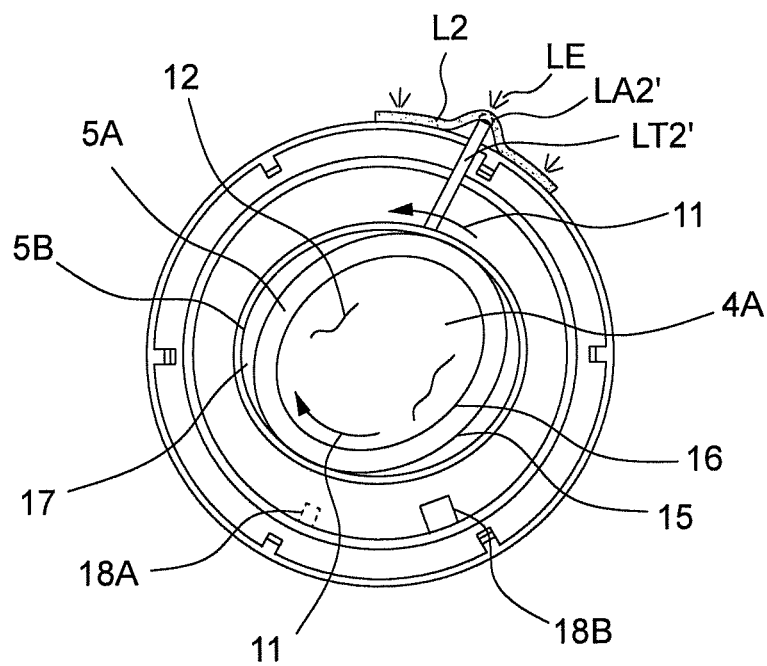
FIG. 12 shows a schematic cross-section through the proposed connecting system in the second embodiment after partial rotation of the connecting arrangements relative to one another.
Figure 13:
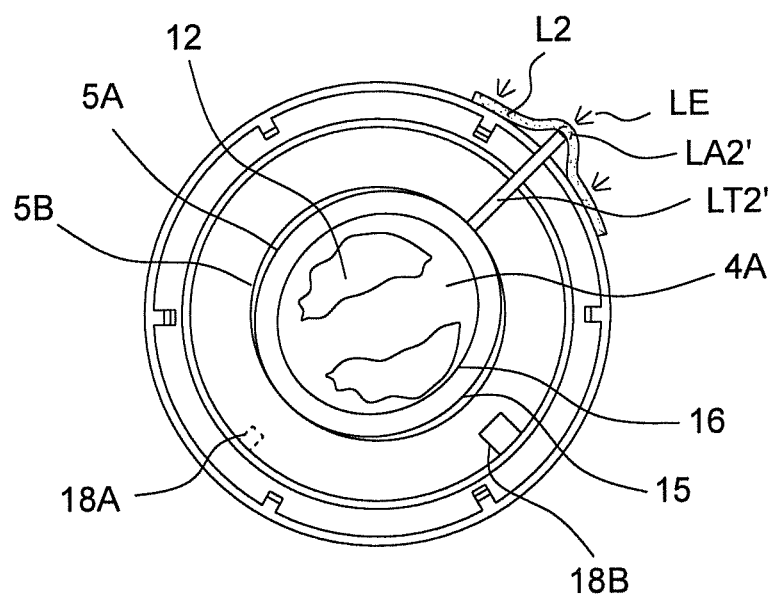
FIG. 13 shows a schematic cross-section through the proposed connecting system in the second embodiment along the section line XIII-XIII in FIG. 8.

In FIGS. 11 to 13, the connecting arrangements 3A', 3B' are shown in different rotational positions relative to one another, preferably in the second connecting position.

Preferably, the connecting arrangements 3A', 3B' can be turned or rotated through more than 45° and/or less than 200°, particularly less than 135° and/or at least substantially through 90°, in their (non-releasably) connected state or with the mouth-shaped portions 5A', 5B' inserted in one another, about the (common) central axis or axis of symmetry 9. This ensures deformation of one or both mouth-shaped portions 5A', 5B' and/or opening of an opening region 4A', 4B', particularly of the opening region 4A' of the first connecting arrangement 3A'.

Figure 8:
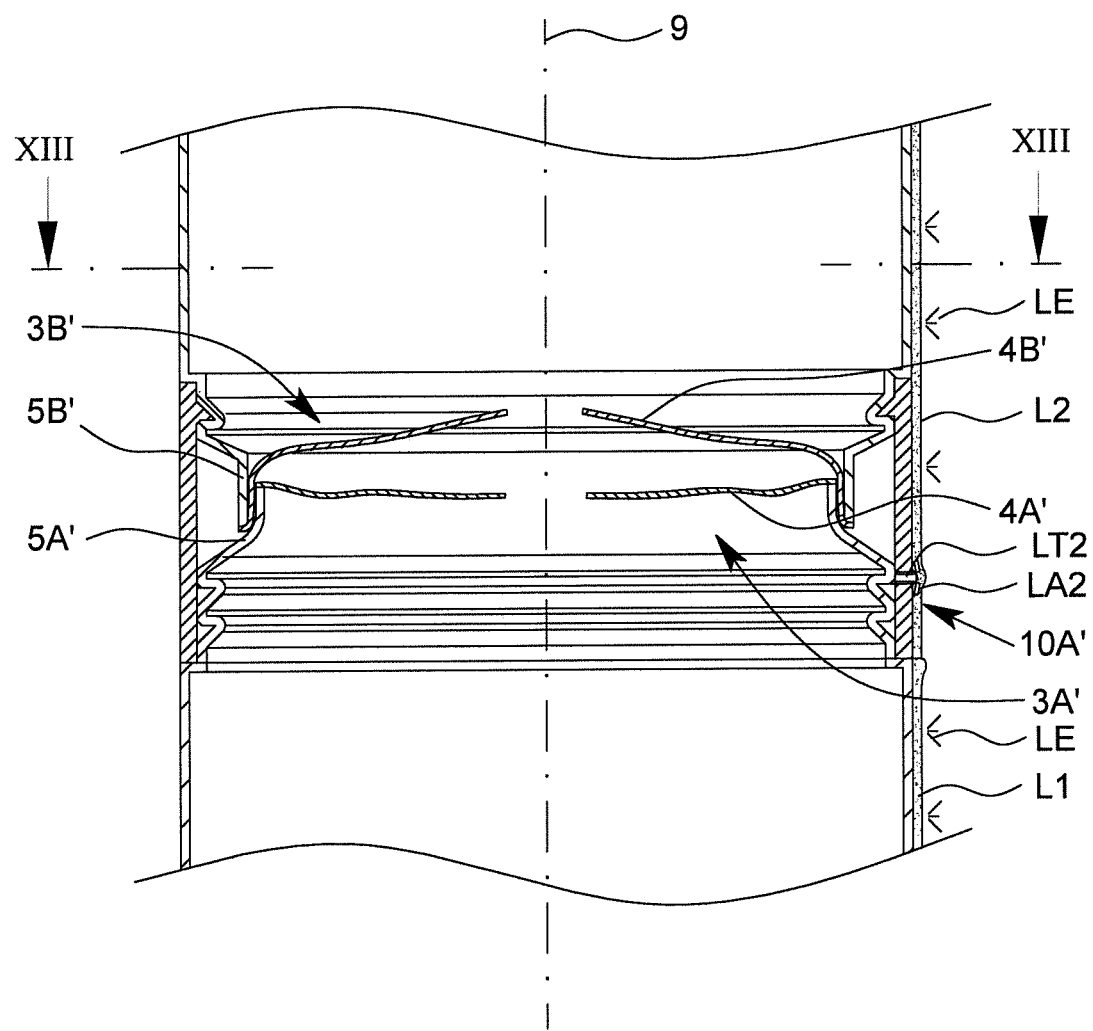
FIG. 8 shows a longitudinal section through the proposed connecting system in the second embodiment in the second connecting position with the connecting arrangements rotated relative to one another about a common axis.

In the embodiment shown in FIG. 8 the mouth-shaped portions 5A', 5B' are similar, particularly with reference to a circumferential line radially of the central axis or axis of symmetry 9, particularly so that after the first mouth-shaped portion 5A' has been inserted or pushed into the second mouth-shaped portion 5B' they rest loosely or with play on one another or at least partially abut directly on one another particularly at least at two points which are opposite one another in respect of the central axis or axis of symmetry 9 and/or at least 20%, preferably at least 50% of the respective circumferential line.

Because of the rotationally asymmetrical or non-round form of the mouth-shaped portions 5A, 5B, the rotation indicated by the rotation arrows 11 results in force which has a deforming effect on the first connecting arrangement 3A', particularly the mouth-shaped portion 5A' thereof. In the embodiment shown, the mouth-shaped portions 5A', 5B' are oval in cross section. This has proved particularly advantageous as it ensures that during rotation the mouth-shaped portions 5A', 5B' slide past one another without snagging and ensures at least substantially continuous deformation of the mouth-shaped portion 5B' of the second connecting arrangement 3B' during the rotation of the connecting arrangements 3A', 3B' relative to one another. However, other rotationally asymmetrical or non-round cross sections are also possible, such as rectangles, polygons, triangles or the like.

FIG. 12 shows, in a schematic section through the connecting system 1, particularly in the second connecting position, the mouth-shaped portions 5A', 5B' in a position rotated through about 45° to one another. The respective mouth-shaped portions 5A', 5B' generate forces on one another so as to produce deformation of the mouth-shaped portion 5B' of the second connecting arrangement 3B' and, preferably at the same time, a, particularly corresponding, deformation of the mouth-shaped portion 5A' of the first connecting arrangement 3A'. As indicated by the broken lines 12, the deformation of the mouth-shaped portion 5B' leads to tensile and/or pressure stresses on the opening region 4B' and, preferably, as a result, leads to fracture or opening.

FIG. 13 shows a schematic section through the connecting system 1 as proposed, in which the first connecting arrangement 3A' has been rotated through at least substantially 90° relative to the second connecting arrangement 3B'. Compared with the rotation through about 45° as shown in FIG. 12, the increasing rotation of the connecting arrangements 3A', 3B' relative to one another increases the tension or pressure and/or tensile stress on the opening region 4B' such that the opening region 4B' tears, breaks, becomes detached (at the edges) or opens in some other way.

The connecting system 1 according to the second embodiment preferably comprises a guide 18A, 18B (cf. FIGS. 9 and 10) for connecting the connecting arrangements 3A', 3B' in a rotationally oriented position or for determining a rotational position during the connection thereof. In particular, a sliding guide or the like is provided by means of which the connecting arrangements 4A', 4B' or the mouth-shaped portions 5A', 5B' can only be fitted, placed or pushed into one another in certain rotational positions (with respect to the central axis or axis of symmetry 9), preferably such that the mouth-shaped portions 5A', 5B' are similarly oriented.

The mouth-shaped portion 5A', 5B' are similarly oriented particularly when main axes, longitudinal axes, transverse axes, ends, corners and/or the like coincide with one another at least substantially, particularly such that the first mouth portion 5A' can be pushed into the second mouth portion 5B' at least substantially without any deformation of the mouth portions 5N, 5B'.

The guide 18A, 18B is preferably configured such that in the (second) connecting position or after the attachment of the connecting arrangements 3A', 3B' or after the mouth-shaped portions 5A', 5B' have been inserted or pushed into one another, it is possible to rotate these relative to one another, particularly about the central axis or axis of symmetry 9. In particular, the guide 18A, 18B comprises a slide or a portion which extends axially or parallel to the central axis or axis of symmetry 9 and, thereafter, has a radially extending portion, resulting in the rotational movement described above. However, other solutions are also possible.

The aspects of the first and second embodiment can also be combined with one another. Thus, it is additionally possible for the second connecting arrangement 3B, 3B' to comprise a severing element 7 which at least partially opens the opening region 4A, 4A' of the first connecting arrangement 3A, 3A' when the connecting arrangements 3A, 3A', 3B, 3B' are placed inside one another. The mouth-shaped portion 5A, 5A' can then be used to open, particularly to pierce, the opening region 4B' of the second connecting arrangement 3A, 3B'. Rotation of the connecting arrangements 3A, 3A', 3B, 3B' relative to one another about the central axis or axis of symmetry 9 then leads to deformation of one or both mouth-shaped portions 5A, 5A', 5B, 5B'. This leads to tensioning of the opening region or regions 4A, 4A', 4B, 4B'. In this way, further breaking and/or tearing of the opening region or regions 4A, 4A', 4B, 4B' can advantageously be achieved, as a result of which the fluidic connection 2 can be improved or the hydraulic cross section of the fluidic connection 2 can be enlarged.

The connecting arrangements 4A, 4A', 4B, 4B' are preferably configured for mutual opening and/or to complement and/or correspond to one another, so that the continuous fluidic connection 2 can be produced.

The connecting arrangements 3A, 3A', 3B, 3B' are preferably configured in order to produce a hydraulic cross section of more than 0.5 cm$^2$, preferably more than 1 cm$^2$ when producing the fluidic connection 2. This permits rapid and total mixing.

The connecting arrangements 3A, 3A', 3B, 3B' are preferably adapted to be axially inserted in one another, fitted into one another and/or formed without threads. This allows rapid and simple production of the fluidic connection 2.

By the production of the fluidic connection 2, the fluidic connection 2 preferably forms a passage between the containers B1, B2, B3 which is sealed off from the environment. This prevents the ingress of foreign substances or germs.

The second connecting arrangement 3B, 3B' is preferably configured to open the first connecting arrangement 3A, 3A' by breaking through the first opening region 4A, 4A' and/or the first connecting arrangement 3A, 3A' is configured to open the second connecting arrangement 3B, 3B' by breaking through the second opening region 4B, 4B'. By mutual destruction of the opening regions 4A, 4A', 4B, 4B' it is advantageously possible to produce an irreversible fluidic connection 2 of large enough diameter to allow rapid mixing.

The connecting system 1 is preferably self-sealing, as a result of the production of the fluidic connection 2, in particular with at least one of the opening regions 4A, 4A', 4B, 4B' having a sealing action as a result of or after the production of the fluidic connection 2, so that the continuous fluidic connection 2 forms a passage sealed off from the environment. Preferably, the production of the fluidic connection 2 forms a fluidic passage which is sealed off from the environment, particularly in fluid-tight, germproof and/or gas-tight manner.

For this purpose one of the opening regions 4A, 4N, 4B, 4B' or a device forming the respective opening region, after being perforated or otherwise destroyed as a sealing element, particularly a sealing lip, may extend between the connecting arrangements 3A, 3A', 3B, 3B' and in this way seal the connecting arrangements 3A, 3A', 3B, 3B' with one another or relative to one another.

The connecting system 1 is preferably self-sealing in sterile or sterilizable manner as a result of the production of the fluidic connection 2. In particular, the production of the fluidic connection 2 produces a seal which prevents the ingress of germs.

Preferably, in order to seal the connecting arrangements 3A, 3A', 3B, 3B' relative to one another, a seal, particularly a sealing ring or sealing lip, is provided.

Particularly preferably, in order to seal the fluidic connection 2, preferably from the environment, or to seal off the fluidic passage, at least one opening region 4A, 4A', 4B, 4B', preferably the second opening region 4B, 4B', acts as a seal, as a result of or after the formation of the fluidic connection 2.

In particular, it is envisaged that the at least one opening region 4A, 4A', 4B, 4B', preferably the second opening region 4B, 4B', has a sealing effect or acts as a seal at least at the edges or forms the sealing ring or the sealing lip when the fluidic connection 2 has been made. Alternatively, or additionally, it may be envisaged that the at least one opening region 4A, 4A', 4B, 4B', preferably the second opening region 4B, 4B', sealingly abuts on a connecting arrangement 3A, 3A', 3B, 3B', preferably the first or a corresponding connecting arrangement, particularly the mouth-shaped portion 5A, 5A', 5B, 5B' thereof, when it has been pierced with the mouth-shaped portion 5A, 5A', 5B, 5B' in order to produce the fluidic connection 2.

At least one opening region 4A, 4A', 4B, 4B', preferably the at least one opening region 4A, 4A', 4B, 4B', is preferably constructed to inhibit cracking around the edges and/or to form a seal and/or it has a material construction or layered structure in the edge region, which differs by comparison with a central portion, so that the edge region is more stable and/or acts as a seal after the edge region has been opened.

The containers B1, B2, B3 of the proposed container system B in the initial state have preferably been produced separately from one another and can be used separately and/or fluidically separated from one another. The connecting arrangements 3A, 3A', 3B, 3B' are preferably each fluidic ally sealed independently of one another in the initial state. After the fluidic connection 2 has been formed between the containers B1, B2, B3, these containers are preferably inseparably or non-releasably connected.

Figure 14:
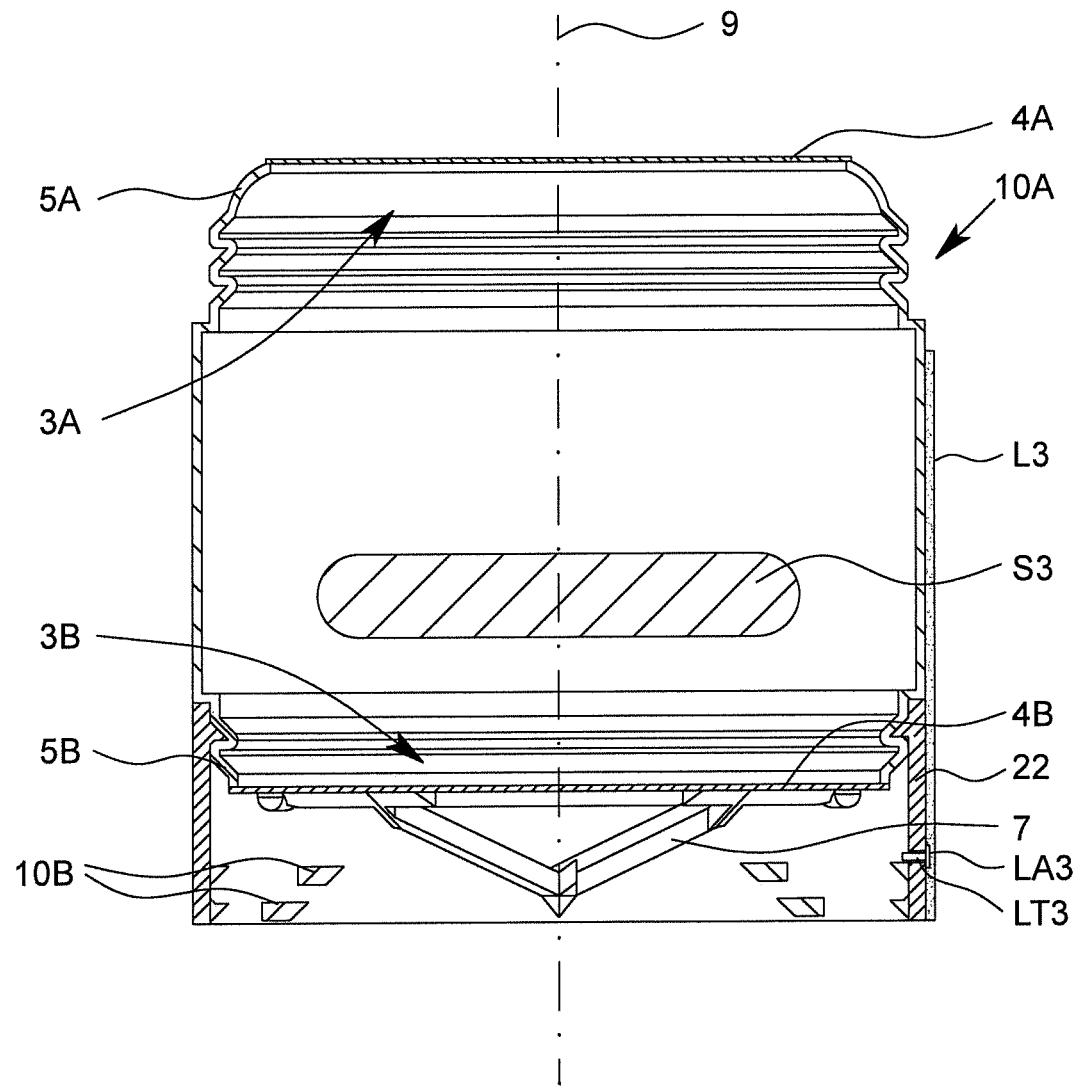
FIG. 14 shows a schematic longitudinal section through a container with connecting arrangements according to the first embodiment on opposite sides.

FIG. 14 shows another container B3, which may also be or form part of the container system B. The container system B preferably comprises the container B3. This has two different, corresponding and/or complementary connecting arrangements 4A, 4A', 4B, 4B'. As a result, this container B3 may serve as an adaptor between two other containers B1, B2 and/or may be connected to different containers B1, B2 and/or may allow more than two substances S1, S2, S3 to be mixed.

The container B3 comprises both the first connecting arrangement 3A and the second connecting arrangement 3B on different, preferably opposite, sides. The container B3 thus preferably comprises the first connecting arrangement 3A, 3A', on a first side, and the second of the connecting arrangements 3B, 3B' on a second side remote from the first side. This container is preferably free from removal openings E1, E2.

Moreover, the further container B3 is configured to produce a fluidic connection 2 on both sides by means of the proposed connecting system 1. The further container B3 may comprise or encompass an additional, further substance S3 different from the previous substances S1, S2, particularly a dry or freeze-dried substance (lyophilisate).

A plurality of containers B3 may be joined to one another and/to the first and/or second container B1, B2. In this way, more than three substances S1, S2, S3 may be mixed and/or a combination of more than 3 containers B1, B2, B3 may be formed and/or more than three containers B1, B2, B3 may be fluidically connected to one another.

As already explained in conjunction with FIG. 1, the proposed connecting system 1 is preferably used for fluidically connecting bottles or bottle-like containers B1, B2, particularly for the pharmaceutical sector. It is particularly preferable that the opening regions 4A, 4B, 4A' 4B' should be adapted to be covered in sterile manner for transportation.

Figure 15:
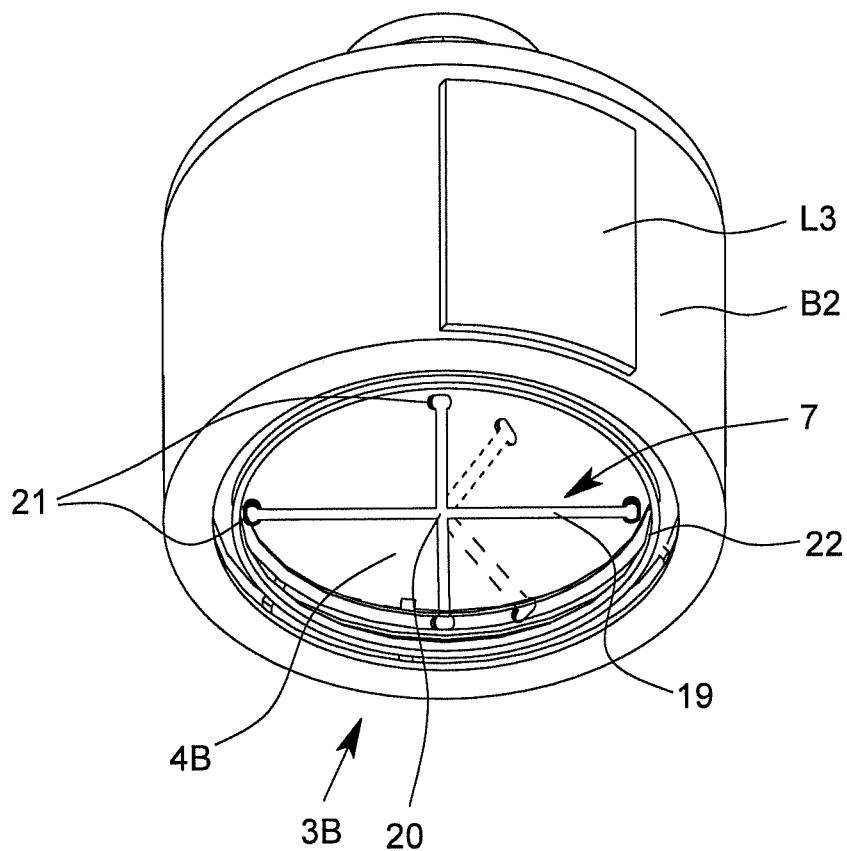
FIG. 15 shows a perspective view of a container with a second connecting arrangement of the proposed connecting system in the first embodiment.

FIG. 15 shows a schematic perspective view of a first connecting arrangement 3A with a severing element 7 arranged on the opening region 4A. In the embodiment shown in FIG. 15 the severing element 7 has four or (in dashed lines) three legs, but may also have more legs 19. The legs 19 are preferably wedge-shaped at least partially or in areas or have cutting edges remote from the opening region 4A. The severing element 7 preferably has a point 20 which is directed away from the opening region 4A. The point 20 preferably adjoins the legs 19 or vice versa. By means of the point 20 and/or the legs 19, shear forces can be increased and the destruction or perforation of the opening region 3B can be facilitated. However, other alternative embodiments for the severing element 7 are theoretically possible.

In the embodiment shown, the severing element 7 comprises preferably foot-like connecting portions 21 with the opening region 4B. These may be configured to derive or distribute a force exerted by the severing element 7, particularly the point 20 or the legs 19, onto the opening region 4A. Alternatively or additionally, the connecting portions 21 may be provided and arranged so that when the connecting arrangements 3A, 3B are pushed inside one another the mouth-shaped portion 5B comes to bear on the connecting portions 21 or in the vicinity thereof, as a result of which the shear forces acting on the opening region 4B can be generated or increased. This assists with the opening of the opening region 4A.

The severing element 7 is preferably arranged and/or configured for piercing, severing, cutting or destroying the opening region 4A, 4A' of the first connecting arrangement 3A, 3A'.

The severing element 7 is preferably arranged and/or fastened on the opening region 4B, 4B' of the second connecting arrangement 3B, 3B', particularly directly. Alternatively, or additionally, the severing element 7 is configured to concentrate a force acting on the opening region 4A, 4A' and/or to distribute a force or counter-force acting on the opening region 4B, 4B' such that the opening region 3B of the second connecting arrangement 3B, 3B' remains intact when the opening region 4A, 4N is opened by destruction thereof by means of the severing element 7.

In another aspect it is envisaged that the severing element 7 comprises one or more connecting portions 21 to which or with which the severing element 7 is connected, preferably by material engagement, with the opening region 4A, 4A', 4B, 4B'.

The connecting portions 21 preferably form frangible points for the opening region 4B, 4B' of the second connecting arrangement 3B, 3B'. Preferably, the connecting portions 21 are arranged to correspond to the first connecting arrangement 3A, 3A', particularly the mouth-shaped portion 5A, 5A' thereof. Moreover, the connecting portions 21 are preferably configured so that forces acting on the opening region 4B, 4B' of the second connecting arrangement 3B, 3B' are concentrated by the first connecting arrangement 3A, 3A'. This makes it easier to destroy and/or open the opening region 4B, 4B' of the second connecting arrangement 3B, 3B' by means of the first connecting arrangement 3A, 3A', particularly the mouth-shaped portion 5A, 5A' thereof.

FIG. 16 shows the proposed container system in a transporting position or orientation. The containers B1, B2, B3 are preferably releasably connectable to one another for transporting as a result of a portion or bottle neck F1, F2 of a container B1, B2, B3 that forms the removal opening being adapted to be held by the holding device of the cap-like cover device 6.

The first container B1 is preferably provided with the cover device 6 or the first connecting arrangement 3A, 3A' is covered by the cover device 6. The second container B2 is received and/or held by the cover device 6, preferably in or by means of the region of its removal opening E2 or its bottle neck F2. In this way or by some other means, the containers B1, B2 of the container system may form a kit or a combination which associates the containers B1, B2 with one another. This advantageously makes it possible to avoid unintended combinations of containers B1, B2 or substances S1, S2.

The cover device 6 can preferably be held on the first container B1 and is configured to hold both the region of the removal opening E1, E2 or the bottle neck F1, F2 of the first container B1 and also of the second container B2. In this way the cover device 6 has a triple function, namely for providing a (sterile) cover, for forming a transport combination and as a support foot. The latter will be discussed further hereinafter.

FIG. 17 shows the first container B1 in longitudinal section, the first connecting arrangement 3A being covered, preferably in sterile manner, by the cover device 6. The cover device 6 may be removably held on the container B1 by means of or using one of the securing devices 10A, 10B or by some other means on the first container B1.

One or both opening regions 4A, 4A', 4B, 4B' are preferably covered in sterile or sterilizable manner One of the opening regions 4A, 4A', 4B, 4B' is preferably separated from the environment in sterile manner by the cap-like cover device 6. An (another) opening region 4A, 4A', 4B, 4B' is preferably separated from the environment in sterile or sterilizable manner by a removable, detachable, tear-off and/or film-like closure 14.

A double closure may be formed by the respective opening region 4A, 4A', 4B, 4B' and the respective sterile or sterilizable cover. In this way, a sterile or sterilizable or sterile sealed region or space or cavity can be formed between the sterile or sterilizable cover and the respective connecting arrangement 3A, 3A, 3B, 3B'.

The sterile or sterilizable cover is preferably removable. This makes it possible to produce a (sufficiently) sterile fluidic connection 2 through the connecting system 1, by removing the covers and using the opening regions 4A, 4A', 4B, 4B' arranged in the sterile area to form the fluidic connection 2.

In the embodiment shown, the cap-like cover device 6 forms a sterile cover for the first opening regions 4A, 4A' and/or the closure 14 forms a sterile cover for the second opening region 4B, 4B' by means of a sealed or welded-on or otherwise tightly applied film. Theoretically, however, the sterile covering may also be provided by other means, for example by replacing the film with a cap or a (screw) closure, optionally with a seal or the like, and/or by constructing the cover device 6 without holding means or with a different holding device.

Sterile in the sense of the present invention denotes, in particular, at least substantially germ-free or aseptic. A sterile or sterilizable cover is preferably a device designed to prevent the penetration of germs, particularly by forming a germproof barrier.

From the construction point of view, a sterile or sterilizable cover is preferably tightly applied or connected to the respective connecting arrangement 3A, 3A', 3B, 3B' so as to form a germproof barrier.

A cover is sterilizable particularly when the cover uses materials, or the sterile or sterilizable cover comprises or is formed from materials, which are suitable for the use of at least one method of sterilization known in the prior art for destroying germs. For example, such materials may be sterilized by one of the known sterilization methods without being damaged thereby or losing their function as a barrier against the ingress of germs. The known sterilization methods include irradiation, particularly with gamma rays or an electron beam, gassing, treatment with hot air or autoclaving. Preferably, the connecting arrangements 3A, 3A', 3B, 3B' are also sterile or sterilizable.

The opening regions 4A, 4A', 4B, 4B' are preferably produced independently of one another or separately from one another in an initial state and/or are covered in sterile or sterilizable manner separately from one another. This enables the containers B1, B2, B3 to be used separately.

Between the opening region 4A, 4A', 4B, 4B' and the sterile or sterilizable cover or means for sterile covering, particularly the cover device 6 and/or the closure 14, a space is preferably formed which is sterilized, sterilizable and/or sealed in sterile manner in an initial state or sealed off to be airtight and/or germproof.

According to another aspect of the present invention which can also be implemented independently, a substance, particularly an active substance, vaccine and/or adjuvant is arranged, attached and/or immobilized in the space. In particular, the substance is arranged in a lattice in the space and/or held by the severing element 7.

In a preferred aspect the severing element 7 or another part of one of the connecting arrangements can be dissolved, solubilized and/or suspended within the space. In this way, after the fluidic connection 2 has been made, the substance from the space may form part of the mixture of substances S1, S2, S3.

The substance arranged in the space may be dissolved and/or solubilized and/or suspended on the connecting arrangement 3A, 3B, 3A', 3B' or on the opening region 4A, 4A', 4B, 4B' by means of one of the substances S1, S2, S3.

In a preferred aspect, a lyophilisate is dried onto or otherwise applied to the opening region. The lyophilisate as well as one or more of substances S1, S2, S3 may contain vaccine, active substance, and/or adjuvant for preparing a vaccine or combined vaccine. In this way, after the production of the fluidic connection 2, the substance arranged in the space may form a component of a substance mixture, particularly a combined vaccine.

The means for sterile covering, particularly the cover device 6 and/or the closure 14, are preferably removable or detachable, particularly manually or without the use of tools, so that the opening regions 4A, 4A', 4B, 4B' are accessible for producing the fluidic connection 2.

One of the containers B1, B2, B3 preferably comprises, on a side remote from the removal opening E1, E2, the removable cap-like cover device 6 which in a starting position closes off the connecting arrangement 3A, 3A', 3B, 3B', preferably in sterile manner.

The cap-like cover device 6 preferably comprises a holding device for a removal opening E1, E2 or a bottle neck F1, F2. A holding device, particularly the receptacle 13, is preferably configured for holding a portion of a container B1, B2, B3, particularly the bottle neck F1, F2, forming the removal opening E1, E2, E3.

The cover device 6 preferably comprises a holding portion which is shaped like a shoulder and/or to correspond to or complement a shoulder region of the container B1, B2 adjacent to the removal opening E1, E2.

In the embodiment shown the cover device 6 preferably comprises the receptacle 13 which is configured to receive and/or retain, preferably by interlocking or latching engagement, the bottle neck F1, F2 of the container or containers B1, B2.

The cover device 6 is preferably embodied as a holder or stand for the container or containers B1, B2. For this purpose, the removal opening E1, E2 or the bottle neck F1, F2 can preferably be inserted in the cover device 6. In particular, the receptacle 13 is configured for clamping and/or latching and/or releasably holding the container or containers B1, B2, preferably in the region of the removal opening E1, E2 and/or the bottle neck F1, F2. This advantageously allows reliable operation as a foot or stand and/or for holding or forming the kit or combination of containers B1, B2, particularly bottles, of the container system B.

The cover device 6 preferably serves as a base or standing surface for one of the containers B1, B2, particularly the first container B1, if its opening region 4A is covered by the cover device 6. It may be provided that the receptacle 13 is arranged at the bottom in a starting position and/or is accessible from outside. This has the additional advantage that the containers B1, B2 can be stacked by placing the first container B1 comprising the cover device 6 with the receptacle 13 onto the second container B2 in such a way that its removal opening E2 or bottle neck F2 is pushed into the receptacle 13 and preferably held, particularly by latching and/or clamping. In this way a kit can be produced in which the containers B1, B2 are releasably joined together, thus helping to prevent incorrect packing and erroneous mixing of substances using the connecting system 1.

Figure 18:
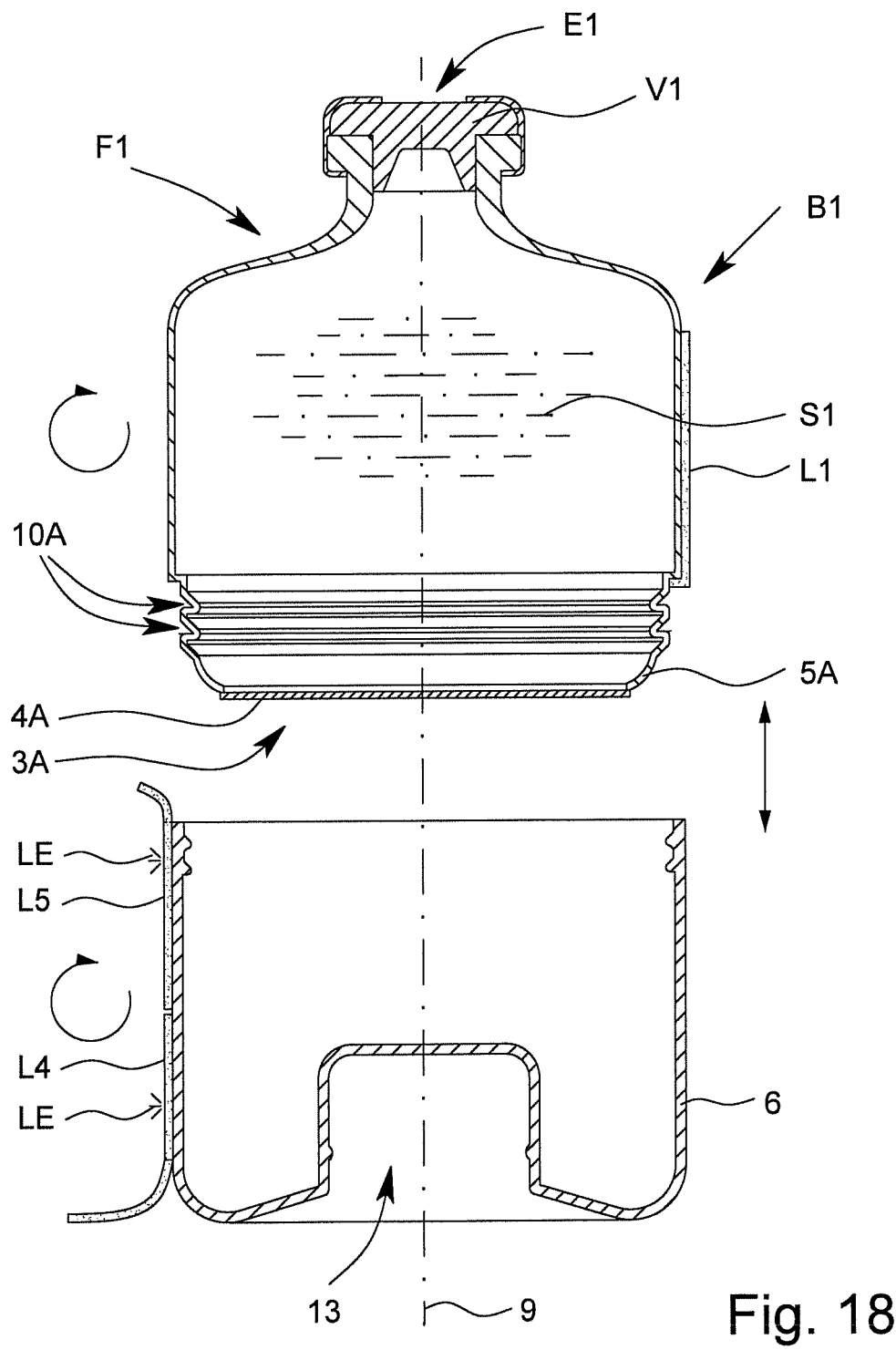
FIG. 18 shows a schematic longitudinal section through the first container according to FIG. 17 with the cover device removed.

For using the proposed connecting system 1 it may be envisaged that first of all the cover device 6 is separated or removed from the first container B1 (cf. FIG. 18).

Figure 19:
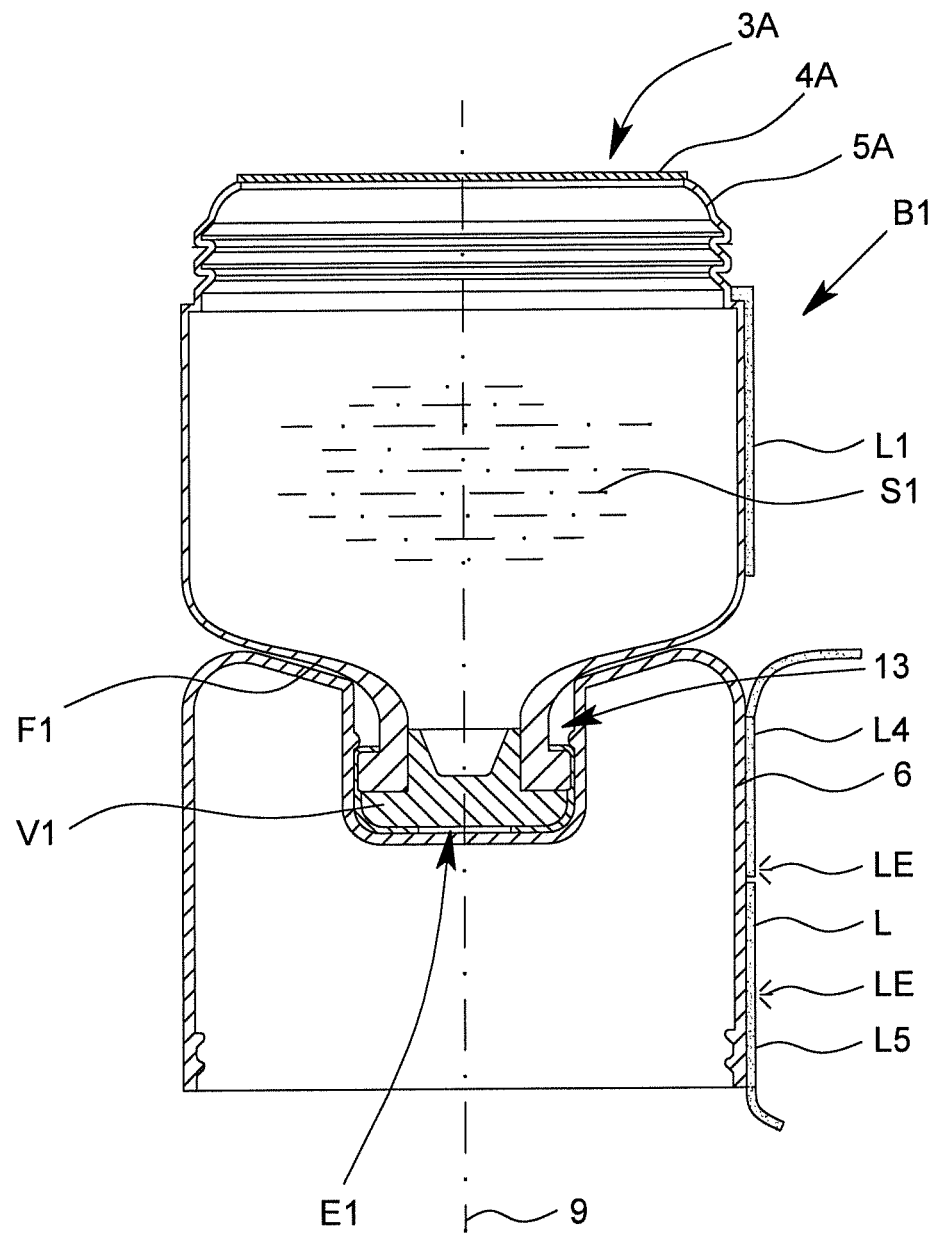
FIG. 19 shows a schematic longitudinal section through the first container held like a foot in the cover device according to FIG. 17.

As shown in FIG. 19, by way of example, the first container B1 (or alternatively the second container B2) is then preferably inserted with the removal opening E1, E2 or the bottle neck F1, F2 or a part thereof in the receptacle 13 of the cover device 6. For this purpose the cover device 6 may be used with the opening of the receptacle 13 directed upwards in the position of use, the removal opening E1, E2 or the bottle neck F1, F2 being pushed into the receptacle 13 at least partially from above in the position of use. Theoretically, however, it is also possible to insert the container B1, B2 into the receptacle 13 in other positions. Preferably, the cover device 6 is then used as a holder or foot or at the bottom in the position of use. Thus the first connecting arrangement 3A or its opening region 4A is accessible from above in the position of use.

The cover device 6 can be used as a standing foot for the container B1, B2, B3 if the container B1, B2, B3 is held by the holding device or receptacle 13 with the portion forming the removal opening E1, E2 or the bottle neck F1, F2.

The cover device 6 thus preferably forms a holder or foot for the container B1, B2 which is held by the cover device 6. The dual function of the cover device advantageously saves space and material and additionally using the cover device 6 as a holder or foot advantageously prevents contamination of the connecting arrangements 3A, 3A', 3B, 3B'.

The cover device 6 is preferably of cap-like formation and in a starting or transporting position it forms a tight seal with the connecting arrangement 3A, 3A', 3B, 3B', so as to produce a sterile or sterilizable closure.

The cover device 6 preferably comprises the receptacle 13 and a holding portion for holding onto the connecting arrangement 3A, 3N, 3b, 3B' on different sides, particularly opposite sides. The holding portion may have a region which is releasably fixed or fixable to the connecting arrangement 3A, 3A', 3b, 3B' by a clamping and/or latching action. For this purpose the cover device 6 in the holding portion and the connecting arrangement 3A, 3A', 3b, 3B' may be of complementary or corresponding construction.

The cover device 6 is preferably made of plastics or contains plastics. The cover device 6 is preferably a thermoformed part or an injection molded part and/or a shaped part produced from a sheet material. The cover device 6 preferably has a wall thickness of more than 1 mm and/or less than 2 mm. However, other solutions are also possible here.

In the embodiment shown, the cover device 6 is essentially in the shape of a W or U in longitudinal section, with an indentation in the curve of the U which forms the receptacle 13. In principle, however, the cover device 6 may also be formed differently for the dual function of a sterile closure on the one hand and a holding device on the other.

Figure 20:
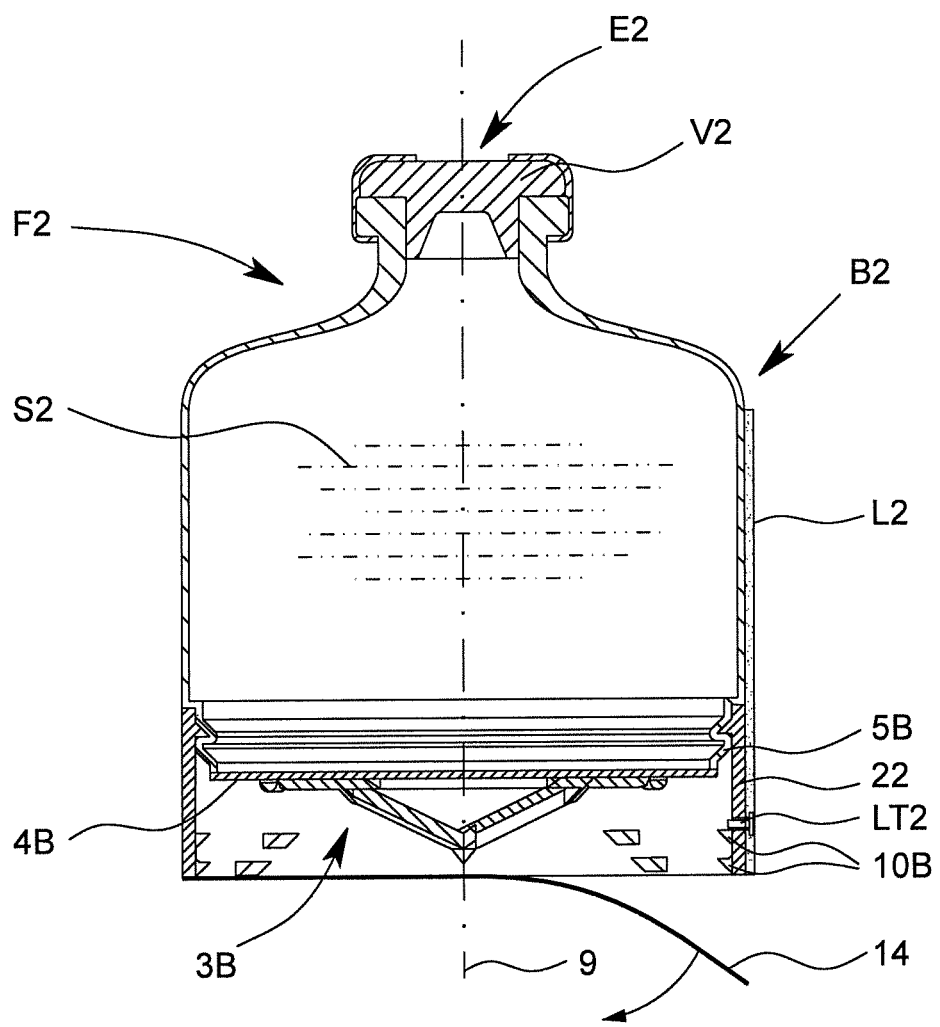
FIG. 20 shows a schematic longitudinal section through the second container with the closure partially removed.

FIG. 20 shows the second container B2 in which the opening region 4B is closed off, particularly in sterile manner, by the closure 14, particularly a removable cover, film, sealing film or the like. Preferably the closure 14 is removable, particularly by pulling off, in order to use the proposed connecting system 1. The closure 14 may have a tab for this purpose.

At least one of the connecting arrangements 3A, 3A', 3B, 3B', specifically the second connecting arrangement 3B, 3B' in the embodiment shown, preferably has a receptacle for another one of the connecting arrangements 3A, 3N, 3B, 3B' which may preferably be formed by a collar-like portion 22 or alternatively or additionally by some other means. The collar-like portion 22 may assist with fitting the connecting arrangements 3A, 3A', 3B, 3B' into one another, guide the required movement and/or protect the connecting arrangements 3A, 3A', 3B, 3B' at the sides. It preferably comprises the securing devices 10A, 10B or parts thereof.

Preferably, one of the connecting arrangements 3A, 3A', 3B, 3B', particularly the second connecting arrangement 3B, 3B', is surrounded by the collar-like portion 22 in the (first and/or second) connecting position.

The collar-like portion 22 preferably serves to receive the (respectively) other connecting arrangement 3A, 3N, 3B, 3B' or to form a receptacle and/or guide, preferably a linear guide for this purpose, particularly in the direction of the central axis or axis of symmetry 9.

In the embodiment shown the collar-like portion 22 is provided on or around the second connecting arrangement 4B, 4B' or on the second container B2. Alternatively or additionally, however, the collar-like portion 23 may also be provided around the first connecting arrangement 4A, 4A' or on the first container B2.

The collar-like portion 22 is preferably fixedly, rigidly and/or non-rotationally connected to a or the associated connecting arrangement 3A, 3A', 3B, 3B', preferably by interlocking engagement, particularly by latching, and/or by frictional engagement, particularly by clamping, and/or by material connection, particularly by adhesive bonding or injection molding, but alternatively also by being formed in one piece with one of the connecting arrangements 3A, 3N, 3B, 3B' or containers B1, B2.

The collar-like portion 22 preferably projects beyond the mouth-shaped portion 5A, 5B, 5A', 5B' and/or extends at least partially parallel thereto or in the same direction and preferably thereby forms the receptacle or linear guide for the other one of the connecting arrangements 3A, 3N, 3B, 3B'.

The collar-like portion 22 or the receptacle that may be formed by it preferably at least partially comprises the guide 18A, 18B, particularly the slide, a guide pin or the like.

An open edge of the collar-like portion 22 preferably forms a stop for those of the connecting arrangements 3A, 3A', 3B, 3B' which it does not surround in the separated state of the connecting arrangements 3A, 3A', 3B, 3B' and/or for the container B1 connected thereto. Preferably in the second connecting position the connecting arrangements 3A, 3A', 3B, 3B' abut on one another in the region of the stop.

The collar-like portion 22 is preferably closed off, particularly in sterile manner, at one end or on an open side by the closure 14, particularly a film applied as a seal.

Figure 21:
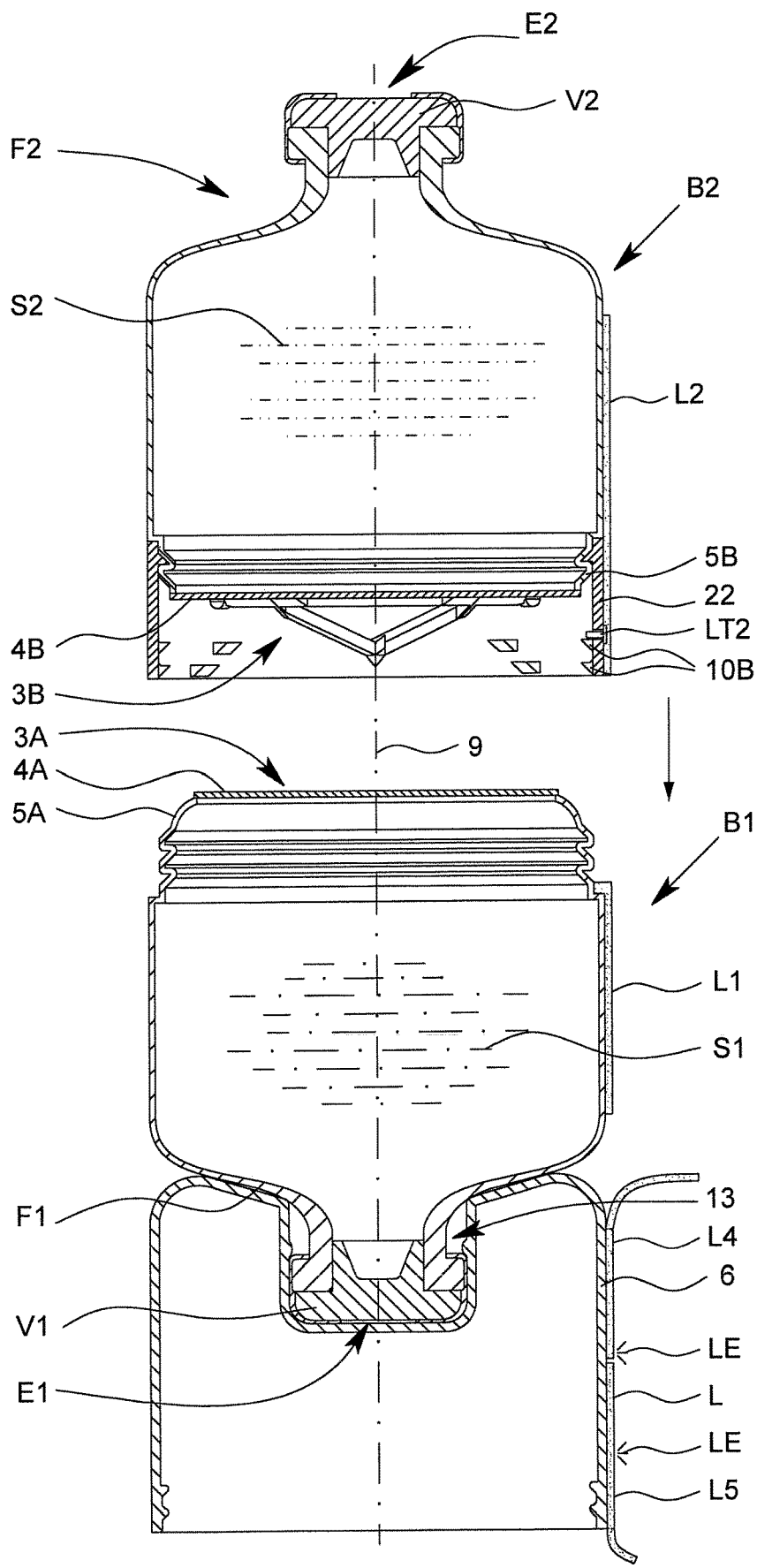
FIG. 21 shows a schematic longitudinal section through the proposed container system, indicating the direction of movement for providing the fluidic connection with the proposed connecting system.

FIG. 21 shows by way of example how the containers B1, B2 can be fluidically connected to one another by the proposed connecting system 1. For this purpose the closure 14 is preferably removed from the second container B2 and the second container B2 is then placed with the second connecting arrangement 3B, 3B' onto the first connecting arrangement 3A, 3A' from above. In the embodiment shown the first connecting arrangement 3A, 3A' extends into the receptacle formed by the collar-like portion 22.

Then the opening regions 4A, 4A', 4B, 4B' are opened. By combining the connecting arrangements 3A, 3B, which form, in particular, base regions of the bottles or bottle-like containers B1, B2, the fluidic connection 2 can be produced, as already explained in relation to FIGS. 2 to 8. FIG. 21 shows the first embodiment but the same also applies to the second embodiment and the combination of embodiments.

According to another aspect of the present invention which can also be implemented independently, the connecting system 1 or the connecting arrangements 3A, 3B, 3A', 3B' are specific to a particular size of container.

In particular, a proposed container system B comprises containers B1, B2, B3 of different sizes, volumes and/or with specific quantities of substance S1, S2, S3 for producing a desired mixing ratio. For this it is preferable for the connecting arrangements 3A, 3B, 3A', 3B' to be selectively configured (mechanically) such that containers B1, B2, B3 with compatible contents can be connected and containers B1, B2, B3 with incompatible contents, or containers B1, B2, B3 which would lead to an undesirable or unsuitable mixing ratio if a fluidic connection 2 were produced, have connecting arrangements 3A, 3B, 3A', 3B' which are mechanically incompatible with one another.

Particularly preferably, the connecting arrangements 3A, 3B, 3N, 3B' may be constructed selectively with respect to one another, particularly according to the lock and key principle. This can be achieved using guides 18A, 18B, guiding slides, diameters or the like which are compatible or incompatible with one another, respectively.

The aspects of the present invention described in connection with FIGS. 16 to 21 may be advantageous on their own and in various combinations, preferably wholly or partially or in certain details in the sequence of the explanations. In particular, the cover device 6 is preferably removed and used as a holder or foot before the second connecting arrangement 3B is opened or unsealed, particularly by removal of the closure 14.

Moreover, FIGS. 16 to 21 show the connecting arrangements 3A, 3B of the first embodiment. Instead of these, however, it is also possible to use the connecting arrangements 3N, 3B' of the second embodiment or a combination of the first connecting arrangements 3A, 3N and the second connecting arrangements 3B, 3B'. The aspects explained then apply accordingly.

The fluidic connection 2 may thus alternatively or additionally be produced by deformation. In this case the severing element 7 is optional and the collar-like portions 22 are preferably non-round in cross section, so that when the connecting arrangements 3A, 3B, 3A', 3B' are rotated relative to one another the fluidic connection 2 is produced by shaping or deformation. In the interests of clarity, the corresponding procedure will not be repeated here.

Further aspects of the present invention which may be implemented separately and combined with one another and/or may be implemented with aspects and features of the present invention as explained hereinbefore and which are advantageous will be described in more detail hereinafter.

An aspect of the present invention which can be implemented independently, or in conjunction with one or more of the preceding aspects, relates to a connecting system 1 for producing a fluidic connection 2, preferably between containers B1, B2, B3, wherein the connecting system 1 comprises at least two connecting arrangements 3A, 3A', 3B, 3B' configured to form the fluidic connection 2, namely a first connecting arrangement 3A, 3A' and a second connecting arrangement 3B, 3B', which, in an initial state, are each fluidically sealed and are sealed independently of one another, the connecting arrangements 3A, 3A', 3B, 3B' being capable of insertion in one another and/or being adapted to be inserted in one another by a preferably at least substantially linear and/or axial movement along a common axis, by means of which at least one of the connecting arrangements 3A, 3N, 3B, 3B' can be opened.

In particular, the fluidic connection 2 is formed by an insertion process. This is advantageously carried out, for example, by producing the fluidic connection 2 particularly quickly and reliably, in particular without the need for repeated rotation of the connecting arrangements 3A, 3N, 3B, 3B' by means of a helical line with a number of turns or by means of a thread.

The insertion of the connecting arrangements 3A, 3A', 3B, 3B' into one another also allows the connecting arrangements 3A, 3N, 3B, 3B' to be brought together in a manner oriented with one another in relation to the position of rotation about the (common) axis of symmetry or central axis 9, which is particularly advantageous if the mouth portions 5A, 5A', 5B, 5B' of the connecting arrangements 3A, 3A', 3B, 3B' are non-round in cross section or the opening of at least one of the connecting arrangements 3A, 3A', 3B, 3B' is produced by deformation and the resultant tensioning of an opening region 4A, 4N, 4B, 4B'.

An aspect of the present invention which can also be implemented independently or in conjunction with one or more of the preceding aspects relates to a connecting system 1 for producing a fluidic connection 2, preferably between containers B1, B2, B3, wherein the connecting system 1 comprises at least two connecting arrangements 3A, 3A', 3B, 3B' configured to produce the fluidic connection 2, namely a first connecting arrangement 3A, 3A' and a second connecting arrangement 3B, 3B', which are fluidically sealed off in a starting state, the first connecting arrangement 3A, 3A' having an in particular film-like, brittle and/or unstable opening region 4A, 4A', 4B, 4B', being deformable outside the opening region 4A, 4A', 4B, 4B' and being configured so that the deformation causes opening of the first connecting arrangement 3A, 3A', 3B, 3B' in the opening regions 4A, 4A', 4B, 4B'.

An aspect of the present invention which can also be implemented independently, or in conjunction with one or more of the preceding aspects, relates to one or more containers B1, B2, B3 or vessels which comprise connecting arrangements 3A, 3A', 3B, 3B' in each case.

An aspect of the present invention which can also be implemented independently or in conjunction with one or more of the preceding aspects relates to a connecting system 1 for producing a fluidic connection 2, preferably between containers B1, B2, B3, the connecting system 1 having at least two connecting arrangements 3A, 3A', 3B, 3B' configured to produce the fluidic connection 2, the connecting arrangements 3A, 3A', 3B, 3B' each comprising an opening region 4A, 4A', 4B, 4B' which is fluidically closed in a starting state, particularly in the manner of a film, or is brittle, fragile and/or unstable, the opening regions 4A, 4A', 4B, 4B' each being covered in sterile or sterilizable manner.

In particular, the opening or formation of the fluidic connection 2 is thus achieved by the fact that the opening region 4A, 4A' of the first connecting arrangement 3A, 3A' is or forms a frangible point, so that deformation of the first connecting arrangement 3A, 3A', particularly by tensioning, leads to tearing or breaking of the opening region 4A, 4A'. This has the particular advantage that no point or other severing element is required for this opening process. Severing elements 7 usually have to be sharp-edged and stabilized to allow the opening up of an opening region 4A, 4A', 4B, 4B'. Consequently, by avoiding such a severing element, the manufacturing process can use gentler materials and/or be simpler. As already explained hereinbefore, however, a combination of the above aspects using a severing element 7 is also possible, while the present aspect is advantageous for enlarging or expanding an opening or the fluidic connection 2.

The sterile or sterilizable covers of the opening regions 4A, 4A', 4B, 4B' advantageously make it possible to produce the fluidic connection 2 while excluding germs or other foreign substances, particularly in the pharmaceutical/medical sector. Alternatively, or additionally, the sterile or sterilizable covering of the opening regions 4A, 4A', 4B, 4B' offers the possibility of using containers B1, B2, B3 with the connecting arrangement 3A, 3A', 3B, 3B' separately from one another in this environment and optionally in combination with one another.

One aspect of the present invention which can also be implemented independently or in conjunction with one or more of the preceding aspects relates to a container system B with at least two containers B1, B2, B3, preferably bottles, and the connecting system 1, wherein the containers B1, B2, B3 for providing a fluidic connection 2 between the containers B1, B2, B3 in each case comprise at least one connecting arrangement 3A, 3A', 3B, 3B' of the connecting system 1.

In this connection, the use of the proposed connecting system 1 for connecting containers B1, B2, B3 has proved advantageous particularly because it is possible to produce a non-releasable and/or irreversible fluidic connection 2 between the containers B1, B2, B3, thus ensuring complete mixing of the contents of the containers B1, B2, B3.

Another aspect of the present invention which can also be implemented independently or in conjunction with one or more of the preceding aspects relates to a container system B with at least two containers B1, B2, B3, preferably bottles, each of which comprises a removal opening E1, E2, preferably each closed off by a septum, while preferably the containers B1, B2, B3 comprise, on a side remote from the respective removal opening E1, E2, particularly on the base of the respective bottle, a connecting arrangement 3A, 3A', 3B, 3B' for providing a fluidic connection 2 between the containers B1, B2, B3 and/or are configured for providing a fluidic connection 2 between the containers B1, B2, B3.

The use of two containers B1, B2, B3, each of which comprises a removal opening E1, E2 and a connecting arrangement 3A, 3A', 3B, 3B', is particularly advantageous because the containers B1, B2, B3 can also be used separately from one another, but at the same time, in the event of joint use by means of the connecting arrangements 3A, 3A', 3B, 3B', a fluidic connection with a relatively large cross-section is made possible for the rapid or accelerated mixing of the contents of the containers B1, B2, B3.

Another aspect of the present invention which can also be implemented independently or in conjunction with one or more of the preceding aspects relates to a method for providing a fluidic connection 2 between connecting arrangements 3A, 3A', 3B, 3B' and/or containers B1, B2, B3 by means of the connecting arrangements 3A, 3A', 3B, 3B', wherein in an initial state the connecting arrangements 3A, 3A', 3B, 3B' are in each case fluidically sealed, wherein a first connecting arrangement 3A, 3A' is opened by another, second connecting arrangement 3B, 3B' and the second connecting arrangement 3B, 3B' is opened by the by the first connecting arrangement 3A, 3A', thus producing a continuous fluidic connection 2 between the connecting arrangements 3A, 3N, 3B, 3B'.

This results in corresponding advantages, i.e., in particular, a rapid and reliable formation of the fluidic connection 2 or mixing of the substances S1, S2, S3.

Another aspect of the present invention which can also be implemented independently or in conjunction with one or more of the preceding aspects relates to a use of a container system B, wherein a first container B1 holds a first substance S1, particularly a first vaccine against a first disease, while a second container B2 holds a second substance S2, particularly a second vaccine against a second disease different from the first, for the preparation of a mixture of substances, particularly for the preparation of a combined vaccine for simultaneous immunization against different diseases, wherein the containers B1, B2, B3 are fluidically connected to one another by means of the connecting arrangements 3A, 3A', 3B, 3B', so that the substances are mixed together, particularly to form the combined vaccine.

The use of the proposed connecting system 1 or container system B for the preparation of combined vaccine is advantageous for example because the vaccines may be used individually or in combination, as desired. The proposed connecting system 1 or container system B offers the flexibility of deciding on the spot whether the substances S1, S2, S3 or vaccines are to be administered individually or in combination. This advantageously avoids subjecting animals to stress by an unnecessarily large number of separate injections or unnecessarily always having to vaccinate them with a combined vaccine, even when there is no need for one of the vaccines to be given, because of an existing immunity. In this way, the present invention can save materials and costs.

Another aspect of the present invention which can also be implemented independently or in conjunction with one or more of the preceding aspects relates to a method for providing a fluidic connection 2 between connecting arrangements 3A, 3A', 3B, 3B' and/or containers B1, B2, B3 by means of connecting arrangements 3A, 3A', 3B, 3B' of the connecting system 1, wherein preferably the means for sterile covering, particularly the cover device and/or the closure 14, is removed from the opening regions 4A, 4A', 4B, 4B' in each case and the still closed opening regions 4A, 4N, 4B, 4B' thus exposed are opened up to form the fluidic connection 2.

Another aspect of the present invention which can also be implemented independently or in conjunction with one or more of the preceding aspects relates to a method for providing a fluidic connection 2 between connecting arrangements 3A, 3A', 3B, 3B' and/or containers B1, B2, B3 by means of the connecting arrangements 3A, 3A', 3B, 3B', wherein in an initial state the connecting arrangements 3A, 3A', 3B, 3B' are in each case fluidically sealed, while a first connecting arrangement 3A, 3A' is opened by another second connecting arrangement 3B, 3B' and the second connecting arrangement 3B, 3B' is opened by the first connecting arrangement 3A, 3A', thus producing a continuous fluidic connection 2 between the connecting arrangements 3A, 3A', 3B, 3B'.

In another aspect which may thus be implemented independently, the present invention relates to a kit with two proposed containers B1, B2, B3 or with containers B1, B2, B3, which can be fluidically connected to one another by means of the connecting system 1, so that a mixture of the substances S1, S2, S3 contained in the containers B1, B2, B3 can be formed. This prevents other, incompatible substances S1, S2, S3 from being mixed.

A kit in the sense of the present invention is particularly a combination and/or system comprising the first container B1 and the second container B2, which form the components of the kit. The kit may also comprise the third container B3 and/or further containers or components.

The components of the kit are preferably marketed as a set, particularly in a joint pack or the like. However, it is also possible for the components to form a loose combination to be used together. A common or connecting component may be provided, for example a common set of instructions for use, handling recommendations, information in the text on one or more of the components of the kit or the like.

Preferably, the containers B1, B2, B3 form a kit by being held together, particularly preferably by means of the cover device 6 or the receptacle 13.

The containers B1, B2, B3 are preferably designed for the preparation of a combined vaccine for simultaneous immunization against different diseases, preferably by making the containers B1, B2, B3 capable of fluidic connection to one another by means of the connecting arrangements 3A, 3A', 3B, 3B', so that substances S1, S2, S3 located in the containers B1, B2, B3 are mixed together to form the combined vaccine, while in particular the substances S1, S2, S3 can be removed through the removal opening E1, E2 separately from one another and then used, particularly before or without forming the fluidic connection 2.

Preferably, at least one of the containers B1, B2, B3 comprises a removal opening E1, E2, preferably closed off with a septum, while the container B1, B2, B3 is preferably configured, on a side remote from the removal opening E1, E2, particularly on the bottom of the bottle, for providing a fluidic connection 2 between the containers B1, B2, B3 and/or comprises the connecting arrangement 3A, 3A', 3B, 3B'.

The containers B1, B2, B3 are preferably fluidically connected to one another by means of the connecting arrangements 3A, 3A', 3B, 3B', so that the substances are mixed together, preferably forming a combined vaccine.

In another aspect which may thus be implemented independently, the present invention relates to the use of a connecting system 1, kit or container system B as proposed, for the preparation or provision of medicaments for live animals, preferably mammals, and/or for medical uses.

In another aspect which may thus be implemented independently, the present invention relates to the use of a connecting system 1, kit or container system B as proposed, for the preparation and/or provision of a vaccine, particularly for immunizing against the disease(s) Porcine Circovirus Disease "PCVD" and/or Enzootic Pneumonia "EP" or infections with Porcine Circovirus and/or infection with bacteria of the *Mycoplasma* strain, particularly *Mycoplasma hyopneumoniae*, preferably for immunizing against the diseases Porcine Circovirus Disease "PCVD" and Enzootic Pneumonia "EP" or against infections with Porcine Circovirus and/or infection with bacteria of the *Mycoplasma* strain, particularly *Mycoplasma hyopneumoniae*.

For this purpose, a first proposed container B1 contains as the first substance S1 a first reactant and a second proposed container B2 contains as the second substance S2 a second reactant. The reactants may be vaccines against different diseases or the educts may contain vaccines against different diseases.

It is particularly preferable for the first reactant to contain only a first one of the components *Mycoplasma* vaccine or *Mycoplasma* antigen and Circovirus vaccine or Circovirus antigen (and optionally other substances). The first reactant may thus contain either *Mycoplasma* vaccine, or one or more *Mycoplasma* antigens or alternatively Circovirus vaccine or one or more Circovirus antigens. The first reactant is preferably stored separately from the second reactant, particularly if the reactants are not stable in the long term together. The second reactant preferably contains only the other one of the components *Mycoplasma* vaccine or one or more *Mycoplasma* antigens and Circovirus vaccine or one or more Circovirus antigens (and optionally other substances). If the first reactant thus contains *Mycoplasma* vaccine or one or more *Mycoplasma* antigens, the second reactant contains Circovirus vaccine or one or more Circovirus antigens, or vice versa.

The *Mycoplasma* vaccine may contain attenuated and/or inactivated bacteria, fragments of bacteria or recombinantly prepared parts of *Mycoplasma hyopneumoniae*, but at least one or more *Mycoplasma hyopneumoniae* antigens. Preferably, the *Mycoplasma hyopneumoniae* antigen originates from the *Mycoplasma hyopneumoniae* J-strain or the inactivated *Mycoplasma hyopneumoniae* bacteria are those of the J-strain. Moreover, the *Mycoplasma* vaccine may be one of the following vaccines or the *Mycoplasma hyopneumoniae* antigen may be the antigen or antigens contains in one of the following vaccines: Ingelvac® MycoFlex (Boehringer Ingelheim Vetmedica Inc, St Joseph, Mo., USA), Porcilis M. hyo, Myco Silencer® BPM, Myco Silencer® BPME, Myco Silencer® ME, Myco Silencer® M, Myco Silencer® Once, Myco Silencer® MEH (all from Intervet Inc., Millsboro, USA) Stellamune *Mycoplasma* (Pfizer Inc., New York, N.Y., USA), Suvaxyn *Mycoplasma*, Suvaxyn M. hyo, Suvaxyn MH-One (all formerly Fort Dodge Animal Health, Overland Park, Kans., USA (now Pfizer Animal Health).

The Circovirus vaccine may contain attenuated and/or inactivated porcine Circovirus, preferably type 2, particularly type 2 ORF2 protein. It is particularly preferable to use recombinantly expressed ORF2 protein of the Porcine Circovirus type 2, preferably expressed in and obtained from in vitro cell culture. Examples of ORF2 proteins of the Porcine Circovirus type 2 are described inter alia in International Patent Application WO2006-072065. These have proved particularly advantageous for effective vaccination. Moreover, the Circovirus vaccine may be one of the following vaccines, or the Circovirus antigen may be the antigen or antigens contained in one of the following vaccines: Ingelvac® CircoFLEX, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA).

The Circovirus vaccine, if it contains the ORF2 protein, preferably contains between 2 μg and 150 μg, preferably between 2 μg and 60 μg, more preferably between 2 μg and 50 μg, more preferably between 2 μg and 40 μg, more preferably between 2 μg and 30 μg, more preferably between 2 μg and 25 μg, more preferably between 2 μg and 20 μg, more preferably between 4 μg and 20 μg, more preferably between 4 μg and 16 μg of ORF2 protein per dose to be administered. The Circovirus vaccine is preferably prepared or formulated so that 1 ml of the vaccine corresponds to a dose of 1. In particular, the Circovirus vaccine may contain ORF2 protein in amounts of more than 2 μg/ml, preferably more than 4 μg/ml and/or less than 150 μg/ml, preferably less than 60 μg/ml, 50 μg/ml, 40 μg/ml, 30 μg/ml or 25 μg/ml, particularly less than 20 μg/ml. This contributes to reliability of administration.

The *Mycoplasma* vaccine, if it contains inactivated *Mycoplasma* bacteria, preferably inactivated *Mycoplasma hyopneumoniae* bacteria, preferably contains between $10^3$ and $10^9$ colony forming units (CFU), preferably between $10^4$ and $10^8$ (CFU), more preferably between $10^5$ and $10^6$ (CFU) per dose to be administered, the corresponding CFU being adjusted before the inactivation of the bacteria. The *Mycoplasma* vaccine is preferably prepared or formulated so that 1 ml of the vaccine corresponds to a dose of 1. In particular, the *Mycoplasma* vaccine may contain more than $10^3$ CFU/ml, preferably more than $10^4$ CFU/ml, particularly more than $10^5$ CFU/ml and/or less than $10^9$ CFU/ml, preferably less than $10^8$ CFU/ml, particularly less than $10^7$ CFU/ml or $10^6$ CFU/ml of inactivated *Mycoplasma* bacteria, preferably inactivated *Mycoplasma hyopneumoniae* bacteria, particularly before the inactivation of the bacteria.

At least one of the reactants and/or the vaccine or combined vaccine may contain an adjuvant, preferably a polymeric adjuvant, particularly carbomer. Preferably at least or precisely one of the two reactants, preferably both reactants, contain a quantity of adjuvant of 500 μg to 5 mg, preferably from 750 μg to 2.5 mg, more preferably about 1 mg of adjuvant per dose to be administered. The reactants are preferably prepared or formulated so that 1 ml of the respective reactant corresponds to a dose of 1. The use of an adjuvant, preferably a polymeric adjuvant, such as carbomer, for example, has proved advantageous in relation to the efficiency of immunization or the duration of the effect. However, the use of alternative and/or additional adjuvants is not ruled out.

According to another aspect of the present invention, the first and/or the second and/or the combination of the first and second container B1, B2, B3 with the fluidic connection 2 provided may be configured for use in or with an injection device, and/or used therein. In particular, it is an injection device which can be reused repeatedly, for example an injection gun, a pressure injector and/or a self-filling syringe, of the kind used for vaccinating large herds of animals, for example.

The kit or container system B according to the invention may comprise such an injection device or may be associated with one. In particular, the removal opening E1, E2 or another opening, a flange or other connecting or closing element of at least one of the containers B1, B2 and/or of both containers B1, B2 may be configured so as to allow direct use in or with the injection device. Moreover, the removal device, the opening, the flange or other connecting or closing element may be configured specifically for connection to a particular injection device. This can reduce the probability of incorrect use, particularly the wrong amounts of active substance or methods of administration.

An aspect of the present invention which may also be implemented independently further relates to an injection device with an inserted combination of at least two of the proposed containers B1, B2, B3, which are fluidically connected to one another with the connecting arrangements 3A, 3A', 3B, 3B' according to the present invention. In particular, by means of the fluidic connection 2, a mixture of the substances S1, S2, S3 from the containers B1, B2, B3 is formed and the injection device is set up for injecting the mixture of substances S1, S2, S3.

Further aspects of the present invention will be explained hereinafter with reference to another embodiment, detailing only the differences and special features compared with the embodiments described hereinbefore. The aspects can therefore be combined with the aspects described previously, and vice versa, unless this is specifically ruled out. Moreover, reference will be made to the previous explanations and definitions.

The embodiment described hereinafter with reference to FIG. 22 ff. preferably relates to the variant described above in which the first connecting arrangement 3A' is deformable outside the opening region 4A' and is configured so that the deformation causes the first connecting arrangement 3A' to open in the opening region 4A'. For further details, reference may be made to FIGS. 5 to 13 and the related explanations.

According to an aspect of the present invention which can also be implemented independently, the first connecting arrangement 3A' comprises a preferably rigid, stiff and/or dimensionally stable closure device 23, particularly a closure plate. The closure device 23 is preferably sealingly attached to a holding portion 25 by means of a fragile frangible point 24, particularly a thin point. The opening region 4A' of the first connecting arrangement 3A' may thus be formed with or by the closure device 23 and/or frangible point 24.

The aspects explained previously in connection with the fragility of the opening region 4A', particularly with regard to the material thickness and the like, can preferably be applied to or transferred to the frangible point 24. The difference thus lies particularly in the fact that the opening region 4A' of the first connecting arrangement 3A' additionally comprises the closure device 23 which stabilizes or reinforces the opening region 4A' in a central portion or a portion surrounded by a film-like, brittle, unstable and/or fragile region in the form of the frangible point 24.

The holding portion 25 preferably corresponds to the mouth-shaped portion 5A' of the first connecting arrangement 3A' and/or the mouth-shaped portion 5N comprises the holding portion 25. The related explanations in connection with the mouth-shaped portion 5A' may therefore be applied to the holding portion 25 as well, in an alternative or supplementary capacity. If necessary, the holding portion 25 can therefore also be designated a mouth-shaped portion 5 A' or be wholly or partially formed thereby or vice versa.

Particularly preferably, the holding portion 25 is movable by deformation relative to the closure device 23, so that the first connecting arrangement 3A' can be opened by tearing the frangible point 24. It has advantageously been found that the use of a closure device 23 and the concomitant concentration of the force applied by the deformation on a fragile area (frangible point 24) surrounding the closure device 23 makes it possible to achieve a particularly reliable and simpler opening by means of deformation.

Figure 22:
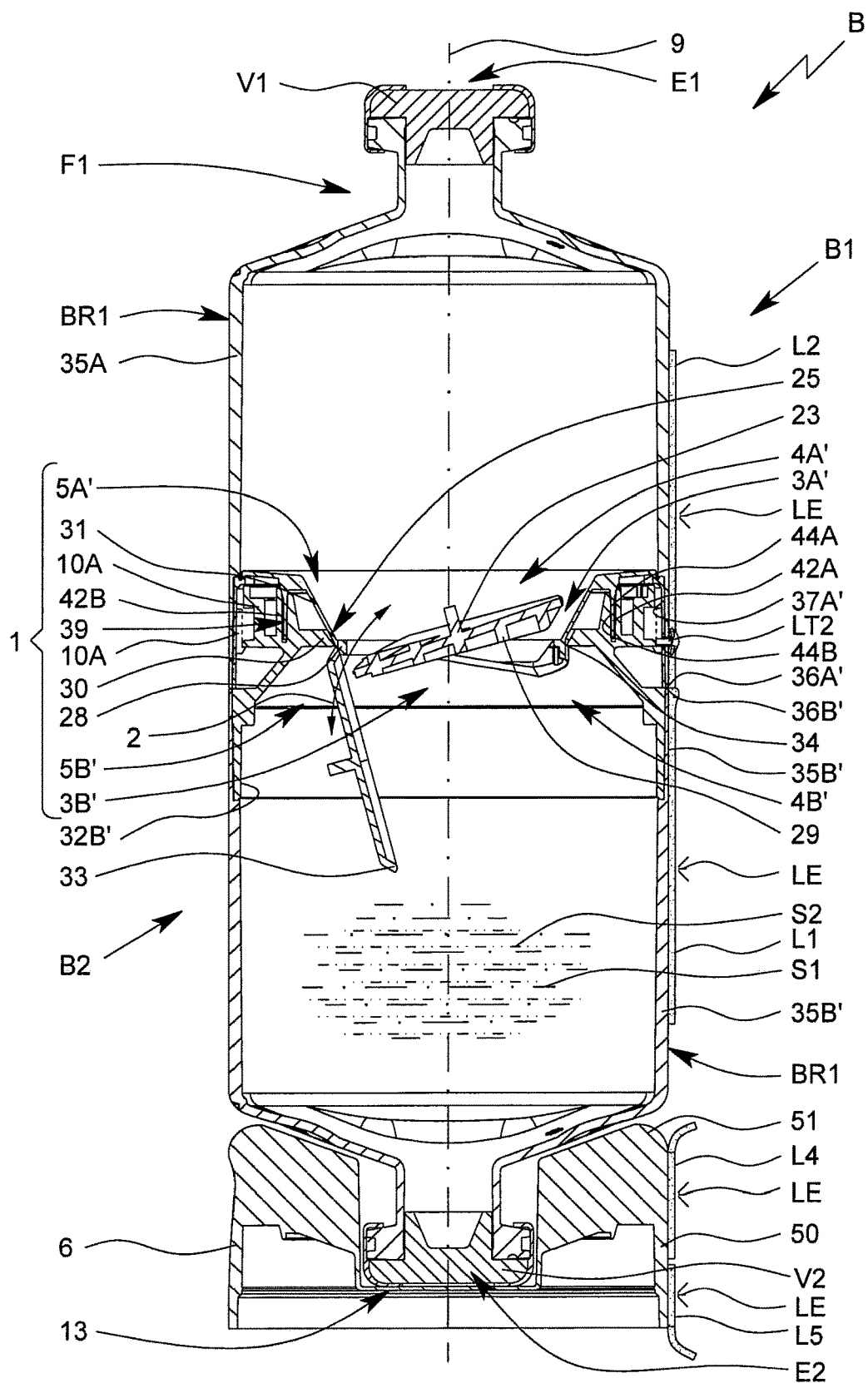
FIG. 22 shows a schematic longitudinal section through a container system according to a further embodiment in the connected state.

FIG. 22 shows an overview of the container system B, in which the containers B1, B2 are fluidically connected to one another by means of the connecting arrangements 3N, 3B'. For this purpose, the first connecting arrangement 3A' or its opening region 4N and the second connecting arrangement 3B' or its opening region 4B' are shown open in each case.

Figure 23:
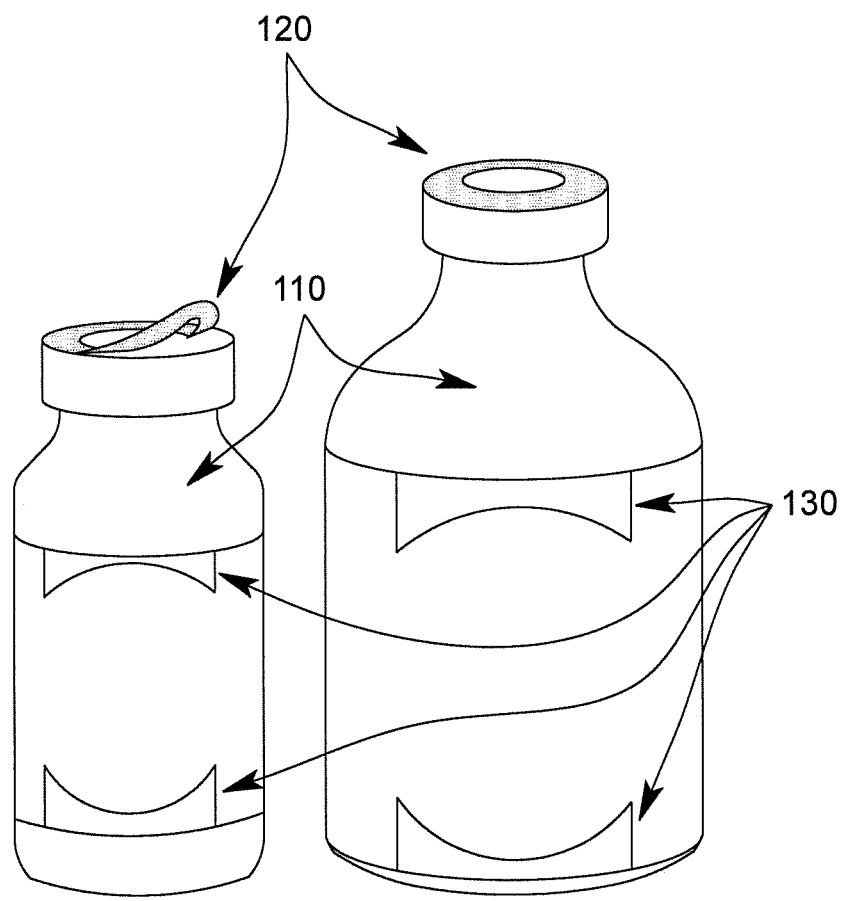
FIG. 23 is one embodiment where the light member is on the serum cap of a package.
Figure 24:
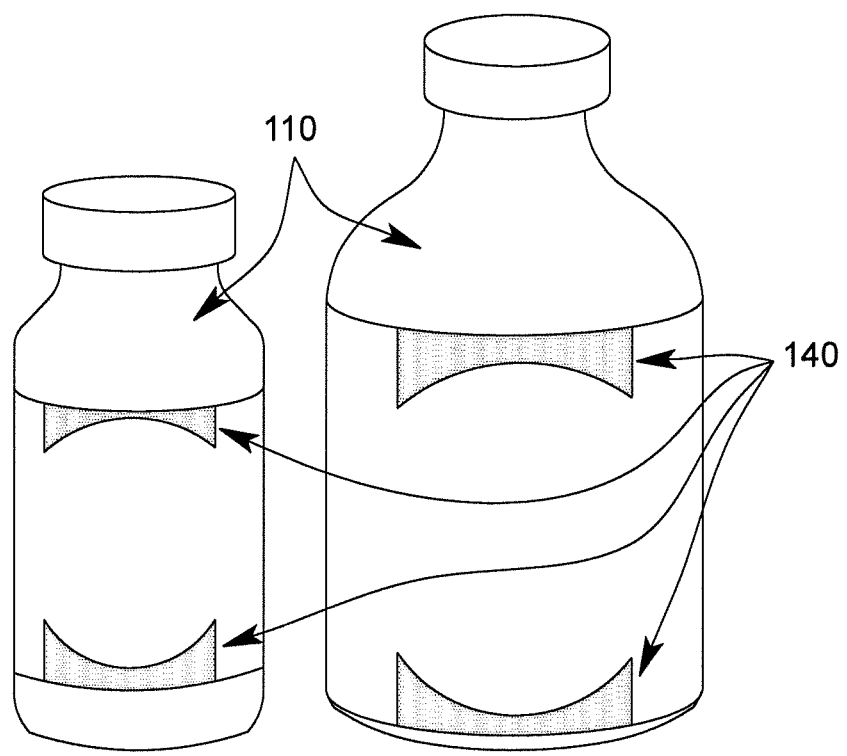
FIG. 24 is one embodiment where the light member is integrated into the label of a package.
Figure 25:
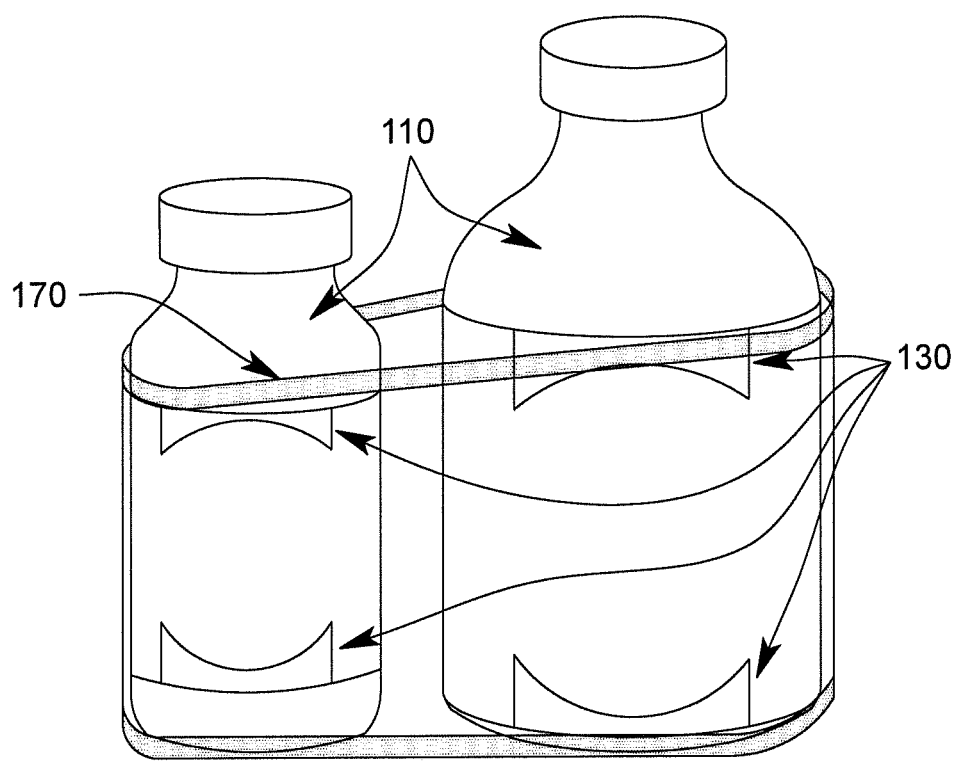
FIG. 25 is one embodiment where the light member is a sleeve that fits around two separate packages that comprise a medicament.
Figure 26:
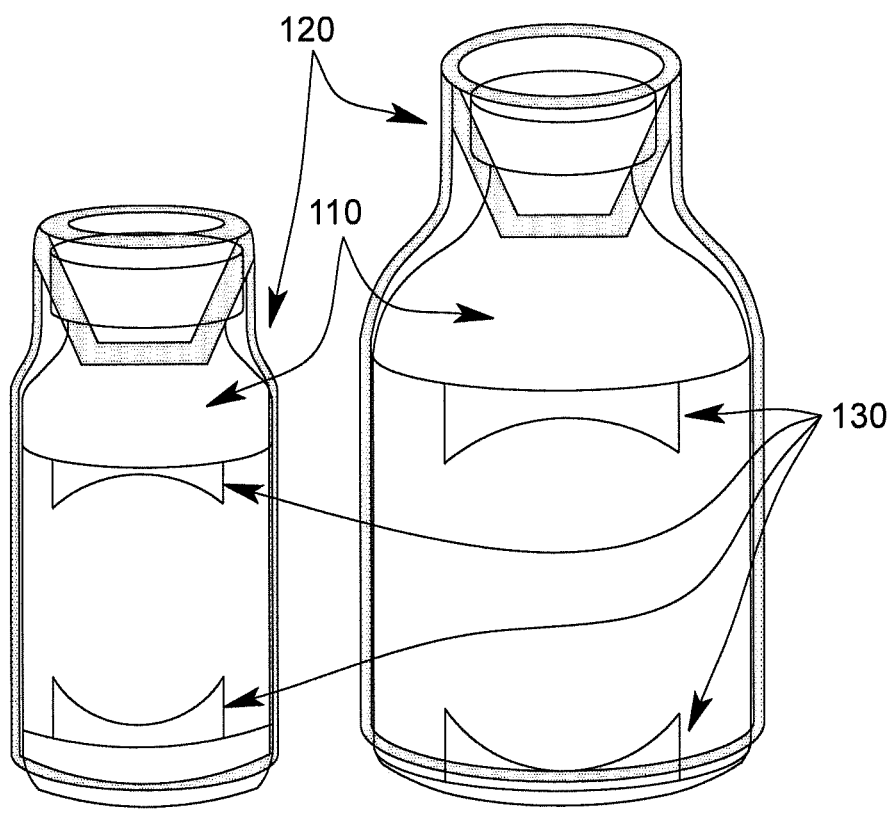
FIG. 26 is one embodiment where the light member is a sleeve that fits over a package.

For the following explanations, reference is additionally made to FIGS. 23 to 26, while FIG. 23 shows a longitudinal section through the first container B1 with the first connecting arrangement 3A' in an initial state with the opening region 4A' closed. FIG. 24 shows a magnified detail of a partial region of the closure device 23 and of the holding portion 25 with the frangible point 24 between them. In the embodiment shown according to FIG. 23 the opening region 4N is covered by a preferably cap-like cover device 26. The cover device 26 has been removed in the embodiment shown in FIG. 25. FIG. 26 shows a perspective representation of the first connecting arrangement 3A' as part of the first container B1 without the cover device 26.

The closure device 23 is preferably configured and/or held by means of the frangible point 24 such that the closure device 23 is inclined as the holding portion 25 is deformed.

Preferably, the frangible point 24 or a surface or plane 27 formed or defined by the frangible point 24 is inclined relative to the central axes or axes of symmetry 9. This enables or facilitates pushing, rotation and/or further inclination of the closure device 23 during the opening process or prevents blockade of the closure device 23 relative to the holding portion 25.

During the opening process the closure device 23 may slide over the holding portion 25 as a result of the deformation of the holding portion 25, particularly while being inclined or tilting.

The holding portion 25 preferably comprises a frame 28 or is of a frame-like construction. The closure device 23 is preferably inclined relative to the frame 28 in the initial state. As a result, the frame 28 and the closure device 23 are each partially offset from one another, with the result that an offset directly adjacent the frangible point 24 may form this or an offset region. The offset is preferably aligned in opposite directions on opposite sides. The advantage of the offset is that during deformation of the holding portion 25 the closure device 23 is able to slide along the frame 28 or tuck in behind it. This makes the opening process easier because blocking of the deformation of the holding portion 25 by the closure device 23 is prevented and as a result the opening of the opening region 4A' is made easier.

Preferably, particularly as a result of the step-like offset of the frame 28 relative to the edge of the closure device 23 adjacent the frangible point 24 and/or as a result of the inclination of the closure device 23 and/or the frangible point 24 relative to the central axis 9, a shearing action of the closure device 23 relative to the frame 28 is made possible, or is achieved during deformation. Such a shearing action advantageously makes it possible to apply a strong mechanical stress to the frangible point 24, in relation to the degree of deformation of the holding portion 25, particularly by producing tensile and/or shear stresses, thus making the severing or tearing of the frangible point 24 easier. Overall, this provides a comfortable and reliable method of opening the opening region 4A' of the first connecting arrangement 3A'.

According to a further aspect of the present invention the closure device 23 is formed in a ramp shape starting from the frangible point 24 provided on the edge thereof. This may be achieved by increasing the material thickness, preferably in relation to a surface or plane 27 defined by or extending through the frangible point 24. Alternatively, or additionally the closure device 23 is formed in a ramp shape starting from the offset region. In this way it is possible to incline the closure device 23 increasingly as the deformation of the holding portion 25 progresses. The ramp-like portion of the closure device 23 can slide along the holding portion 25 and thereby produce an increasing inclination.

The closure device 23 itself preferably comprises a reinforcement 29, in the embodiment shown in the form of ribs or some other added material or added thickness of material that will improve mechanical stability. This reinforcement 29 may be formed at the edge of the closure device 23 or may be configured like a ramp, starting from the frangible point 24 provided at the edge, particularly such that the closure device 23 is increasingly inclined as deformation progresses.

As may be seen for example in the perspective view in FIG. 26, the holding portion 25 is preferably non-round perpendicularly to the central axis or axis of symmetry 9, particularly oval in shape, as explained previously in connection with FIGS. 5 to 13. The same also applies alternatively or additionally to the frangible point 24 and/or an encircling edge of the closure device 23 or such an edge adjoining the frangible point 24 and/or to the frame 28.

The frangible point 24, particularly the thin point, is preferably so fragile that deformation of the holding portion 25 can cause tearing of the frangible point 24 and hence opening of the connecting arrangement 3N.

In the embodiment shown the frangible point 24 is only ten microns thick, preferably less than 300 microns, more preferably less than 200 microns or less than 150 microns. The distance between the holding portion 25 and the closure device 23, which is tightly bridged by means of the frangible point 24, is preferably less than 3 mm, particularly preferably less than 2 or 1 mm, in the embodiment shown less than 0.5 mm. It is also preferable if the distance between the closure device 23 and holding portion 25 or the length of the frangible point 24 does not exceed, or only slightly exceeds, corresponding values in the entire area surrounding the closure device 23. The frangible point 24 thus preferably has an at least substantially constant length and/or material thickness in its extent around the closure device 23. The frangible point 24 thus preferably surrounds the closure device 23 at least substantially completely.

The holding portion 25 is preferably deformable by insertion in a deforming device 30 of at least substantially complementary shape and subsequent rotation of the holding portion 25 relative to the deforming device 30 about the central axis and/or axis of symmetry 9. In particular, the holding portion 25 is radially deformable in relation to and/or in the direction of the central axis and/or axis of symmetry 9.

Figure 27:
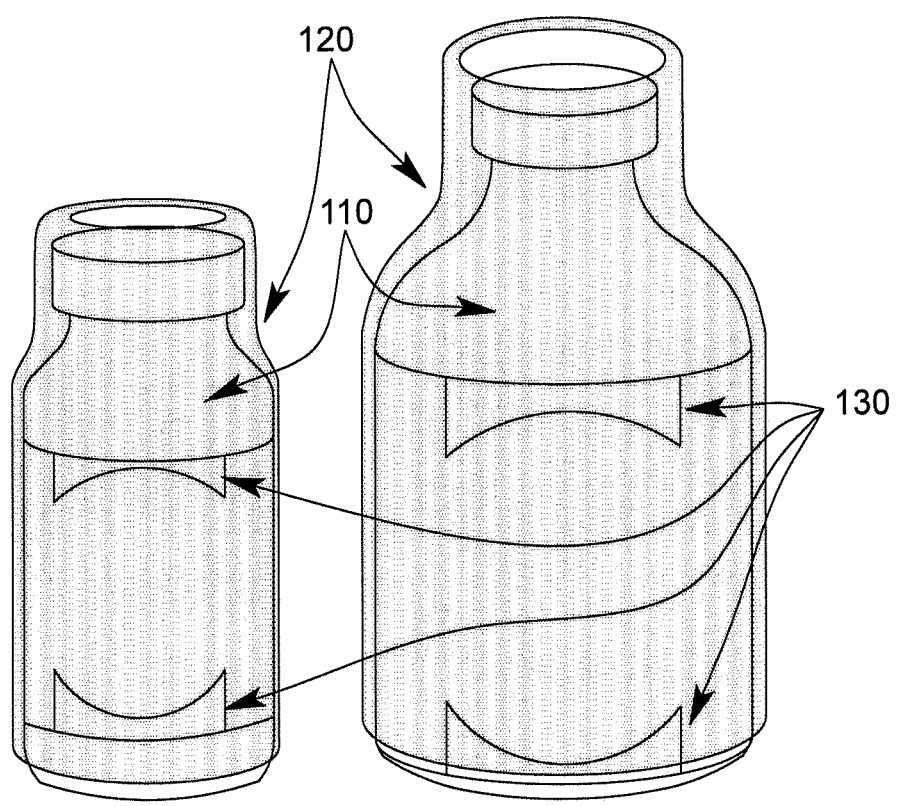
FIG. 27 is one embodiment where the light member is a sleeve that fits over a package.
Figure 28:
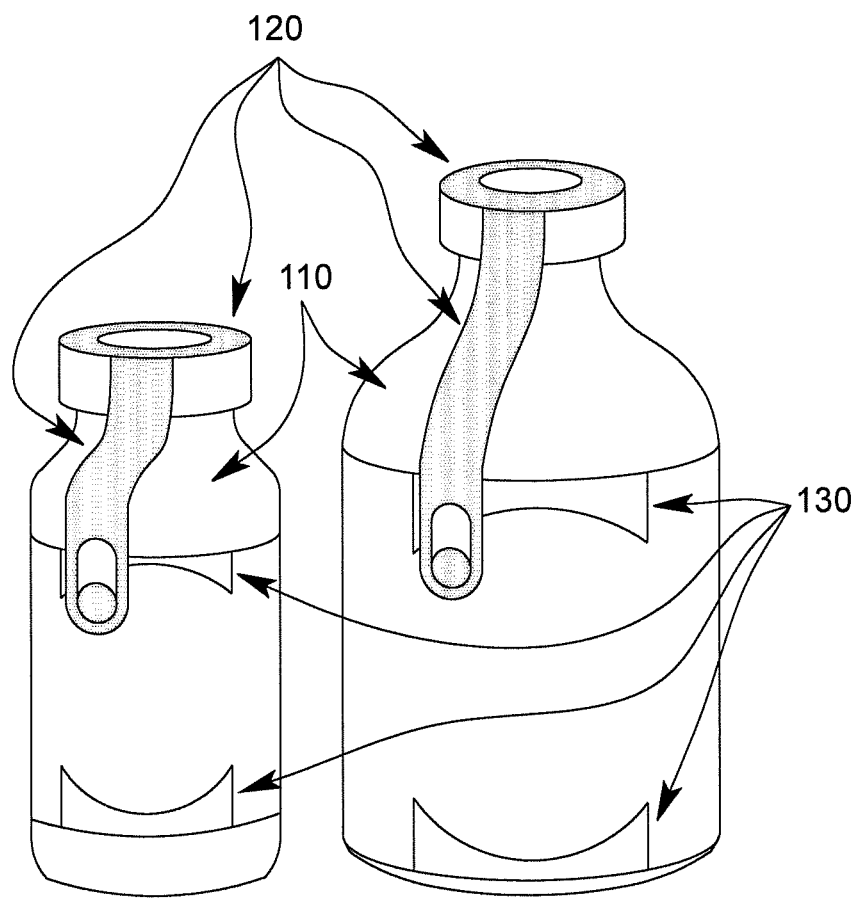
FIG. 28 is one embodiment where the light member is attached to the serum cap of a package.
Figure 29:
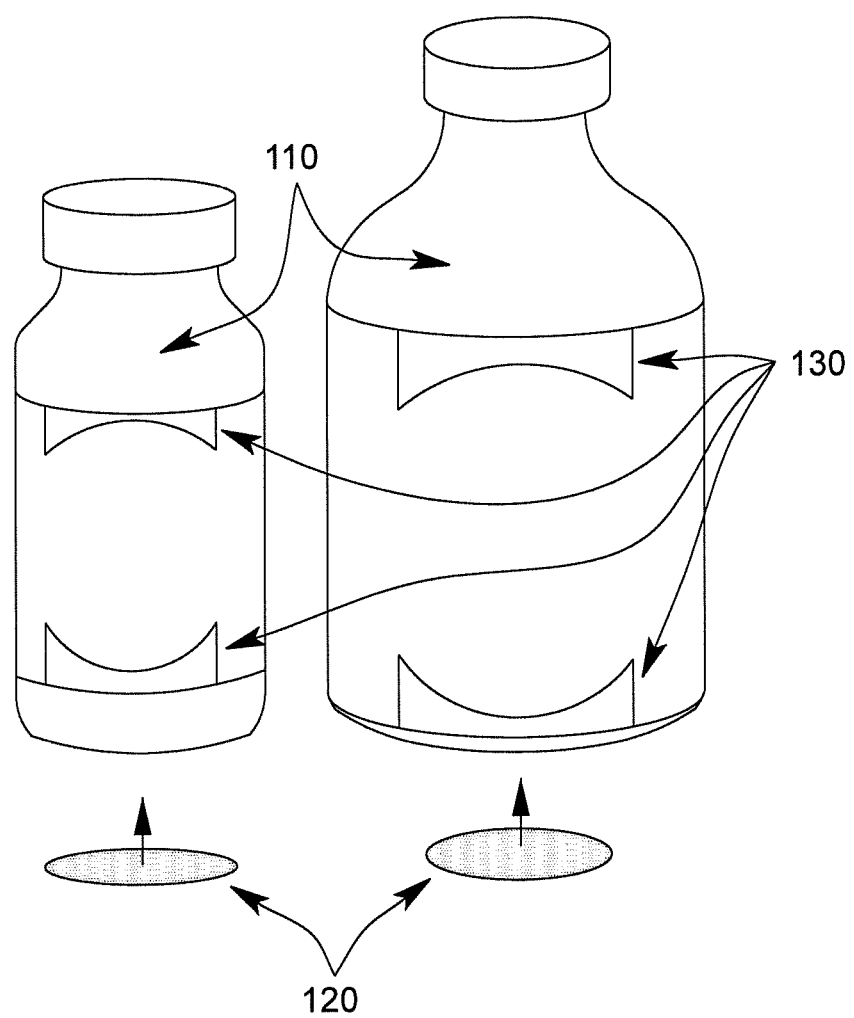
FIG. 29 is one embodiment where the light member is attached to the bottom of a package.
Figure 30:
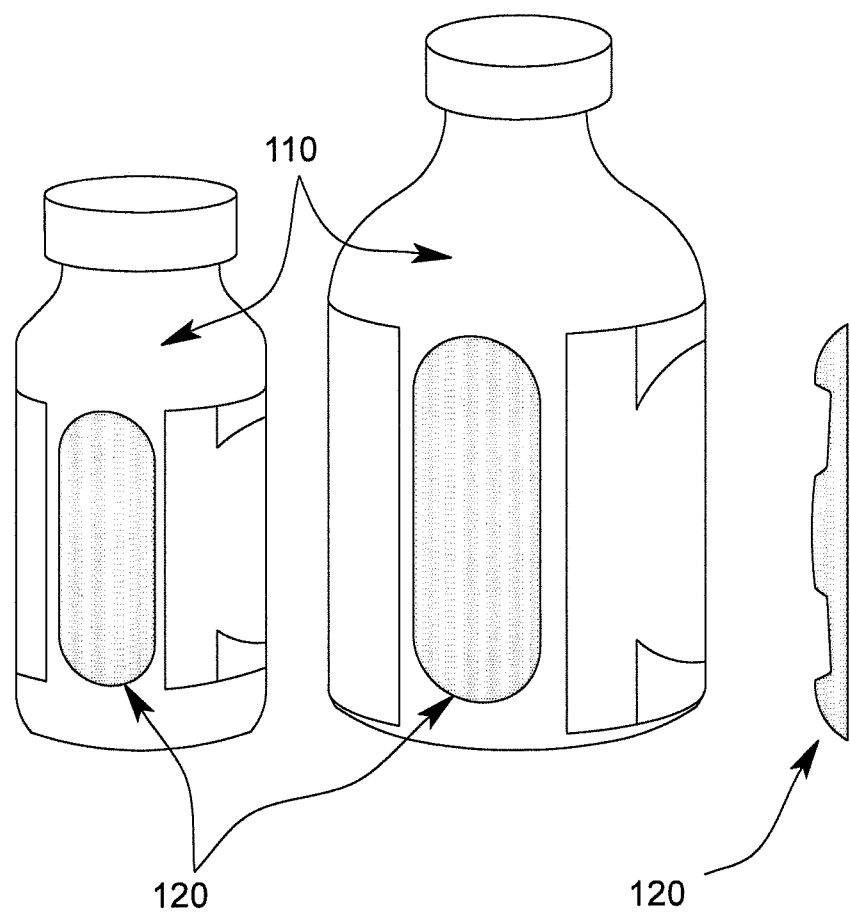
FIG. 30 is one embodiment where the light member is attached to the side of a package.

FIG. 27 shows a section through a second container B2 with the second connecting arrangement 3B' and FIG. 28 shows a magnified detail thereof. FIG. 29 shows the second container B2 with the cover device 6 removed and FIG. 30 shows a perspective view of the second connecting arrangement 3B'.

The deforming device 30 is particularly preferably formed by the second connecting arrangement 3B', particularly its mouth-shaped portion 5B'. For this, reference is made to the corresponding explanation in connection with FIGS. 5 to 13 and to the following explanations of the second connecting arrangement 3B' from the embodiment shown in FIG. 22.

The holding portion 25 of the first connecting arrangement 3N is preferably in the shape of a neck, collar and/or tube with, and in particular by means of, a flexible deformable wall 31. In the embodiment shown in FIG. 22 ff. the wall 31 forms a preferably at least substantially conical shape converging towards the frame 28, which may form the mouth-shaped portion 5A' in the present case. However, other solutions are also theoretically possible here.

It is also preferable that the holding portion 25, particularly the frame 28, has a piercing and/or cutting edge 32 or other severing element 7. The piercing and/or cutting edge 32 is preferably attached to the frame 28, formed by the frame 28, particularly in one piece and/or by molding on. The piercing and/or cutting edge 32 is preferably formed by an at least substantially axially extending strip preferably forming a point.

The piercing and/or cutting edge 32 is preferably configured to open the second connecting arrangement 3B', particularly as a result of the opening region 4B' of the second connecting arrangement 3B' being perforated or pierced by means of the piercing and/or cutting edge 32. Preferably, during an axial movement of the connecting arrangements 3A', 3B' to one another, the opening region 4B of the second connecting arrangement 3B' is first of all pierced by the piercing and/or cutting edge 32 projecting axially outwards relative to the opening region 4A', particularly of the closure device 23, and only afterwards can the opening region 4A' of the first connecting arrangement 3A' be opened by the rotation of the connecting arrangements 3A', 3B' relative to one another in the manner described. By comparison with the embodiment in FIGS. 5 to 13, however, in the present case the holding portion 25 or the mouth-shaped portion 5A' is configured to pierce the opening region 4B' of the second connecting arrangement 3B'. In this respect, reference is made to the previous explanations for supplementary information.

In the present embodiment, by comparison with the previous embodiment, the piercing and/or cutting edge 32 is provided on the mouth-shaped portion 5A', as is also possible in the previous embodiment and advantageous for easier opening of the opening region 4B' of the second connecting arrangement 3B'.

In the present embodiment, the opening region 4B' of the second connecting arrangement 3B' is closed off by an, in particular, at least substantially rigid, dimensionally stable and/or plate-shaped closure device 33, particularly a closure plate or disc, which is preferably sealingly held on the mouth-shaped portion 5B, particularly by means of a frangible point 34. Other constructions are also theoretically possible here, for example as described in connection with FIG. 7. The use of the closure device 33, in a similar manner to the closure of the first connecting arrangement 3A' with the closure device 23, however, makes it easier to open the second connecting arrangement 3B' in the opening region 4B'.

The piercing and/or cutting edge 32 preferably corresponds in its orientation and position to the frangible point 34 of the second connecting arrangement 3B', such that bringing the connecting arrangements 3A', 3B' together leads to the piercing and/or cutting edge 32 being applied to the frangible point 34, as a result of which the frangible point 34 can be severed, starting at the initial point of application of the piercing and/or cutting edge 32. Preferably, the connecting arrangements 3A', 3B' are correspondingly guided to one another.

The frame 28 and/or the piercing and/or cutting edge 32 preferably has a rounded and/or chamfered portion, so that when the piercing and/or cutting edge 32 acts on the frangible point 34 the frangible point 34 is partially spared, so that preferably an intact part of the frangible point 34 still holds the closure device 33 against the mouth-shaped portion 5B' after opening, particularly in the manner of a film hinge. This ensures that the closure device 33 is not detached and prevents blockage of one of the removal openings E1, E2.

In the embodiment shown, in the initial state, the closure device 33 is aligned with the mouth-shaped portion 5B' at least substantially perpendicular to the central axis or axis of symmetry 9. It is certainly possible to have an inclined alignment, as with the closure device 23 of the first connecting arrangement 3A', but this is not absolutely necessary, as the second connecting arrangement 3B' is preferably opened primarily by the piercing and/or cutting edge 32 and not by deformation of the mouth-shaped portion 5B'.

The mouth-shaped portion 5B' is preferably sufficiently stable in its construction and hold so that when the connecting arrangements 3N, 3B' are rotated after being inserted in one another, deformation takes place at least substantially or in any case predominantly in the region of the mouth-shaped portions 5A' or in the holding portion 25. A certain deformation of the mouth-shaped portion 5B' and/or the deforming device 30, of the second connecting arrangement 3B' is possible, however.

According to a further aspect of the present invention the container(s) B1, B2 is or are (each) formed from a container blank BR1, BR2 and the respective connecting arrangement 3A', 3B'. The same may also apply to the previous embodiment.

In the embodiment shown the container blanks BR1, BR2 are upper container or bottle parts, configured for connection to the respective connecting arrangement 3A', 3B' on a side or end remote from or opposite to the removal opening E1, E2. In particular, they are container blanks BR1, BR2 without bases, the resulting open region being closed off during manufacture by means of the respective connecting arrangement 3A', 3B' to form the respective container B1, B2.

Container blanks BR1, BR2 are thus particularly structures with a removal opening E1, E2 and another open point which can be closed off by the respective connecting arrangement 3A', 3B'.

Preferably, the respective connecting arrangement 3A', 3B' is tightly connected to a wall of the container blank BR1, BR2 by material engagement, particularly preferably by welding, adhesive bonding, injection molding or by some other method. The connecting arrangements 3A', 3B may consequently be used in all kinds of containers B1, B2 or may also be used independently of containers B1, B2, for example in order to fluidically connect a container B1, B2 to another structure such as a pipe, a connector or the like. However, the connection of containers B1, B2, B3 to one another is particularly preferred.

Preferably, the (respective) connecting arrangement 3A', 3B' is configured to be connected to the container blank BR1, BR2 so that a container B1, B2 is formed. It is also preferable that the container blank BR1, BR2 should have a wall 35A', 35B' with an open edge 36A', 36B', forming a receptacle for the connecting arrangement 3A', 3B', into which the respective connecting arrangement 3A', 3B' can be inserted and tightly connected to the container blank BR1, BR2.

In another aspect, the present invention relates to a connecting system 1 with the first connecting arrangement 3A' comprising the holding portion 25 and the frangible point 24 and a second connecting arrangement 3B' comprising the deforming device 30 corresponding to the holding portion 25, wherein the connecting arrangements 3A', 3B' can be inserted sealingly into one another and, as the connecting arrangements 3A', 3B' are rotated relative to one another, as a result of the deformation of the holding portion 25 by the deforming device 30, the first connecting arrangement 3A' can be opened in order to produce the fluidic connection 2.

In another aspect which may also be implemented independently, the present invention further relates to one or more containers B1, B2, B3, particularly bottles (each) having a connecting arrangement 3A', 3B' according to the present invention, preferably on a side or end remote from a container opening or removal opening E1, E2, another connecting arrangement 3A', 3B' or a base.

In another aspect which may also be implemented independently, the present invention further relates to a container system B with at least two containers B1, B2, B3, wherein a first container B1 comprises the first connecting arrangement 3N and a second container B2, B3 comprises the second connecting arrangement 3B', which corresponds to the first connecting arrangement 3A'.

The connecting arrangements 3A', 3B' are preferably configured as described hereinbefore. In particular, it is preferable for the first connecting arrangement 3A' to have the piercing and/or cutting edge 32 by means of which the second connecting arrangement 3B' can be opened.

Alternatively, or additionally the second connecting arrangement 3B' comprises the mouth-shaped portion 5B' or the deforming device 30, for opening the first container B1 by means of the first connecting arrangement 3A' by deformation of the holding portion 25 or of the mouth-shaped portion 5A'.

It is also preferable that the connecting arrangements 3A', 3B' should enable the formation of the fluidic connection 2 by mutual opening, the first connecting arrangement 3A' opening the second connecting arrangement 3B' and the second connecting arrangement 3B' opening the first connecting arrangement 3A', thus forming the fluidic connection 2.

In another aspect of the present invention which may also be implemented independently, the connecting arrangements 3N, 3B' are used to prepare a mixture of substances, preferably a medicament, particularly a vaccine or combined vaccine, to produce a fluidic connection 2 and/or to mix starting materials or substances S1, S2 which have been stored separately.

The invention further relates to a method, which may also be implemented independently, for producing one of the connecting arrangements 3N, 3B' or the connecting system 1 and/or a container B1, B2, B3, in which the closure device 23, 33, the frangible point 24, 34 and the holding portion 25 or the mouth-shaped portion 5A', 5B' are injection molded in a common step. This has proved advantageous in terms of reliable production of the frangible point 24, 34.

In the method, it is also preferable if, in a container blank BR1, BR2 having an open end, particularly a bottle blank with a removal opening E1, E2 in addition to the open end, the open end is sealed off by the separately produced connecting arrangement 3A', 3B'.

The connecting arrangement 3A', 3B' preferably comprises a collar-shaped and/or tubular portion 37A', 37B' which delimits the (respective) connecting arrangement 3A', 3B' radially outwards and corresponds to the wall 35N, 35B' of the respective container B1, B2 or container blank BR1, BR2, in order to be inserted therein and connected to the container blank BR1, BR2.

Another aspect of the present invention which may also be implemented independently relates to the sealing concept, based on a combination of the connecting arrangements 3A', 3B' with one another, or of one of the connecting arrangements 3A', 3B' with a preferably cap-like cover device 6, 26.

It is provided that a container B1, B2, B3 is provided with a connecting arrangement 3A', 3B' for producing a fluidic connecting arrangement 2 of the container B1, B2, B3 with another container B1, B2, B3. In an initial state the connecting arrangement 3A', 3B' may be fluidically sealed in an opening region 4N, 4B' and can be opened in order to form the fluidic connection 2. The opening region 4A', 4B' is covered with a cap-like cover device 6, 26 and/or another connecting arrangement 3A', 3B'. This aspect thus relates particularly to an individual container B1, B2, B3 or a connecting arrangement therefor, of the container system B combined with the cap-like cover 6, 26 and/or the (corresponding) connecting arrangement 3A', 3B'.

In another aspect which may also be implemented independently, it is envisaged that the cover device 6, 26 or the other connecting arrangement 3A', 3B' is sealingly held on the proposed container B1, B2, B3, thus forming a sealed chamber 38A, 38B, 38C. Moreover, the proposed container B1, B2, B3 comprises a sealing arrangement 39 surrounding the opening region 4A', 4B' thereof, which seals off a volume 40A, 40B, 40C of the chamber 38A, 38B, 38C in direct contact with the opening region 4N, 4B'. Particularly preferably, the sealing arrangement 39 seals off the inner volume 40A, 49B, 40C from an outer volume 41A, 41B, 41C of the chamber 38A, 38B, 38C. This advantageously covers the opening region 4A', 4B', particularly by means of a double closure. This enhances the barrier preventing the ingress of substances, particularly germs.

It is provided, in particular, that foreign substances can only reach the inner volume 40A, 40B, 40C by passing through the outer volume 41A, 41B, 41C. The sealing arrangement 39 is preferably mechanically decoupled from the environment by an outer seal of the cover device 6, 26, so that any force acting on the cover device 6, 26 may affect the tight seal of the outer volume 41A, 41B, 41C, but the inner volume 40A, 40B, 40C will remain sealed even in such a case, preferably in airtight manner, particularly in germ-proof or bacteria-proof manner. In this way it is possible to guarantee a sterile environment at the opening region 4A', 4B'.

Alternatively, or additionally the sealing arrangement 39 seals off the inner volume 40A, 40B, 40C surrounding the opening region 4A', 4B' by means of the cover device 6, 26 or the other connecting arrangement 3A', 3B' when there is uninterrupted movement of the cover device 6, 26 or the other connecting arrangement 3A', 3B' relative to the connecting arrangement 3A', 3B' of the proposed container B1, B2, B3. In this way, during the process of inserting the connecting arrangements 3A', 3B' into one another and/or during the assembly or removal of the cover device(s) 6, 26, the opening region 4A', 4B' can be protected from the ingress of foreign substances, particularly germs.

It is particularly preferable to combine the two aspects, i.e. to form the chamber 38A, 38B, 38C, which is divided by the sealing arrangement 39 into an inner volume 40A, 40B, 40C and an outer volume 41A, 41B, 41C, the sealing arrangement 39 being configured to prevent the ingress of foreign substances, particularly germs, into the inner volume 40A, 40B, 40C, during, in particular, axial movement of the cover device 6, 26 or other connecting arrangements 3A', 3B'.

The sealing arrangement 39 preferably comprises sealing portions 42A, 42B, 43A, 43B corresponding to one another, a first sealing portion 42A, 42B being associated with the connecting arrangement 3A', 3B' and a second sealing portion 42A, 42B, 43A, 43B being arranged on the cover device 6, 26 and/or on the other connecting arrangement 3A', 3B', particularly being formed in one piece therewith.

The sealing portions 42A, 42B, 43A, 43B preferably comprise sealing surfaces 44A, 44B, 45A, 45B corresponding to one another, which abut closely on one another when the cover device 6, 26 is placed on the connecting arrangement 3A', 3B' or the connecting arrangements 3A', 3B' are fitted into one another.

The sealing surfaces 44A, 44B, 45A, 45B preferably have a similar shape in cross-section (perpendicular to the central axis or axis of symmetry 9) and/or are round and/or rotationally symmetrical to the common axis of symmetry and/or central axis 9.

Preferably, the sealing portions 44A, 44B, 45A, 45B are configured and/or correspond to one another such that it is possible to rotate the cover device 6, 26 and/or the other connecting arrangement 3A', 3B' relative to the container B1, B2, B3.

Preferably, one of the connecting arrangements 3A', 3B' comprises a sealing surface 44A, 44B, which corresponds to both the sealing surface 44A, 44B of the other connecting arrangement 3A', 3B' and to the sealing surface 45A, 45B of the cover device 6, 26 corresponding to the connecting arrangement 3A', 3B'. The sealing arrangement 39 may thus be formed on the basis of a connecting arrangement 3A', 3B' both with the corresponding cover device 6, 26 and with the other connecting arrangement 3A', 3B'. In this way it is possible to obtain a seal over the cover device 6, 26 during transporting and over the other connecting arrangement 3A', 3B' during use, using the same means or re-using the same means.

Another aspect of the present invention, which may also be implemented independently, relates to the connecting system 1 for producing the fluidic connection 2 between the containers B1, B2, B3 and/or a container B3, the connecting system 1 or the container B3 having at least two connecting arrangements 3A', 3B' configured to produce the fluidic connection 2, namely a first connecting arrangement 3A' and a second connecting arrangement 3B', which are each fluidically sealed in an initial state or fluidically close off the container B1, B2, B3 and can be opened in an opening region 4A', 4B' in order to produce the fluidic connection 2.

In another aspect it is provided that the connecting arrangements 3A', 3B' form the sealed chamber 38C and comprise the sealing arrangement 39, while a volume 40C in direct contact with the opening regions 4N, 4B' is sealed off from a volume 41C of the chamber 38C separated from the opening regions 4A', 4B' by means of the sealing arrangement 39.

Alternatively, or additionally the connecting system 1 comprises a sealing arrangement 39 which uninterruptedly seals off a volume 40C in direct contact with the opening regions 4A', 4B' as the connecting arrangements 3A', 3B' are moved relative to one another.

It is also preferable if the connecting arrangement 3N, 3B' comprises at least two positions for connection to one another, which are occupied one after the other in terms of time and location when the connecting arrangements 3A', 3B' are pushed or fitted into one another. In the first connecting position, a non-releasable connection is made between the connecting arrangements 3A', 3B' and the fluidic connection 2 is only produced, or able to be produced, in the second connecting position. For further details, reference may be made to the previous embodiments.

It is particularly preferable that the sealing arrangement 39 seals or closes off the inner volume 40C without interruption in the first connecting position, in the second connecting position and between the first and second connecting positions and/or seals or separates the inner volume 40C from the outer volume 41C without interruption.

For further details of the connecting system 1 in connection with the sealing arrangement 39, reference is made to the previous discussion in particular with regard to the sterile or sterilizable covering in connection with, e.g., FIGS. 16, 17 and 20 and/or in connection with the proposed container B1, B2, B3 with the sealing arrangement 39.

Another aspect of the present invention, which may also be implemented independently, relates to a connecting arrangement 3N, 3B' and/or a container B1, B2, B3 having this connecting arrangement 3A', 3B', wherein the opening region 4A', 4B' of the connecting arrangement 3A', 3B' is fluidically closed in an initial state and can be opened to form the fluidic connection 2. In this aspect, the connecting arrangement 3A', 3B' comprises a cover device 6, 26, which can preferably be latched to the container B1, B2, B3 or the connecting arrangement 3A', 3B' and/or is in the form of a cap and/or is removable, and which covers the opening region 4A', 4B'.

The cover device 6, 26 according to this aspect preferably comprises a support portion 46 which corresponds to the opening region 4A', 4B' and is directly or so closely adjacent to the opening region 4A', 4B' that a force FS acting on the opening region 4A', 4B' in the direction of the support portion 46 is absorbed by the contact of at least part of the opening region 4A', 4B' on the support portion 46 such that opening of the opening region 4A', 4B' is prevented.

In another aspect, which may also be implemented independently, the invention relates to the use of the connecting arrangements and/or containers for mixing viscous liquids, particularly vaccines, preferably with a dynamic viscosity at 23° C. and a shear rate of 1 s$^{-1}$ (particularly measured in the Brookfield viscometer RVT with spindle no. 4) of more than 1.5 or 2 Pa-s (pascal second), preferably more than 4 Pa-s, particularly more than 6 Pa's or 10 Pa-s, and/or less than 100 Pa-s, particularly less than 70 Pa-s, preferably less than 50 Pa-s, and/or in the range from 1 Pa-s to 100 Pa's, particularly from 2 Pa-s to 70 Pa's, preferably from 5 Pa-s to 50 Pa-s. The viscosities specified above within the scope of the present invention may be determined in particular by the method according to EN ISO 2884-1:2006. Viscous liquids in particular benefit from the large hydraulic minimum cross-section of the connection compared with the known solutions.

The aspects of the present invention can be combined with one another. In particular, aspects of the embodiments from FIGS. 1 to 20 may also be used accordingly in the embodiment according to FIGS. 21 to 37 and vice versa.

For example, the aspects relating to the sealing arrangement 39 and/or the support portion 46A, 46B may also be present in the cover device 6 from the embodiments in FIGS. 1 to 20. The cover devices 6, 25 may make it possible to obtain an, in particular, repeated or multi-stage sterile and/or sterilizable closure, while the aspects explained in connection with FIG. 17 can be combined with the aspects concerning the sealing arrangement 39, which were described in connection with FIGS. 22 to 34. Alternatively, or additionally, the aspects relating to the deformation-based opening as explained in connection with FIGS. 6 to 15 can be combined with aspects relating to the closure device 33 or vice versa. These examples make it clear that there are numerous preferred combinations of aspects which may form the subject of the present invention even if the combination is not expressly described.

In one aspect, which can be realized independently as well, the container system B having at least two containers B1, B2, B3 is provided, wherein the container system B or at least one of said containers B1, B2, B3 comprises a light member L1 to L6 which is configured to provide information through the emission of light LE.

In the examples shown, emitted light LE is indicated next to the light members L1 to L6 when the light members L1 to L6 emit light or provide information through the emission of light.

The container system B preferably is configured to provide or trigger the light member L1 to L6 to provide information through the emission of light LE when a step which is directly related to preparing a mixture of contents, in particular substances S1, S2, of the containers B1, B2, B3 is conducted.

As depicted in FIG. 1, a first container B1 can comprise a light member L1 which has already been triggered as a mixture of contents or substances S1, S2 has already been prepared using the container system B. In the example shown, the light member L1 radiates emitted light LE.

Alternatively, or additionally, as shown in FIG. 1 as well, the second container B2 can comprise a light member L2, which, in the example shown, has already been triggered and radiates light LE as well.

One or more of the light elements L1 to L6 can be triggered by means of deformation or depression of the light element L1 to L6 or of parts thereof.

FIG. 2 shows the containers B1, B2 at the beginning of the process for preparing the fluidic connection 2. The light members L1, L2 have not been triggered yet in the example shown.

The light member L1 of the first container B1 comprises a first chemical component LC1 and second chemical component LC2 which are separated from one another by a separator LS.

A section of the light member L1 is arranged such that it is (automatically) depressed when the fluidic connection 2 is prepared. Depressing said section of the light member L1 triggers the light member L1.

The first and second chemical components LC1, LC2 preferably are mixed or come into contact generally by triggering a light member L1 to L5, in the present embodiment by depression of the section of the light member L1. The depression can rupture of the separator LS which in an initial state, as shown in FIG. 2, separates the first and second chemical components LC1, LC2. In FIG. 4, the light member L1 has been triggered by depression of the section of the light member L1.

It is not necessary that said section of the light member L1 is able to provide the information through the emission of light LE but it may be sufficient for this section to trigger the light member L1.

In the example shown, said section comprises or forms a cavity like a pocket containing the first chemical component LC1. Said cavity is separated from an area of the light member L1 comprising or containing the second chemical component LC2 by separator LS. The light member L1 is configured such that, when this cavity is depressed, the separator LS opens or ruptures, thus causing the first chemical component LC1 to come into contact with the second chemical component LC2. Caused by the first chemical component LC1 coming into contact with the second chemical component LC2 the light element L1 can be triggered and/or emit light LE.

Preferably, said section is arranged at a face end of the first container B1, such that the section comes into contact and is (automatically) depressed by the second container B2 during preparation of the fluidic connection 2. In particular, the section of the light member L1 is configured and/or arranged to be automatically depressed when the connecting arrangements 3A, 3A', 3B, 3B' are moved or plugged into one another for preparing the fluidic connection 2.

Each of the light members L1 to L5 might comprise one or more chemical components LC1, LC2 that can be triggered to emit light LE, even if not explicitly mentioned or depicted in the following. Generally, triggering preferably means or comprises bringing said chemical components LC1, LC2 into contact or initiating a different measure like providing a crystal nucleus or switching a source causing a chemical component LC1, LC2 or different light source to emit light LE.

The light member L2 of the second container B2 of the bottle system as depicted in FIG. 1 is triggered differently. Here, a trigger element LT2 acts on or deforms the light member L2 when the fluidic connection 2 is prepared.

As shown in FIG. 2, the trigger element LT2 is configured to act on the light member L2 when the connecting arrangements 3A, 3B, 3A', 3B' are moved or plugged into each other. In the example shown, the trigger element LT2 is realized by a pin which is arranged moveable through a wall of the second container B2 or through a collar-like portion 22 of it such that pressure can be transferred by the trigger element LT2 on the lighting member L2.

Preferably, the trigger element LT2 on a side remote from the light member L2 of the wall or collar-like portion 22 of the container B2 protrudes the wall or the collar-like portion 22 such that, during preparation of the fluidic connection 2, in particular when the first connecting arrangement 3A, 3A' is inserted into the second connecting arrangement 3B, 3B', the trigger element LT2 is pressed towards the light member L2, whereby the light member L2 is triggered. In particular, the light member L2 is triggered by deformation such that separator is ruptured or causing a different trigger means to start a reaction that causes the lighting member L2 to emit light LE.

In the example shown, the light member L2 comprises a trigger member LA2 which is configured for starting and/or changing the emission of light by means of the light member L2 if the trigger member LA2 is pressed. The trigger member LA2 can be broken by means of the trigger element LT2 when it is moved towards the light member L2. This preferably causes chemical components LC1, LC2 (not shown) to come into contact or to start a chemical process for emitting light LE by the light member L2.

In the example shown, the trigger member LA2 preferably is frangible or brittle. Further, in the example shown the trigger member LA2 is flat, a plate or disk-like. The trigger member can be configured to trigger the light member L2 or start it to provide information by the emission of light LE when deformed, ruptured and/or destroyed. However, the trigger member LA2 alternative or additionally can contain and separate a chemical component from a different chemical component of light member L2 such that destroying said trigger member LA2 causes the light member L2 to provide the information and/or to emit light.

The light member L2 can alternatively or additionally be triggered by means of a different trigger element LT2' which can be driven by means of or caused by a rotational movement of the connecting arrangements 3A, 3B, 3N, 3B' relative to one another and/or by deformation of mouth-shaped portions 5A, 5N, 5B, 5B' of the connecting arrangements 3A, 3B, 3A', 3B'.

As depicted in FIGS. 9 and 11 to 13, the trigger element LT2' is or comes into contact with the mouth-shaped portion 5B' which is deformed when the fluidic connections 2 is prepared, such that the trigger element LT2' is moved towards and, thus, triggers the light member L2.

A trigger element LA2' which is configured to trigger the light element L2 in this embodiment can comprise a cavity which can automatically open when the trigger element LT2' presses thereon. This can cause chemical components to mix which allows providing the information by emission of light LE.

However, there might be different options to drive a trigger element LT2, LT2' such that the trigger element LT2, LT2' acts on to the light member L2 in a manner that the light member L2 is triggered.

In FIG. 14, a different kind of container B3 of the container system B is depicted, wherein a light member L3 can be triggered as previously discussed referring to the first container B1 or, as depicted in FIG. 14, as discussed referring to the second container B2.

In FIG. 16, further different options to realize light members L4, L5 are shown. In FIG. 16, the containers B1, B2 of the container system B are arranged in a transport configuration or connected for transport purposes, in particular forming a kit.

The first and second containers B1, B2 preferably are assigned to one another or connected to one another in the initial state before starting any steps for preparing the mixture, said initial state also referred to as transport configuration.

In the example shown, the second container B2 at least partially is arranged and/or held inside the first container B1 or a cover device 6 thereof, the cover device 6 preferably having a receptacle for uptaking the bottleneck of the second container B2.

A light member L4 is arranged and configured in such a way that separating the containers B1, B2 from one another triggers the light member L4. In particular, the light member L4 is arranged on one of the containers B1, B2 and connected to the other one of the containers B1, B2 in a manner that separating the containers B1, B2 from one another causes deformation, in particular stretching, of the light member L4, by means of which the light member L4 is triggered. This can be achieved by direct connection, using a pull-tab or the like. However, different triggering mechanisms might be used alternatively to, preferably automatically, trigger the light member L4 when the containers B1, B2 are separated from one another.

One or more of the containers B1, B2, B3, in the example depicted in FIG. 16 the first container B1, can comprise a cover device 6 for covering a (the first) connecting arrangement 3A, 3N or opening region 4A, 4A', where the cover device 6 needs to be removed in order to facilitate preparation of the fluidic connection 2.

A light member L5 can be arranged on the first container B1 and/or on the cover device 6 and can be configured such that removing the cover device 6 from the first container B1 or the part of the first container B1 comprising the component or substance S1 triggers the light member L5. In the example shown, the light member L5 is arranged on the cover device 6, but it can alternatively or additionally be arranged on the wall of the first container B1.

The light member L5 is arranged such that separating the container B1 from its cover device 6 (automatically) causes the light member L5 to be triggered. In particular, the light member L5 is automatically bended, stretched, deformed or acted on in a different way such that the light member L5 is triggered.

The light members L1 to L5 in the present embodiments preferably are labels or label-like, although differently formed light members are possible alternatively or additionally.

In a further embodiment, a light member L6 as depicted in FIG. 16 might form part of the container B1 to B3 or cover device 6 and might have a housing which can be stable in form or rigid. Said light member L6 might be triggered by means of a trigger element, by deformation, tension or the like. In the embodiment shown in FIG. 16, the light member 16 detects a step like disassembly of the cover device 6 by means of a device which is configured to change an electrical contact like a switch or sensor. Light member L6 can alternatively or additionally be arranged at a different position or part of the container system B.

The light members L1 to L6 do not necessarily produce light by means of chemical effects although this is preferred. One alternative is providing, using and/or controlling an electrical light source like an LED.

The container system B has been described with multiple light member L1 to L6 that can be (automatically) triggered by means of different triggering mechanisms. However, only one, two, three or four light members L1 to L6 might be provided. Further, light members L1 to L6 can be arranged at different positions and triggered in different manner, i.e., the triggering mechanisms can be exchanged or replaced.

In particular, light members as described later referring to FIG. 23 ff. can be triggered like light members L1 to L6 or differently, preferably automatically by means of a step being in direct relation to or has to be performed for preparation of the fluidic connection 2.

In one further embodiment, one or more of the light member(s) L1 to L6 can be configured to be triggered when being stretched, bended or deformed. In particular, light member L1 to L6 can be connected to the container B1, B2, B3 and configured in such a way that this stretching during preparation of the fluidic connection 2 of the container B1 to B3 causes the light member L1 to L6 to be triggered.

Such one or more of the light member(s) L1 to L6 extends through a region of a container B1, B2, B3 of the container system B which is stretched, bended or deformed during preparation of the fluidic connection 2. For example, the light member L2 as shown in FIG. 2 or 5 can be stretched by means of obstacles like security elements 10B being displaced during preparation of the fluidic connection 2.

In FIG. 5 there is at least one securing device 10B or a different part or obstacle of the second container B2 which has a structure, like a slope, which is (automatically) moved or bended towards the light member L2 in order to enable triggering the light member L2 by pressure or deformation when the fluidic connection 2 is prepared, which can trigger the light member L2 alternatively or additionally to triggering by means of trigger element LT1 and/or trigger member L2.

Generally, steps being in direct relation to preparation of the fluidic connection 2 which can cause (automatic) triggering one or more light elements L1 to L6 can be or cover, but are not necessarily limited to one or more of:
  depackaging the container system B or containers B1, B2, separating the containers B1, B2 from one another,
  removing one or more cover devices 6 from containers B1, B2 or connecting arrangements 3A, 3B, 3A', 3B',
  moving the containers B1, B2 or connecting arrangements 3A, 3B, 3N, 3B' towards or into each other,
  inserting one of the containers B1 to B3 or connecting arrangements 3A, 3B, 3A', 3B' into another one of the containers B1, B2, B3 or connecting arrangements 3A, 3B, 3A', 3B',
  turning containers B1, B2 or connecting arrangements 3A, 3B, 3A', 3B' relative to each other, and
  piercing and/or rupturing and/or deforming one or more opening regions 4A, 4A', 4B, 4B'.

Triggering one or more light members L1 to L6 preferably causes the triggered light member L1 to L6 to emit light LE, preferably to start emission of light LE which can indicate or provide the information that a mixture is viable or deemed to be viable.

Alternatively or additionally, triggering the light member L1 to L6 not immediately causes starting emission of light LE but may cause a delayed start of light emission, i.e., light emission in order to provide information after a period of time which might be related or correspond to a period of time a mixture formed from the contents or substances S1, S2 contained in the containers B1 to B3 is or is deemed to be viable.

Alternatively, or additionally, the light member(s) L1 to L6 can be configured to stop emitting or change properties of emitted light LE after the period of time has expired that corresponds to a time span or the period of time the mixture of contents or substances S1, S2 remains or is deemed viable. This can provide information that the mixture shall not be used anymore.

For example, the chemical components LC1, LC2 which are used to produce the light LE can be configured or a structure or properties of the light member(s) L1 to L6 can be arranged such that emission of light LE stops after the period of time.

In one example, the light member L1 to L6 emits light over at least essentially the whole light member L1 to L6. Alternatively or additionally, the light member L1 to L6 can be configured or structured in a way that only a section or part of the light member L1 to L6 emits light LE at each time, wherein the section may be continuously changed or moved such that light emitting sections virtually move over the light member L1 to L6 over the period of time.

Consequently, the light member L1 to L6 preferably realizes a counter, timer or clock allowing (automatic) indication of the period of time over which the mixture remains or is deemed to remain viable. However, there might be different approaches to provide such information regarding the period of time or its expiry which preferably is triggered by a step which directly relates to the process of preparation of the fluidic connection 2.

Alternatively, or additionally to starting or stopping emission of light, one or more light members L1 to L6 might be configured to change properties of the emitted light LE with or after expiry of the period of time. In particular, the color of the emitted light LE might be changed and/or, as already indicated, the position at which the light member L1 to L6 emits light may change.

In a combination of these aspects, differently colored light can be emitted by one or more of the light members L1 to L6 generated by a varying or moving section of the light member L1 to L6 over the period of time.

Emission of light LE in the sense of the present invention particularly preferably relates to or is active radiation of electromagnetic waves having one or more wave lengths in the range being visible for human eyes, in particular by means of chemoluminescence. Alternatively, or additionally, light LE can be emitted by means of fluorescence or phosphorescence, where energy is absorbed and re-transmitted in a different wavelength and/or at a different or spread over time. Although active emission of light is preferred, alternatively or additionally passive emission of light is possible as well, wherein the light member L1 to L6 for example can change reflection or absorption properties with respect to light such that the information, in particularly regarding the period of time, is provided optically.

In the following, the invention is further described generally related to packages, which, however, can comprise or be realized by one or more containers B1, B2, B3, wherein the containers B1, B2, B3 can comprise connecting arrangements 3A, 3A', 3B, 3B' even if neither depicted nor explicitly mentioned.

In the following, further examples, in particular the position, shape and/or properties of light members are discussed in further detail referring to FIG. 23 ff. Even if triggering light members might not be described or might be described differently with respect to those embodiments, alternatively or additionally such light members described in the following can be triggered as previously described, in particular automatically by means of a step which is or the connecting system 1 demands for to be conducted in order to prepare the fluidic connection 2 and/or to mix up the contents/substances S1, S2 contained by the containers B1 to B3. For example, light members being arranged at or surrounding a removal opening like a vial can be triggered automatically when the removal opening like a vial is removed from an uptake 13.

The packages and methods disclosed herein overcome the limitations present in presently available packages including medicaments and meet one or both of the unmet needs disclosed herein; that is, the packages and methods disclosed herein address either the need to provide the end-user with information regarding the viability of the medicament being administered to the animal or to assist the farmer with the visibility of a package under low light conditions. In some embodiments, the packages and methods disclosed herein overcome both unmet needs simultaneously.

A large variety of packaging types are known for use in medicinal applications and products. Examples of known packages include, but are not limited to, bottles, boxes, vacuum packs, and bags. The embodiments disclosed herein are suitable when applied to any type of package. Desirably, the package is for medicinal products or a medicament, and is a bottle. In another embodiment, the package is desirably a box in which the medicament is stored, shipped, or otherwise packaged prior to delivery to the end-user. In one non-limiting example, the package is a box that contains multiple bottles of a medicament that are delivered to a farmer or veterinarian. The multiple bottles of medicament inside the box may or may not have an individual light member for each individual bottle.

Some packaging for use with a medicament that requires regulatory approval will also be subject to regulatory requirements as determined under appropriate national authority, for example, by the United States Food and Drug Association. The light member disclosed herein, when integrated into to the label or exterior adornment of a package, will meet any required regulatory requirements if necessary. In some embodiments, there are no regulatory requirements that would apply to the light member. In other embodiments, there are regulatory requirements that apply to the light member.

In some embodiments, the package comprises a medicament, and the package comprises a light member that is configured to provide information to the end-user. The light member may be attached to the package when activated to produce light; or the light member may be activated to produce light and then subsequently attached to the package. In other embodiments, the light member may be activated to produce light and simply placed next to the package. The end-user may be a farmer, farm worker, veterinarian, veterinarian technician, or any individual who is providing medical treatment for an animal. In some desirable embodiments, the package is a bottle comprising an animal vaccine. In some embodiments, the bottle comprising the animal vaccine is suitably shaped and size for use with an animal vaccination gun. In some other embodiments, the information provided to the end-user is simply the location of the package or a specific part of the package under low light conditions. In some aspects, the information provided to the end-user is about the viability of the medicament inside the package. In some other aspects, the information provided is both regarding the viability of the medicament inside the package and the location of the package or specific part of the package under low light conditions.

In yet another aspect, the light member is part of a kit. The kit comprises at least one package comprising a medicament and at least one light member. The medicament and the light member can be any embodiment disclosed elsewhere herein. As one non-limiting example, the kit comprises two different vaccines for two different medical conditions. Included in said kit are two different colored light members.

Figure 33:
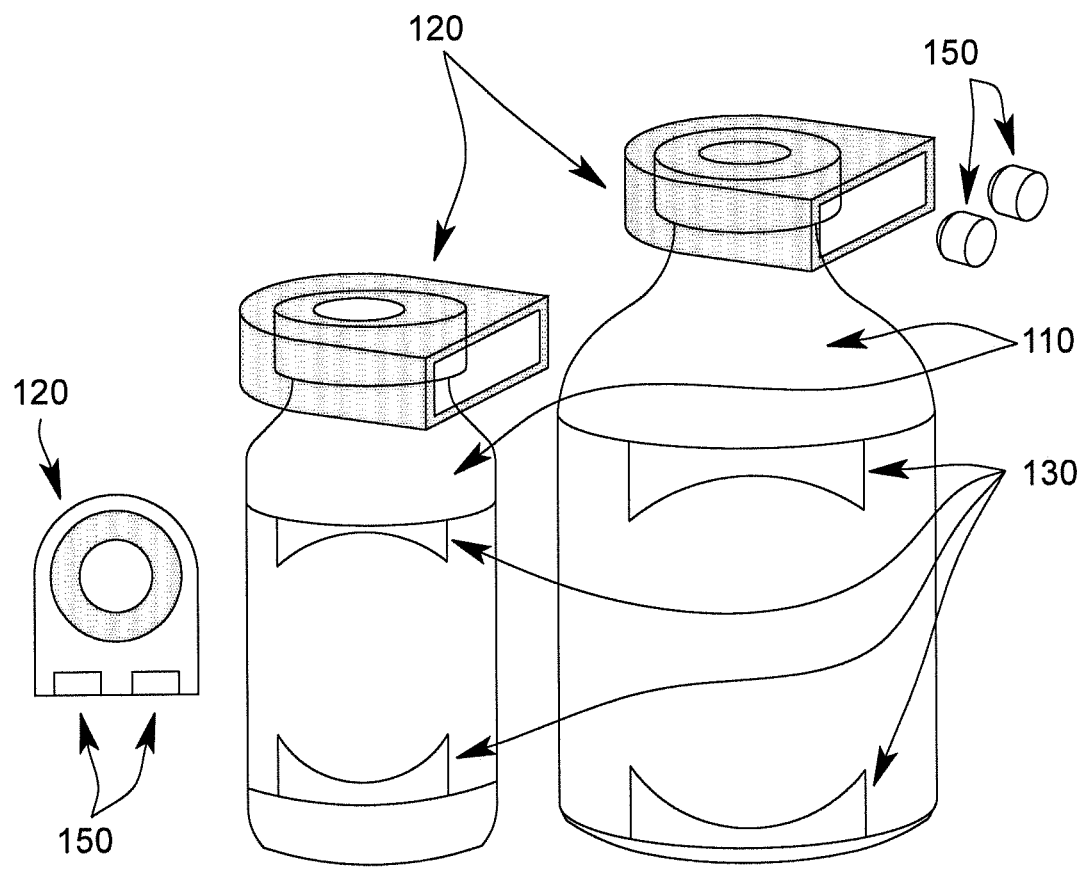
FIG. 33 is one embodiment where the light member is a cap that fits over the serum cap of a package and includes an LED light source.

One white LED light member as described in FIG. 33 is included to enhance the visibility of the septa on the serum cap, and each vaccine comprises a light member as described in FIG. 30 already attached to the bottle wherein one vaccine has a green light member and the other vaccine has a yellow light member. However, different colors or differently operated light members can be used alternatively or additionally.

Informational material in the form of written instructions may be included in the kit. Said written instructions may include any relevant information in relation to the kit, including, but not limited to, the manner in which to actuate the light members and instructions relating the length of time that the light member remains visible to the viability of the medicament.

As another non-limiting example, the kit comprises a box with a fluorescent label; inside the box there is at least one bottle comprising a vaccine and at least one light member as illustrated in FIG. 29. The light member has a "peel and stick" adhesive that can be used to attach the light member to the bottom of the vaccine bottle. The light member is activated by pinching it forcefully enough to rupture the internal separator for the chemicals inside once the vaccine is either reconstituted or removed from refrigerated storage. Activation may be either prior to attaching to the bottle or any time thereafter as desired by the end-user.

The medicament in the package is not limited and may be any medicinal product. In some embodiments, the medical product has a limited viability when it is either reconstituted or removed from refrigerated storage. In some other embodiments, the medicament is a veterinary product selected from the group consisting of immunogenic compositions, antibiotics, vaccines, nutritional supplements, growth supplements, antifungal medication, anti-parasitic medication, hormones and combinations thereof. In many embodiments, the medicament is a vaccine such as, for example a vaccine for BVD including Bovela®.

In many embodiments described herein, the signal to the end-user is in the form of emitted light. The light source may be fluorescence, chemiluminescence or a light emitting diode, and may be active or passive in nature. The light source is a light member that emits light upon actuation and is either integrated into external adornment of the package or is able to be attached to the exterior of the package by any suitable method, as noted above.

In some embodiments, the fluorescence is passive illumination. In such an aspect, the light member may be either combined with or separate from the label on the package. The light member may be fully or partially incorporated into the label of the package. In another aspect, the light member may be a separate structure that is attached to the package by the end-user at a designated time in a designated manner. In another aspect, the light member may be attached to the package prior to delivery to the end-user. For a passively light member, the fluorescence is activated by placing the light member under a light source for a predetermined period of time. Such light source may be artificial (e.g., a light bulb) or natural (e.g., the sun).

In some embodiments, the fluorescence is active illumination. In such an aspect, the light member may be either combined with or separate from the label on the package. The light member may be fully incorporated into the label of the package. In another aspect, the light member may be a separate structure that is attached to the package by the end-user as a designated time in a designated manner. In another aspect, the light member may be attached to the package prior to delivery to the end-user. For an actively light member, in some aspects, the fluorescence is activated by the mixing of two or more precursor chemicals. Such arrangements are known in the art. For example, a separator inside the light member can keep the precursor chemicals separate. Upon rupture of the separator, the precursor chemicals mix resulting in a fluorescent reaction. Rupture can be caused by exerting force on the separator in the form of shaking, compression or bending. As a non-limiting example, the light member can be compressed by the end user thereby causing the rupture of the separator which permits mixing of the precursor chemicals. In another aspect, when the light member comprises an LED, actuation is done using an actuation switch on the LED that comprises at least two settings—on and off. As non-limiting examples, actuation of the LED can be by a mechanical action such as twisting, turning, or compression of the actuation switch.

In some embodiments, the light member is not affixed to the package prior to delivery to the end user. Either subsequent to, coincident with or shortly after actuation of the light member, the light member can be attached to the package. In another aspect, the light member is activated, but the light member is not attached to the package. Attachment may be permanent or temporary. If the attachment is temporary, removal of the light member can be done such that the light member is preserved for use on another package. Methods of attachment are not limited and may include an adhesive (e.g., glue), tape, and the like. In some embodiments, attachment of the light member involves inserting the package into a sleeve or band that comprises the light member. Methods of attachment are known in the art, and any method of attachment that does not interfere with the light emitted by the light member or the contents of the package is acceptable. In some embodiments, the attachment is via a "peel and stick" method, whereby a protective cover is removed from an adhesive on one part of the light member, and the exposed adhesive is pressed against the package in any suitable location. In another non-limiting example, the light member has a dry glue on part of one surface that is moistened to render the glue sticky. As another example, the light member (described in FIGS. 6 and 27 below) in the form of a sleeve can be slid on and off of the package and readily placed on another package. In another embodiment, the light member is in the form of a fluorescent paint that is coated onto the package prior to delivery or sale to the end-user. The fluorescent paint would not affect the contents of the package or pose health and safety risks to the animals or the end-user.

Fluorescence and chemiluminescence are known to be transient processes that last for a limited period of time. They have a finite lifetime that can be controlled based on careful selection of the materials and chemicals involved. In some aspects, the time period that the fluorescence lasts is from 1 to 100 hours and all integral values in between, specifically including 1 hour, 2 hours, 3 hours, 4 hours, 5 hours, 6 hours, 7 hours, 8 hours, 9 hours, and 10 hours. In some embodiments the fluorescence is tailored to last for a predetermined period of time that is matched to some property of the medicament inside the package. In one desirable embodiment, the property of the medicament is the length of time it remains viable after reconstitution or removal from refrigerated storage. In some embodiments, the light members emits light for 1 hour, 2 hours, 3 hours, 4 hours, 5 hours, 6 hours, 7 hours, 8 hours, 9 hours, 10 hours, 11 hour, 12 hours, 13 hours, 14 hours, 15 hours, 16 hours, 17 hours, 18 hours, 19 hours, 20 hours, 25 hours, 30 hours, 35 hours, 40 hours, 45 hours, 50 hours, 55 hours, 60 hours, 65 hours, 70 hours, 80 hours, 90 hours, or 100 hours after actuation.

It is known that some medicaments have limited viability after reconstitution or removal from refrigerated storage. In some embodiments, the length of time that the light member emits light is matched as closely as possible to the time period that the medicament remains viable. As a non-limiting example, some animal vaccines are viable for 8 hours after reconstitution or removal from refrigerated storage. As such, the time period that the light member continues to emit light would be 8 hours. When light is no longer emitted from the light member, the end-user would know that the medicament was no longer viable and should not be used. It is understood that the time period that a medicament remains viable after reconstitution or removal from refrigerated storage may vary depending on the environmental conditions the medicament is kept and/or the manner in which it is used. The time period that the light member continues to emit light would be determined based on the instructions included with the medicament.

In some embodiments two or more light members are used simultaneously for one package. Each light member may be the same or different. Each light member may have a different color or time period for which light is visible. For example, two different colors with two different time periods may be used to provide different information to the end-user. The color of the light member is not limited and may be any color visible to the human eye. Examples include, but are not limited to, white, red, orange, yellow, green, blue, indigo and violet. Different shades and intensities are also not limited. They are selected based on the desired characteristics of the light member. Additionally, one or more light member may be used that changes color after a specific time period to provide information to the end user (such as that the medicament is no longer viable, etc.).

In one non-limiting example, a red light member on the serum cap of a bottle (as shown in FIG. 23 discussed below) is used to assist the end-user in properly locating the septa for syringe access to the medicament while a second green light member is attached to the side of the package (as shown in FIG. 30 discussed below) to indicate the viability of the medicament inside the package. In embodiments with more than one light member, each light member may individually be active or passively illuminated, and may individually be integrated into the package or attached to the external adornment of package. Each light member may be the same or different in color. Each light member may use a different source of light.

In another non-limiting example, a light member using an LED light source (as shown in FIG. 33 discussed below) is attached to the serum cap of the package to assist the end-user in locating the septa under low light conditions while an active chemiluminescent light member having a light time period of 8 hours (as shown in either FIG. 29 or 30 discussed below) is activated upon reconstitution of a medicament that is known to have 8 hours of viability after reconstitution. After the 8 hour time period elapsed and the chemiluminescent light member is no longer visible, any remaining medicament would be discarded. The LED light member would be removed, deactivated, and either placed on a new bottle of medicament or saved for future use.

In another non-limiting example, the label of a package for a first medicament comprising a green light member and the label of a different package for a second medicament comprising a red light member are used simultaneously under low or poor lighting conditions. The color difference would allow identification of each medicament where one group of animals is given the first medicament and a second, different group of animals, is given the second medicament. Such color differentiation could be combined with a different color marking directly on the animal, for example, a non-toxic paint or dye, to help determine which animals have been given which medicament.

Also disclosed herein is a method for determining the viability of a medicament in a package. The method comprises actuating the light member as described elsewhere herein when the package comprising the medicament is initially opened or brought into use and observing the loss of fluorescence after a predetermined period of time. The complete loss of fluorescence indicates that the medicament is no longer viable. In some embodiments, the light member is attached to the package prior to actuation. In some embodiments, the light member is activated and then attached to the package by the end-user.

A package comprising a medicament and the light member is considered to be opened or brought into use when the end-user prepares to administer the medicament to an animal or animals. In some embodiments, the package is removed from refrigerated storage and allowed to warm to ambient temperature. Refrigerated storage does not suggest or require any specific temperature, only that the temperature be below standard ambient temperature, usually 25° C., in order to preserve the medicament for an extended period of time prior to use. Some forms of refrigerated storage are below the freezing point of the medicament, including below 0° C. In some embodiments, opening or bringing into use means that a solid is reconstituted with a liquid such that the resulting solution can be administered to an animal via syringe, vaccination gun, or similar method. Other means of opening and bringing into use are known and will be specific to the medicament and the steps necessary before it can be administered to an animal or animals. This is non-limiting and illustrated herein only by way of example. Other means as are known in the art are also encompassed herein.

Activation of the light member can be by causing two or more precursor chemicals to mix inside the light member. For example, a separator inside the light member can keep the precursor chemicals separate. Upon rupture of the separator the precursor chemicals mix resulting in a fluorescent reaction. Rupture can be caused by exerting force on the separator in the form of compression or bending. As a non-limiting example, the light member can be compressed or bent by the end user thereby causing the separator to rupture which causes mixing of the precursor chemicals.

In some other embodiments, actuation of the light member is done by exposing the light member to light for a set time period. The light may be may be man-made (e.g., a lightbulb) or natural (e.g., sunlight). The set time period to activate the light member will vary depending on the nature of the light member and the length of time the end-user desires the fluorescence to continue. Instructions for actuation for these embodiments, including the set time period required for actuation, would be included with the package and the light member.

The Figures included herein illustrate one desirable embodiment of the package that comprises a light member—a bottle with a serum cap and septa that is commonly used for animal vaccines and other medicaments. This is not intended to be limiting and other types of packages are included in any and all embodiments disclosed elsewhere herein.

As shown in FIG. 23, light member 120 is integrated into the septum cap of package 110 having label 130 comprising a medicament (not shown). It may be in the form of a ring that partially (not-shown in the Figure) or completely (as shown in the Figure) outlines the mouth of package 110. In such an embodiment, the outline around the mouth of the package does not interfere with access to the contents of the package. Additionally, the light member may be permanently affixed to the serum cap or it may be added by the end-user. The light member would not interfere with the needle in accessing the contents of the package. Such a light member may be in the form of an outline of the septum cap thereby providing an a non-illuminated target for the syringe needle as shown. In another aspect, the septa of the serum cap itself would be fluorescent (not shown in the Figure), thereby providing an illuminated target for the syringe needle.

In still yet another aspect, the light member is in the form of a fluorescent paint that is painted onto the package. As one non-limiting example, the fluorescent paint encircles the septa of the serum cap in the same manner as illustrated in FIG. 23. The paint would be applied by the manufacturer at the point of origin or prior to delivery to the end-user and be permanently affixed to the serum cap.

In all aspects, the light member would preferably not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

As shown in FIG. 24, the package 110 comprises the light member 140 that is completely integrated into the label of the package. Different parts of the label may comprise the light member, and the example shown here is only illustrative, not limiting. In some embodiments, the light member comprises only part of the label. In some embodiments, the light member comprises the entire label. In this example, the fluorescence does not interfere with the contents of the label leaving it clearly legible to the end-user as required under regulatory guidelines. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

As shown in FIG. 25, the package 110 comprises the light member 170 that is integrated into the external packaging of a two part medicament. Some medicaments, including animal vaccines, are commercially available as a lyophilized solid that must be reconstituted prior to administration to the animal. Different parts of the label on the packaging comprising both components of the medicament may comprise the light member, and the example shown here is only illustrative, not limiting. In this example, the fluorescence does not interfere with the contents of the label leaving it clearly legible to the end-user as required under regulatory guidelines. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

As shown in FIGS. 26 and 27, the light member 120 is in the form of a sleeve that is placed around the package 110 comprising a medicament. The sleeve may be placed around the package before or after actuation of the light member. Additionally, the sleeve may be in place prior to delivery to the end user, or it may be put in place by the end user. In FIG. 26, the sleeve is mostly transparent except for the fluorescent outline provided by the sleeve and the label 130 is visible through the sleeve. Label information may or may not be provided on the sleeve thereby improving identification and brand recognition under poor light conditions. Such a configuration would be useful under circumstances where two or more different medicaments must be administered at the same time. In FIG. 27, the entire sleeve surrounding the package 110 comprises the light member 120 and is fluorescent thereby improving visibility under poor light conditions. In all aspects, the light member would not interfere with or affect the medicament inside the package during access by a syringe needle. With this embodiment, the label 130 would not be visible through the sleeve. In some aspects, the package would be suitable for use with an animal vaccination gun, and the light member would not interfere with loading the package into the vaccination gun. The light member may use any source of lighting as disclosed herein.

As shown in FIG. 28, the light member 120 is in the form of a structure that is attached to the serum cap of the package 110 comprising a medicament. In such an embodiment, the outline around the mouth of the package does not interfere with access to the contents of the package or view of the label 130. Additionally, the light member may be permanently affixed to the serum cap or it may be added by the end-user. The light member would not interfere with the needle in accessing the contents of the package. Such a light member may be in the form of an outline of the septum cap thereby providing a non-illuminated target for the syringe needle similar to that illustrated in FIG. 23. Additionally, the part of the light member not encompassing the serum cap may or may not be attached to the side of the package. In some embodiments, the light member is completely attached to the package, while in other aspects, only the part of the light member surrounding the serum cap is attached. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

As shown in FIGS. 29 and 30, the light member 120 is in the form of a structure attached to the side (FIG. 30) or the bottom (FIG. 29) of the package 110. The light member may be attached to the package prior to delivery to the end-user or it may be attached by the end-user after delivery. In either aspect, the light member does not impede the label 130. A side view of the fluorescent member in FIG. 30 is also shown. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 31:
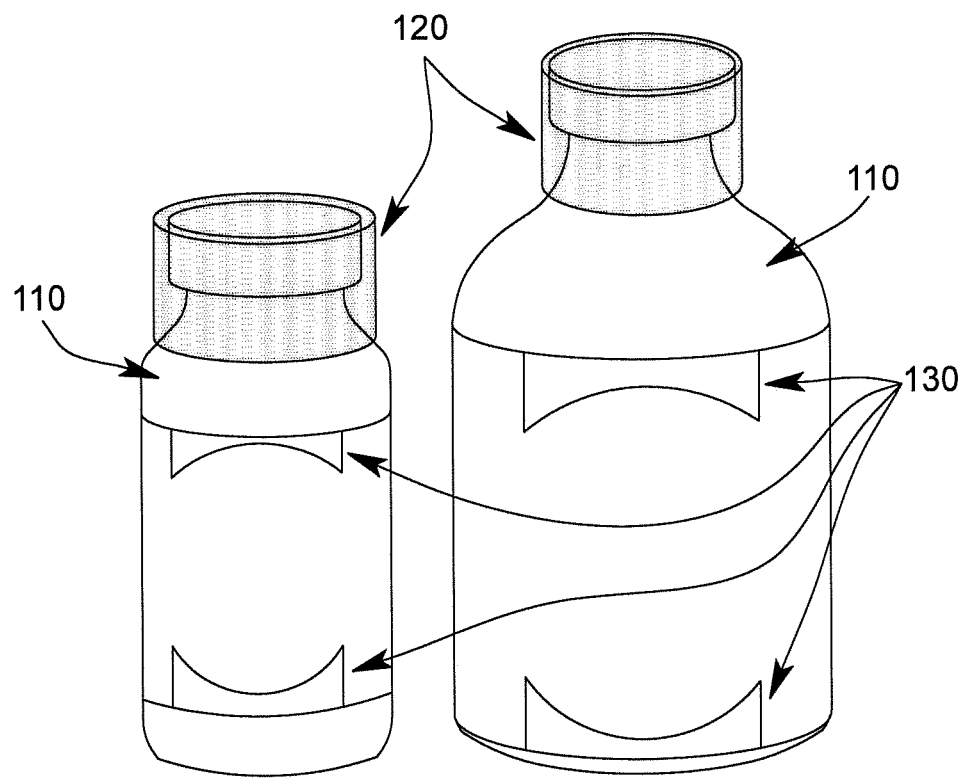
FIG. 31 is one embodiment where the light member is a sleeve that fits around a serum cap on a package.

As shown in FIG. 31, the light member 120 comprises a sleeve or ring around the opening of the package 110. Such a ring can be put in place prior to delivery to the end user or by the end-user after delivery. This ring would provide improved illumination of the septum cap of the package thereby reducing the likelihood of sticking a syringe needle in the wrong location (e.g., the hand of the end-user holding the package). In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 32:
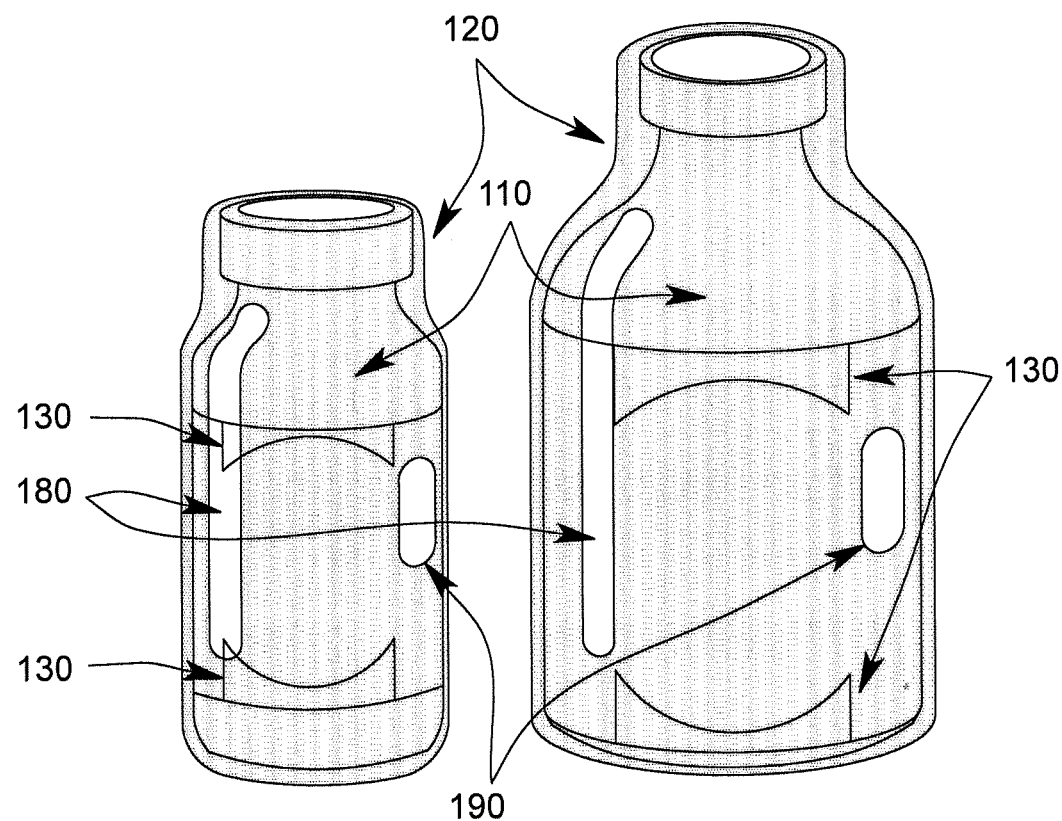
FIG. 32 is one embodiment where the light member is a sleeve that fits over a package and includes an LED light source.

As shown in FIG. 32, the light member 120 comprises a sleeve that contains an additional opening 180 along the surface of the light member so that the end-user may more clearly observe the contents of the package 110. For example, the end-user may observe the amount of the medicament remaining inside the package. The light member may include a plurality of additional openings placed in any location on the light member. Additionally, as shown in this embodiment, the light member uses LED lighting and includes an on/off switch 190 for actuation on the side of the light member. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 34:
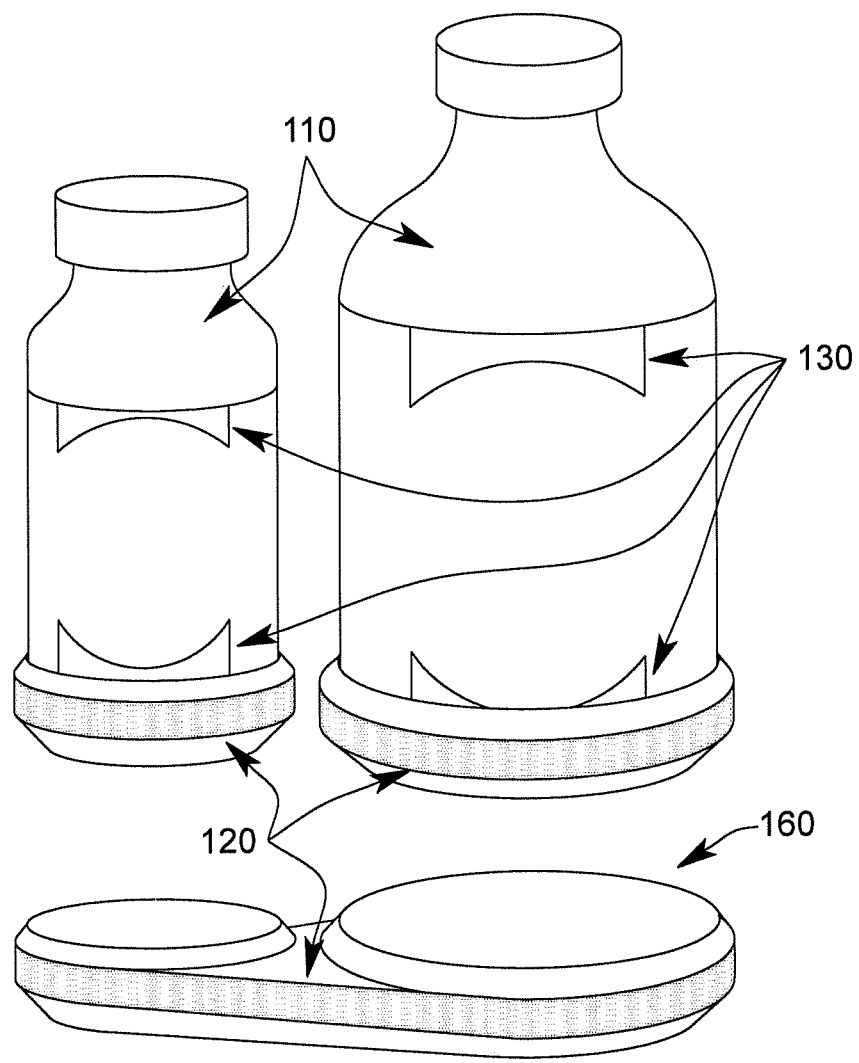
FIG. 34 is one embodiment where the light member is a ring that fits around a pair of packages that comprise a medicament and includes an LED light source.

As shown in FIGS. 33 and 34, the light member 120 comprises an LED light source 150. In such an embodiment, the LED has at least an on/off switch (not shown) that can be activated by the end-user. In FIG. 33, the light member 120 is attached to the serum cap of the package 110 thereby providing an improved visual identification for the septa. In FIG. 34, the light member 120 is in the form of a band attached to the package 110 thereby providing improved visual identification in low light conditions. In this example, the light member is in the form of a band that fits around the bottom of a package. In another aspect, the light member is in the form of a tray or holder 160 where a two part medicament is placed. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Further aspects of the present invention are: 1. A package comprising:
a medicament, and
a light member, wherein the light member is located on the exterior of the package, and wherein the light member is configured to provide information to an end user through the emission of light.
2. The package according to aspect 1, wherein the information provided to the end user is related to the viability of the medicament, the location of the package, the location of a specific part of the package, or any combination thereof.
3. The package according to aspect 1, wherein the medicament is a veterinary product selected from the group consisting of antibiotics, vaccines, nutritional supplements, growth supplements, antifungal medication, antiparasitic medication, hormones and combinations thereof.
4. The package according to aspect 1, wherein the medicament is a vaccine for bovine viral diarrhea.
5. The package according to aspect 1, wherein the light member is configured to emit light for a predetermined period of time.
6. The package according to aspect 1, wherein light emission is produced by fluorescence, chemiluminescence, or a light emitting diode.
7. The package according to aspect 1, wherein the light member uses passive illumination, active illumination or a combination thereof.
8. The package according to aspect 1, wherein the light member is part of the exterior adornment of the package.
9. The package according to aspect 9, wherein the light member is attached to the exterior of the package by the end-user.
10. The package according to aspect 1, wherein the light member comprises part of the label of the package.
11. The package according to aspect 1, wherein the light member partially or completely surrounds a mouth or a cap of the package.

12. The package according to aspect 1, wherein the light member is activated by the combination of two or more chemicals.

13. A method for determining the viability of a medicament in a package, said method comprising:

activating a light member on the package comprising said medicament when the package is opened; and observing the fluorescence in the light member.

14. The method according to aspect 13, wherein activating the light member comprises causing two or more precursor chemicals to mix.

15. The method according to aspect 13, wherein activating the light member comprises exposing the light member to light for at least a set time period.

16. The method according to aspect 13, wherein the medicament is a veterinary product selected from the group consisting of antibiotics, vaccines, nutritional supplements, growth supplements, antifungal medication, antiparasitic medication, hormones and combinations thereof.

17. The method according to aspect 13, wherein the medicament is a vaccine for bovine viral diarrhea.

18. The method according to aspect 13, wherein the light member fluoresces for a period of time equal to the length of time for which the medicament remains viable.

19. A method for determining the viability of a medicament in a package, the method comprising:

opening the package and activating a light member located on the package containing the medicament such that the light member emits fluorescent light; and observing a change in color in the light member over a period of time.

20. The method according to aspect 19, wherein the color changes occurs at a time when the medicament become non-viable.

What is claimed is:

1. A container system, comprising:
    at least two containers, and
    a light member which is configured to provide information through the emission of light,
    wherein the light member is triggerable to provide the information through the emission of light produced by chemiluminescence in response to an event related to preparing a mixture from contents of the containers,
    wherein the containers, in a transporting position, are releasably connected to one another, and wherein the activation of the light member is responsive to separation of the containers from one another while the containers are closed for preparation of a fluidic connection between the containers.

2. The container system according to claim 1, wherein the containers are connected together, and wherein said event is separation of the containers from one another and preparation of a fluidic connection between the containers.

3. The container system according to claim 2, wherein the containers each comprise a connecting arrangement, and wherein the connecting arrangements are configured for enabling said preparation of the fluidic connection between the containers.

4. The container system according to claim 3, wherein the connecting arrangements are configured to prepare the fluidic connection by at least one of insertion of one connecting arrangements into the other and twisting the connecting arrangements relative to one another.

5. The container system according to claim 3, wherein the container system is configured to activate the light member to emit light or to change properties of light emitted by the light member when the fluidic connection is prepared between the containers.

6. The container system according to claim 1, wherein the light member is configured to emit light for a predetermined period of time or to change properties of light emitted by the light member after a predetermined period of time.

7. Container system according to claim 6, wherein said period of time corresponds to a length of time for which the medicament or mixture remains viable.

8. The container system according to claim 1, wherein the information provided to the end user is related to the viability of a medicament or mixture which can be prepared by the mixing of the contents of the containers.

9. The container system according to claim 1, wherein the light member uses passive illumination, active illumination or a combination thereof.

10. The container system according to claim 1, wherein the light member is part of an exterior adornment of at least one of the containers.

11. The container system according to claim 1, wherein the light member is activated by the combination of two or more chemicals.

12. A method for determining the viability of a medicament or mixture which is prepared by mixing contents of at least two containers using a fluidic connection between said containers, comprising using a lighting member to provide information through the emission of light in response to an event related to preparing a mixture from the contents of the containers,
    wherein activating of the light member comprises causing two or more precursor chemicals to mix,
    wherein the containers, in a transporting position, are releasably connected to one another, and wherein the activation of the light member is responsive to separation of the containers from one another while the containers are closed for preparation of a fluidic connection between the containers.

13. The method according to claim 12, wherein the light member emits light for a period of time or changes a lighting property after said period of time.

14. The method according to claim 13, wherein said period of time is equal to a length of time for which the medicament or mixture remains viable.

15. The method according to claim 14, wherein a color change occurs or the light member stops emitting light at the time when the medicament or mixture become non-viable.

16. The method according to claim 12, wherein said event is at least one of separating of the containers from one another and preparing a fluidic connection between the containers.

17. The method according to claim 12, wherein the containers each comprise a connecting arrangement configured for the preparation of the fluidic connection between the containers, and wherein said event is preparing of a fluidic connection between the containers.

* * * * *